(12) United States Patent
Stoessel et al.

(10) Patent No.: US 9,382,253 B2
(45) Date of Patent: Jul. 5, 2016

(54) METAL COMPLEXES

(75) Inventors: Philipp Stoessel, Frankfurt am Main (DE); Dominik Joosten, Frankfurt am Main (DE); Anja Gerhard, Egelsbach (DE); Esther Breuning, Ober-Ramstadt (DE); Niels Schulte, Kelkheim (DE)

(73) Assignee: Merck Patent GmbH, Darmstadt (DE)

( * ) Notice: Subject to any disclaimer, the term of this patent is extended or adjusted under 35 U.S.C. 154(b) by 538 days.

(21) Appl. No.: 13/809,905

(22) PCT Filed: Jun. 17, 2011

(86) PCT No.: PCT/EP2011/002986
§ 371 (c)(1),
(2), (4) Date: Jan. 14, 2013

(87) PCT Pub. No.: WO2012/007087
PCT Pub. Date: Jan. 19, 2012

(65) Prior Publication Data
US 2013/0112921 A1    May 9, 2013

(30) Foreign Application Priority Data

Jul. 16, 2010  (DE) .................. 10 2010 027 316

(51) Int. Cl.
| | | |
|---|---|---|
| H01L 51/00 | (2006.01) |
| C07F 15/00 | (2006.01) |
| C07D 487/04 | (2006.01) |
| C07C 49/796 | (2006.01) |
| C07D 251/24 | (2006.01) |
| C07D 487/12 | (2006.01) |
| C09K 11/06 | (2006.01) |
| H05B 33/14 | (2006.01) |
| C08F 230/04 | (2006.01) |
| C09B 57/00 | (2006.01) |
| C09B 57/10 | (2006.01) |
| H01L 51/50 | (2006.01) |

(52) U.S. Cl.
CPC ............ *C07D 487/04* (2013.01); *C07C 49/796* (2013.01); *C07D 251/24* (2013.01); *C07D 487/12* (2013.01); *C07F 15/0033* (2013.01); *C08F 230/04* (2013.01); *C09B 57/00* (2013.01); *C09B 57/10* (2013.01); *C09K 11/06* (2013.01); *H01L 51/0043* (2013.01); *H01L 51/0085* (2013.01); *H01L 51/0087* (2013.01); *H05B 33/14* (2013.01); *C09K 2211/1007* (2013.01); *C09K 2211/1029* (2013.01); *C09K 2211/1044* (2013.01); *C09K 2211/1059* (2013.01); *C09K 2211/1088* (2013.01); *C09K 2211/185* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| 2009/0165846 A1 | 7/2009 | Johannes et al. |
| 2011/0284799 A1 | 11/2011 | Stoessel et al. |
| 2012/0199794 A1 | 8/2012 | Stoessel et al. |
| 2015/0018549 A1 | 1/2015 | Knowles et al. |

FOREIGN PATENT DOCUMENTS

| CN | 101300264 A | 11/2008 |
| CN | 101415717 A | 4/2009 |
| CN | 102282150 A | 12/2011 |
| CN | 102939296 A | 2/2013 |
| JP | 2009-507064 A | 2/2009 |
| JP | 2009-102533 A | 5/2009 |
| JP | 2009-526071 A | 7/2009 |
| JP | 2010-141008 A | 6/2010 |
| JP | 2012-516831 A | 7/2012 |
| JP | 2013-507404 A | 3/2013 |
| WO | WO 2007/028822 A1 | 3/2007 |
| WO | WO-2007088768 A1 | 8/2007 |
| WO | WO-2010/086089 A1 | 8/2010 |
| WO | WO-2011044988 A1 | 4/2011 |
| WO | WO 2011/157339 A1 | 12/2011 |
| WO | WO 2010/051100 | 5/2014 |

OTHER PUBLICATIONS

Lai et al., "A study on the preparation and photophysical properties of an iridium(III) complexed homopolymer", Journal of Material Science, vol. 19, pp. 4952-4959 (2009).
English translation of Chinese Office Action issued on Sep. 2, 2014 for Application No. 201180034296.3.
International Search Report for PCT/EP2011/002986 mailed Oct. 10, 2011.
Hennig, H. et al, Zeitschrift fuer Chemie, 1971, Iss. 3, pp. 115-116.
Hennig, H. et al, Journal fuer Praktische Chemie, 1975, vol. 317, Iss. 5, pp. 853-860.
English translation of Japanese Office Action mailed on May 26, 2015 for Application No. 2013-519972.

*Primary Examiner* — Ling Choi
*Assistant Examiner* — Catherine S Branch
(74) *Attorney, Agent, or Firm* — Drinker Biddle & Reath LLP

(57) ABSTRACT

The present invention relates to metal complexes which contain polymerizable groups and to the polymers obtained using these metal complexes and to electronic devices, in particular organic electroluminescent devices, comprising these polymers. The metal complexes are compounds of the formula (1), containing a moiety M(L)n of the formula (2) or formula (3).

21 Claims, No Drawings

METAL COMPLEXES

CROSS-REFERENCE TO RELATED APPLICATIONS

This application is a national stage application (under 35 U.S.C. §371) of PCT/EP2011/002986, filed Jun. 17, 2011, which claims benefit of German application 10 2010 027 316.3, filed Jul. 16, 2010 which are both incorporated by reference.

The present invention relates to metal complexes having polymerisable groups and to the corresponding polymers obtained from these monomers, which are suitable for use as emitting materials, in particular as blue- and green-emitting materials, but also for yellow, orange or red emission, in an organic electroluminescent device.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are frequently organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters. In general, however, there is still a need for improvement in OLEDs which exhibit triplet emission, in particular with respect to efficiency, operating voltage and lifetime. This applies, in particular, to OLEDs which emit in the relatively short-wave region, i.e. green and in particular blue.

In accordance with the prior art, iridium complexes, in particular, are employed as triplet emitters in phosphorescent OLEDs. For blue phosphorescence, in particular for saturated deep-blue emission, however, there continues to be a considerable need for improvement. This also applies, in particular, to materials which are processed from solution.

Organic electroluminescent devices frequently have the following general layer structure:
(1) substrate,
(2) electrode, frequently metallic or inorganic, but also comprising organic or polymeric conductive materials,
(3) charge-injection layer(s) or interlayer(s), for example for equalisation of unevenness of the electrode ("planarisation layer"), frequently comprising a conductive, doped polymer,
(4) emission layer, usually comprising at least one emitter and at least one matrix material or a material which simultaneously acts as emitter and as matrix material,
(5) optionally further charge-transport, charge-injection or charge-blocking layers,
(6) counterelectrode, materials as mentioned under (2),
(7) encapsulation.

The above arrangement represents the general structure of an organic electroluminescent device, where various layers can be combined, resulting in the simplest case in an arrangement comprising two electrodes, between which an organic layer is located. In this case, the organic layer carries out all functions, including the emission of light. A system of this type is described, for example, in WO 90/13148 A1 on the basis of poly-(p-phenylenes).

A problem which arises in a "three-layer system" of this type is, however, the lack of control of charge separation and the lack of a way of optimising the individual constituents in different layers with respect to their properties, as is possible, for example, in OLEDs based on low-molecular-weight compounds due to a multilayered structure.

Organic electroluminescent devices are produced either by vacuum evaporation or from solution. Processing from solution, for example by printing processes, is industrially less complex, and it is thus also possible to coat larger areas with the organic semiconductor. However, organic electroluminescent devices which have been produced from solution currently still have worse properties with respect to efficiency, lifetime and operating voltage than organic electroluminescent devices which have been obtained by vacuum evaporation.

An OLED based on low-molecular-weight compounds comprises, for example, one or more organic hole-injection layers, hole-transport layers, emission layers, electron- or exciton-blocking layers, hole-blocking layers, electron-transport layers and/or electron-injection layers as well as an anode and a cathode. The advantage of a multilayered structure of this type consists in that different functions of charge injection, charge transport and emission can be divided into the different layers and the properties of the respective layers can thus be optimised separately.

The application of the layers in OLEDs based on low-molecular-weight compounds is usually carried out by vapour deposition in a vacuum chamber. However, this process is industrially complex and unsuitable for large molecules, such as, for example, polymers. Polymeric OLED materials are therefore usually applied by coating from solution. However, the production of a multilayered organic structure by coating from solution requires that the solvent of the layer to be applied does not re-dissolve, swell or even destroy the respective preceding layer. The choice of solvent frequently proves to be difficult, since the organic polymers employed usually have similar chemical structures and properties, in particular similar solution properties. Correspondingly, polymeric OLEDs (PLEDs) in accordance with the prior art are usually built up from a single-layered or two-layered semiconducting structure, where, for example, one of the layers is used for hole injection and hole transport and the second layer is used, for example, for the injection and transport of electrons and for emission. In particular on use of crosslinked layers, more layers may also be present in the OLED.

However, a multilayered structure, as usually used in OLEDs based on low-molecular-weight compounds, would also be advantageous in the case of polymeric OLEDs. To this end, various approaches are described in the prior art. Thus, for example, EP 0637899 discloses an electroluminescent arrangement comprising one or more organic layers, where one or more of the layers are crosslinked thermally or with radiation induction. Furthermore, WO 96/20253 discloses a luminescent, film-forming, crosslinked polymer in which azide groups which are bonded to the main polymer chain are thermally crosslinked. U.S. Pat. No. 6,107,452 discloses a process for the formation of a multilayered device in which oligomers having terminal vinyl groups are deposited from solution and crosslinked to give insoluble polymers, on which further layers can be deposited. K. Meerholz et al. (*Nature* 2003, 421, 829-832) disclose the production of a multilayered, organic electroluminescent device in which crosslinking is achieved by incorporation of oxetane-functionalised spirobifluorene basic units into the polymer. There continues to be a demand for soluble compounds, in particular polymers, which can be processed from solution, and for compounds which have a functional group which is suitable for crosslinking and can thus be crosslinked to give insoluble polymers.

The object of the present invention is therefore the provision of metal complexes which are suitable as emitters for use in OLEDs and which are suitable for incorporation into polymers. In particular, the object is to provide emitters which are also suitable for blue-phosphorescent OLEDs. The object of the invention is furthermore the provision of polymers which are obtained by the polymerisation of these functionalised metal complexes.

Surprisingly, it has been found that certain metal chelate complexes described in greater detail below achieve this object. These metal complexes can readily be incorporated into polymers via the polymerisable group. The polymers obtained in this way exhibit good properties, in particular with respect to efficiency, lifetime and operating voltage, on use in an organic electroluminescent device. The present invention therefore relates to these metal complexes, to polymers containing these metal complexes and to organic electroluminescent devices which comprise these polymers.

The prior art discloses iridium complexes which contain imidazophenanthridine derivatives or diimidazoquinazoline derivatives as ligands (WO 2007/095118). These complexes can result in blue phosphorescence on use in organic electroluminescent devices, depending on the precise structure of the ligand. Further improvements are still desirable here with respect to efficiency, operating voltage and lifetime. In particular, there is also still a need for improvement here with respect to the colour coordinates in order to be able to achieve deep-blue emission.

WO 2010/086089 furthermore discloses iridium complexes which contain imidazoisoquinoline derivatives as ligands. Here too, there continues to be a need for improvement, in particular in the case of complexes which are processed from solution.

The invention relates to a compound of the formula (1),

containing a moiety $M(L)_n$ of the formula (2) or formula (3):

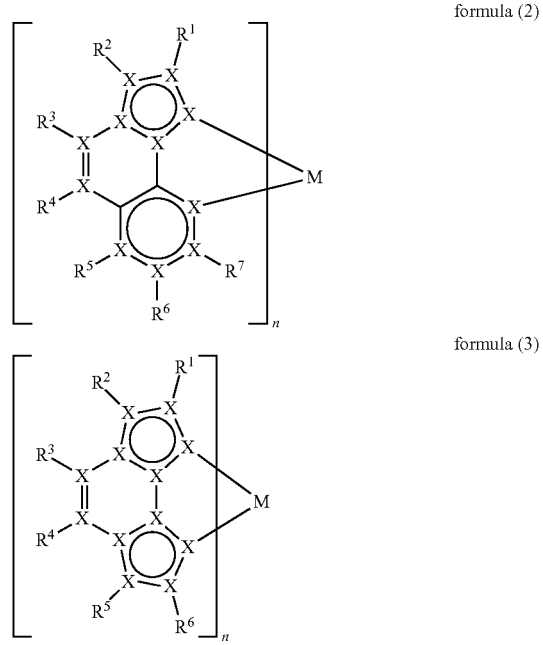

where the following applies to the symbols and indices used:
M is a metal;
X is selected on each occurrence, identically or differently, from the group consisting of C and N; all X here together represent a 14 π electron system;

$R^1$ to $R^7$ is on each occurrence, identically or differently, a polymerisable group PG or H, D, F, Cl, Br, I, $N(R^8)_2$, CN, $NO_2$, $Si(R^8)_3$, $B(OR^8)_2$, $C(=O)R^8$, $P(=O)(R^8)_2$, $S(=O)R^8$, $S(=O)_2R^8$, $OSO_2R^8$, a straight-chain alkyl, alkoxy or thioalkoxy group having 1 to 40 C atoms or an alkenyl, alkynyl or imine group having 2 to 40 C atoms or a branched or cyclic alkyl, alkoxy or thioalkoxy group having 3 to 40 C atoms, where the above-mentioned alkyl, alkoxy, thioalkoxy, alkenyl, alkynyl and imine groups may each be substituted by one or more radicals $R^8$, where one or more non-adjacent $CH_2$ groups may be replaced by $R^8C=CR^8$, $C≡C$, $Si(R^8)_2$, $Ge(R^8)_2$, $Sn(R^8)_2$, $C=O$, $C=S$, $C=Se$, $C=NR^8$, $P(=O)(R^8)$, SO, $SO_2$, $NR^8$, O, S or $CONR^8$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which may be substituted by one or more radicals $R^8$, or an aralkyl or heteroaralkyl group having 5 to 60 aromatic ring atoms, which may be substituted by one or more radicals $R^8$, or a diarylamino group, diheteroarylamino group or arylheteroarylamino group having 10 to 40 aromatic ring atoms, which may be substituted by one or more radicals $R^8$; $R^1$ and $R^2$ and/or $R^2$ and $R^3$ and/or $R^4$ and $R^5$ and/or $R^5$ and $R^6$ and/or $R^6$ and $R^7$ here may also form a mono- or polycyclic, aliphatic, aromatic and/or benzo-fused ring system with one another; furthermore, $R^3$ and $R^4$ may form a mono- or polycyclic, in each case aliphatic ring system with one another; with the proviso that $R^1$, $R^2$, $R^3$, $R^4$, $R^5$, $R^6$ or $R^7$ represents a free electron pair if the group X to which this radical $R^1$, $R^2$, $R^3$, $R^4$, $R^5$, $R^6$ or $R^7$ is bonded is a nitrogen atom having a saturated valence;

$R^8$ is on each occurrence, identically or differently, H, D, F, Cl, Br, I, $N(R^9)_2$, CN, $NO_2$, $Si(R^9)_3$, $B(OR^9)_2$, $C(=O)R^9$, $P(=O)(R^9)_2$, $S(=O)R^9$, $S(=O)_2R^9$, $OSO_2R^9$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals $R^9$, where one or more non-adjacent $CH_2$ groups may be replaced by $R^9C=CR^9$, $C≡C$, $Si(R^9)_2$, $Ge(R^9)_2$, $Sn(R^9)_2$, $C=O$, $C=S$, $C=Se$, $C=NR^9$, $P(=O)(R^9)$, SO, $SO_2$, $NR^9$, O, S or $CONR^9$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^9$, or an aryloxy or heteroaryloxy group having 5 to 60 aromatic ring atoms, which may be substituted by one or more radicals $R^9$, or an aralkyl or heteroaralkyl group having 5 to 60 aromatic ring atoms, which may be substituted by one or more radicals $R^8$, or a diarylamino group, diheteroarylamino group or arylheteroarylamino group having 10 to 40 aromatic ring atoms, which may be substituted by one or more radicals $R^9$; two or more adjacent radicals $R^8$ here may form a mono- or polycyclic, aliphatic or aromatic ring system with one another;

$R^9$ is on each occurrence, identically or differently, H, D, F, CN or an aliphatic, aromatic and/or heteroaromatic hydrocarbon radical having 1 to 20 C atoms, in which, in addition, one or more H atoms may be replaced by D or F; two or more substituents $R^9$ here may also form a mono- or polycyclic, aliphatic or aromatic ring system with one another;

PG is a polymerisable group, with the proviso that the polymerisable group is not selected from Cl, Br, I and $B(OR^8)_2$; and furthermore with the proviso that, if one or more of the radicals $R^1$ to $R^7$ as polymerisable group PG are selected from an alkenyl or an alkynyl group, it is a terminal alkenyl or alkynyl group having 3 to 40 C atoms, where individual $CH_2$ groups or individual H atoms may also be replaced by the groups mentioned in the case of $R^1$ to $R^7$; and furthermore with the proviso that, if one or more of the radicals $R^1$ to $R^7$ as polymerisable group PG is selected from a group $Si(R^8)_3$, $R^8$ stands either for Cl or for an alkoxy group having 1 to 40 C atoms;

L' is, identically or differently on each occurrence, any desired co-ligand;

n is 1, 2 or 3;

m is 0, 1, 2, 3 or 4;

a plurality of ligands L here may also be linked to one another or L may be linked to L' via a single bond or any desired bridge V and thus form a tridentate, tetradentate, pentadentate or hexadentate ligand system;

characterised in that at least one of the radicals $R^1$ to $R^7$ and/or at least one radical on the ligand L' stands for a polymerisable group PG.

Both the ligand L as a whole and also individual atoms X in the ligand L may be charged.

The indices n and m here are selected so that the coordination number on the metal M corresponds overall, depending on the metal, to the usual coordination number for this metal. This is usually the coordination number 4, 5 or 6 for transition metals, depending on the metal. It is generally known that metal coordination compounds have different coordination numbers, i.e. bind a different number of ligands, depending on the metal and on the oxidation state of the metal. Since the preferred coordination numbers of metals and metal ions in various oxidation states belong to the general expert knowledge of the person skilled in the art in the area of organometallic chemistry or coordination chemistry, it is readily possible for the person skilled in the art to use a suitable number of ligands, depending on the metal and its oxidation state and depending on the precise structure of the ligands L and L', and thus to select the indices n and m suitably.

The ligands L are bidentate ligands, which bond to the metal M via one carbon atom and one nitrogen atom or via two carbon atoms or via two nitrogen atoms and which can be neutral, monoanionic or dianionic, preferably monoanionic. If the ligand bonds to the metal via two carbon atoms, a coordinating atom is preferably a carbene carbon atom and the ligand preferably contains precisely two nitrogen atoms in the coordinating carbene ring. In a preferred embodiment of the invention, the ligand L bonds to the metal M via one carbon atom and one nitrogen atom.

All atoms X together form a 14 π-electron system. Each carbon atom here contributes 1 π-electron to the overall electron system. Each nitrogen atom which is only bonded in a 6-membered ring likewise contributes 1 π-electron to the overall electron system. Each nitrogen atom which is bonded simultaneously in a 5-membered ring and a 6-membered ring contributes 2 π-electrons to the overall electron system. Each nitrogen atom which is only bonded in a 5-membered ring contributes 1 or 2 π-electrons to the overall electron system. It depends on the bonding of the nitrogen in the 5-membered ring whether this nitrogen atom contributes 1 or 2 π-electrons to the overall electron system. The circle in a ring in formulae (2) and (3) represents a 6 π-electron system, as is usually used for the representation of aromatic or heteroaromatic structures in organic chemistry. The following structures again explain when the nitrogen contributes 1 or 2 π-electrons (shown only as electrons in the scheme) to the overall π-electron system:

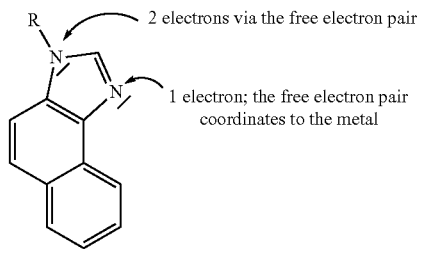

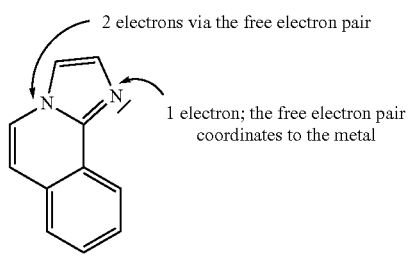

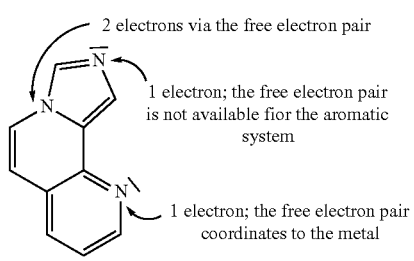

A nitrogen atom with a saturated valence in the sense of this invention is taken to mean a nitrogen atom which formally forms either one single bond and one double bond or three single bonds within the aromatic skeleton. In these cases, the radical $R^1$ to $R^7$ which is bonded to this nitrogen atom represents a free electron pair. For the purposes of this invention, a nitrogen atom with an unsaturated valence is taken to mean, by contrast, a nitrogen atom which formally only forms two single bonds within the aromatic skeleton. In these cases, the radical from $R^1$ to $R^7$ which is bonded to this nitrogen atom represents a radical as defined above and not a free electron pair. The following structures again explain what is taken to mean by a nitrogen atom with a saturated valence:

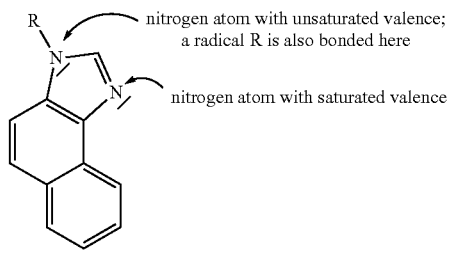

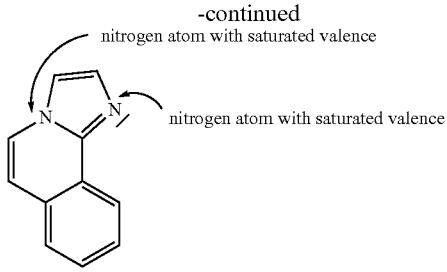

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

The ligands may also bond to the metal via a carbene carbon atom. A cyclic carbene in the sense of this invention is a cyclic group which bonds to the metal via a neutral C atom. Preference is given here to Arduengo carbenes, i.e. carbenes in which two nitrogen atoms are bonded to the carbene C atom. A five-membered Arduengo carbene ring or another unsaturated five-membered carbene ring is likewise regarded as an aryl group in the sense of this invention. In a preferred embodiment of the invention, the cyclic carbene which coordinates to the metal contains precisely two nitrogen atoms which bond to the carbene C atom, but no further nitrogen atoms.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N, O or Si atom or a carbonyl group. Thus, for example, systems such as 9,9'-spirobifluorene, 9,9-diarylfluorene, triarylamine, diaryl ether, stilbene, etc., are also intended to be taken to mean aromatic ring systems in the sense of this invention, as are systems in which two or more aryl groups are interrupted, for example, by a linear or cyclic alkyl group or by a silyl group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo-[2.2.2] octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The compounds of the formula (1) may be charged or uncharged. If the compounds of the formula (1) are charged, they also have one or more counterions. Examples of cationic counterions are alkali metal ions, for example lithium, sodium or potassium, tetraalkylammonium or tetraalkylphosphonium ions, where the alkyl groups each preferably contain 1 to 4 C atoms. Examples of anionic counterions are chloride, bromide, iodide, sulfate, phosphate, tetrafluoroborate or hexafluorophosphate.

Preference is given to compounds of the formula (1), characterised in that they are uncharged, i.e. are electrically neutral. This is achieved in a simple manner by selecting the charges of the ligands L and L' in such a way that they compensate for the charge of the complexed metal atom M.

Preference is furthermore given to compounds of the formula (1), characterised in that the sum of the valence electrons around the metal atom is 16 in tetracoordinated complexes and 16 or 18 in pentacoordinated complexes and 18 in hexacoordinated complexes. This preference is due to the particular stability of these metal complexes.

In a preferred embodiment of the invention, M stands for a transition metal without lanthanides and actinides or for a main-group metal. If M stands for a main-group metal, it preferably stands for a metal from the third, fourth, fifth or sixth main group, in particular for tin, lead, bismuth or tellurium.

Preference is given to compounds of the formula (1) in which M stands for a transition metal without lanthanides and actinides, in particular for a tetracoordinated, pentacoordinated or hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, copper, platinum and gold. Very particular preference is given to iridium and platinum. The metals here can be in various oxidation states. The above-mentioned metals are preferably in the oxidation states Cr(0), Cr(II), Cr(III), Cr(IV), Cr(VI), Mo(0), Mo(II), Mo(III), Mo(IV), Mo(VI), W(O), WOO, W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V); particular preference is given to Mo(0), W(O), Re(I), Ru(II), Os(II), Rh(III), Cu(I), Ir(III) and Pt(II).

In a preferred embodiment of the invention, M is a tetracoordinated metal, and the index n stands for 1 or 2. If the index n=1, one bidentate or two monodentate ligands L', preferably one bidentate ligand L', is (are) also coordinated to the metal M. If the index n=2, the index m=0.

In a further preferred embodiment of the invention, M is a hexacoordinated metal, and the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are also coordinated to the metal. If the index n=2, one bidentate or two monodentate ligands L', preferably one bidentate ligand L', are also coordinated to the metal. If the index n=3, the index m=0.

In a preferred embodiment of the invention, the central ring of the ligand L contains at least one nitrogen atom. Preferred moieties of the formula (2) and of the formula (3) are thus the structures of the following formulae (2a) and (3a),

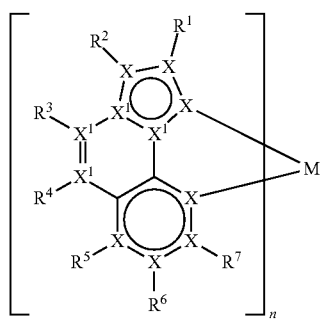

formula (2a)

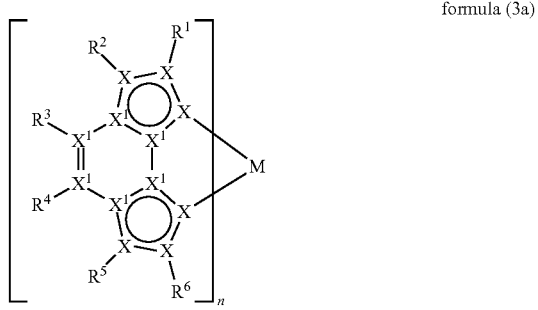

formula (3a)

where the symbols and indices used have the meanings given above and furthermore:

$X^1$ is, identically or differently on each occurrence, C or N, with the proviso that at least one group $X^1$ stands for N.

In a particularly preferred embodiment of the invention, the central ring of the ligand L contains at least one nitrogen atom which is bonded in two rings. Preferred moieties of the formula (2a) and of the formula (3a) are thus the structures of the following formulae (2b) and (3b),

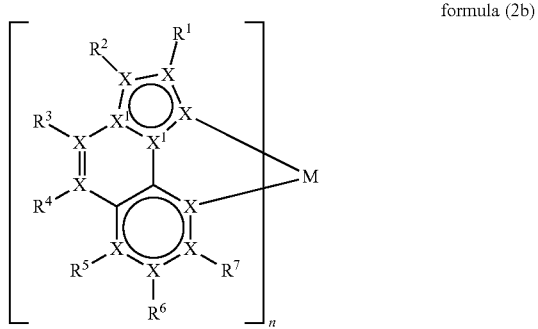

formula (2b)

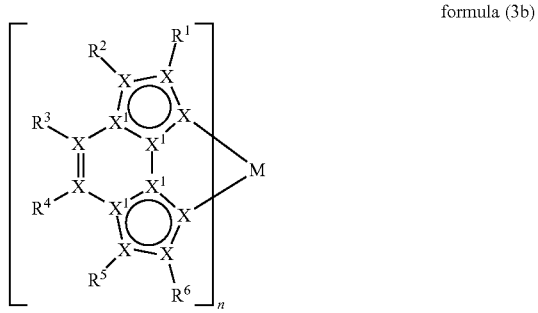

formula (3b)

where the symbols and indices used have the meanings given above.

In a preferred embodiment of the invention, the moieties of the formula (2) are selected from the structures of the following formulae (4), (5) and (6), and the moieties of the formula (3) are selected from the structures of the following formulae (7) and (8), formula (4)

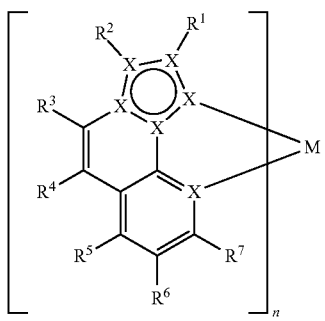

formula (5)

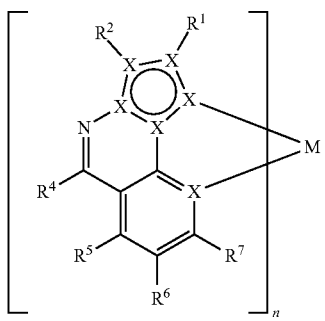

formula (6)

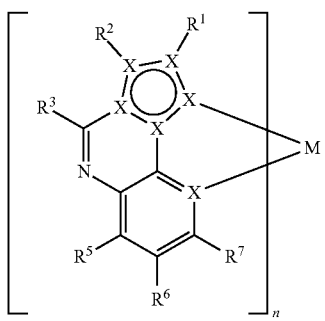

formula (7)

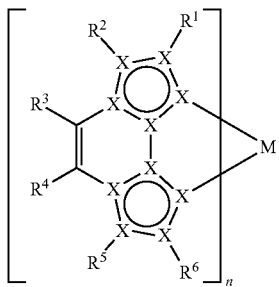

formula (8)

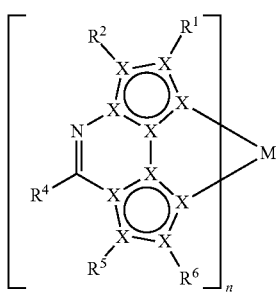

where the symbols and indices have the meanings indicated above.

In a particularly preferred embodiment of the invention, the moieties of the formulae (4) to (8) are selected from the structures of the following formulae (4a) to (8a) in which the central ring of the ligand has at least one nitrogen atom which is bonded in two rings:

formula (4a)

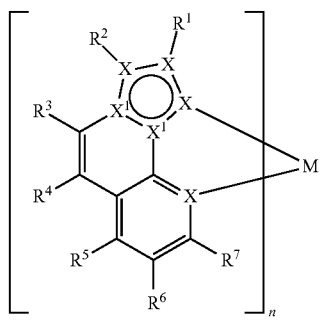

formula (5a)

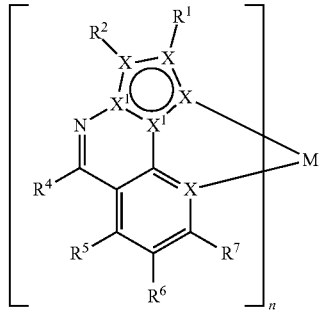

formula (6a)

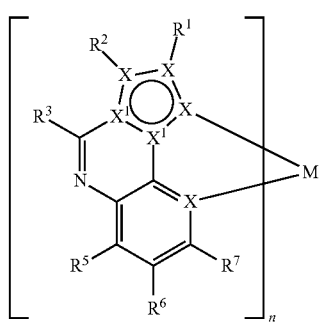

formula (7a)

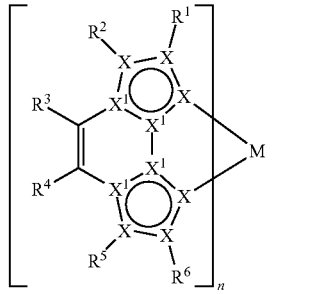

formula (8a)
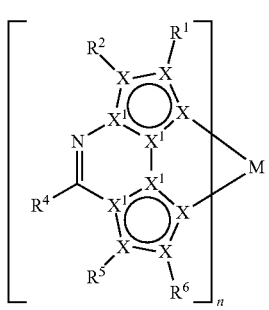
where the symbols and indices have the meanings indicated above.
Particularly preferred embodiments of the moieties of the formulae (4) to (8) and (4a) to (8a) are the structures of the following formulae (9) to (77),
formula (9)
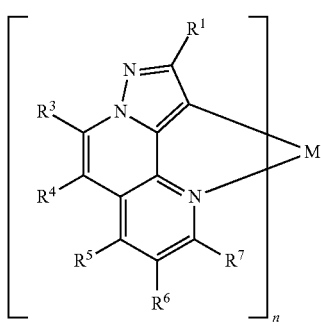
formula (10)
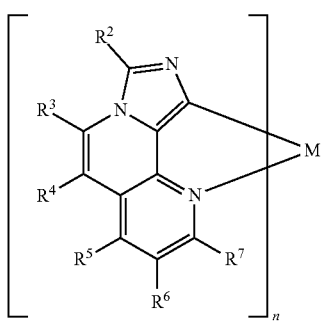
formula (11)
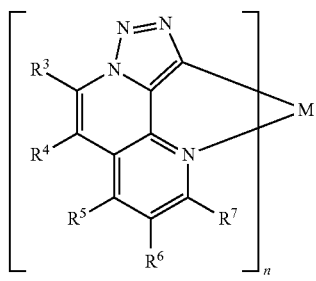
formula (12)
formula (13)
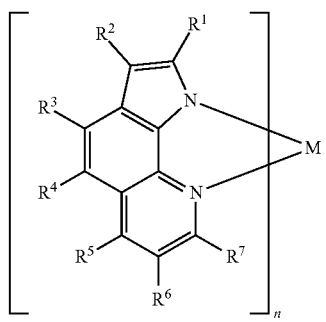
formula (14)
formula (15)
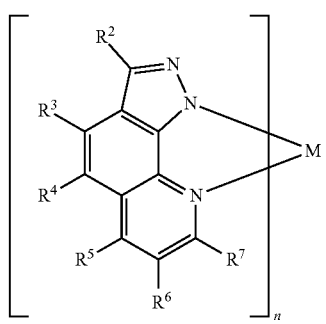
formula (16)
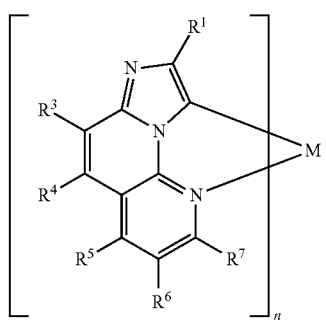

formula (17)
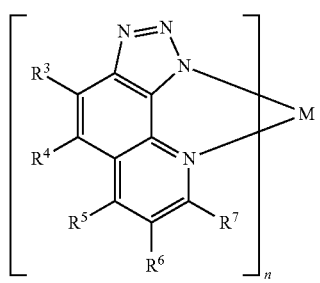
formula (18)
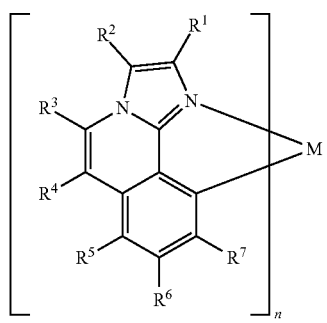
formula (19)
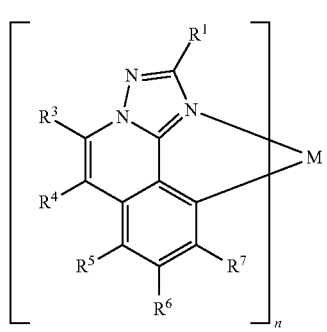
formula (20)
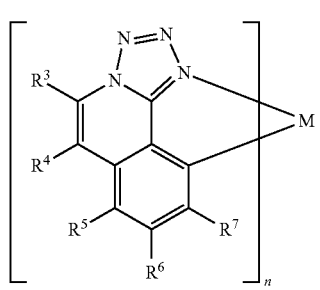
formula (21)
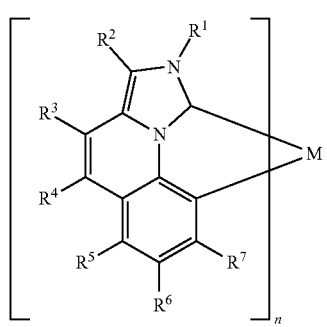
formula (22)
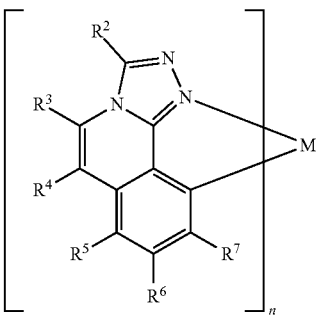
formula (23)
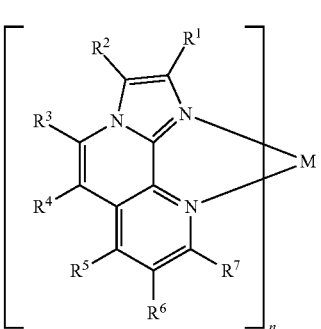
formula (24)
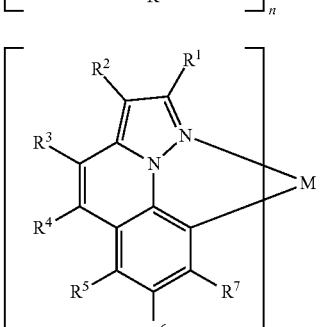
formula (25)
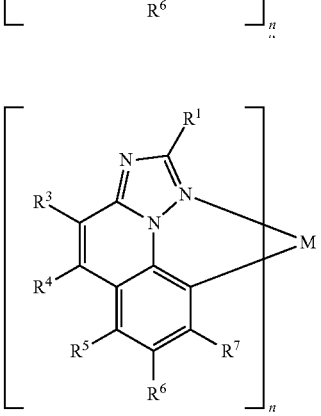
formula (26)
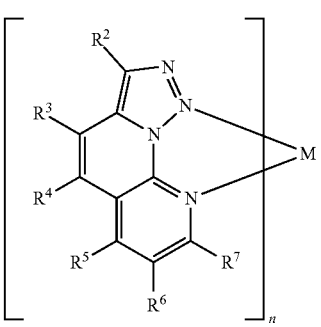

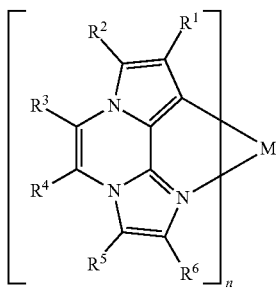
formula (27)
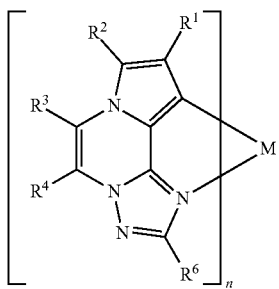
formula (28)
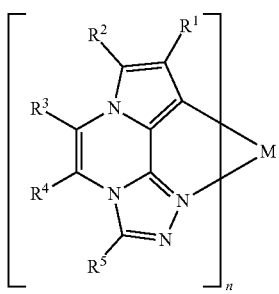
formula (29)
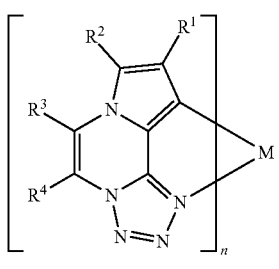
formula (30)
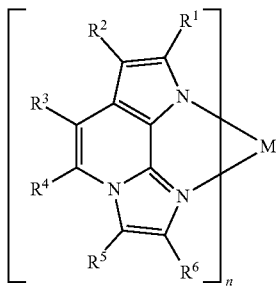
formula (31)
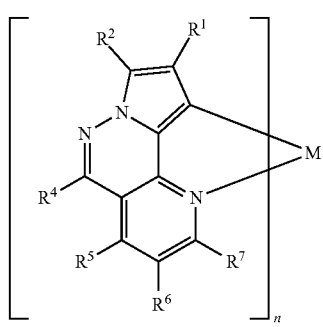
formula (32)
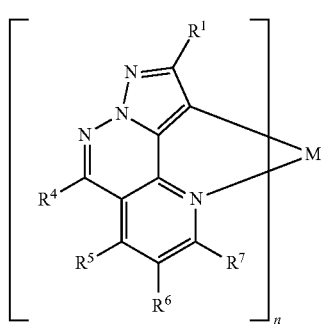
formula (33)
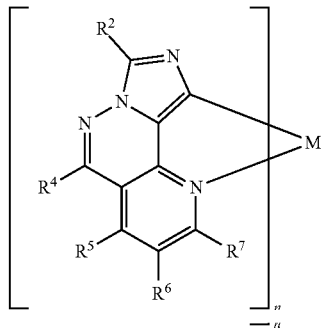
formula (34)
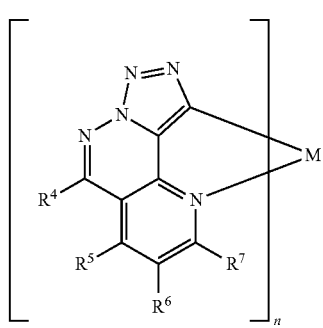
formula (35)
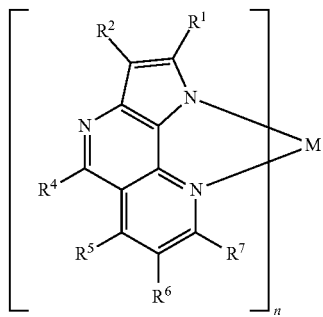
formula (36)

formula (37)
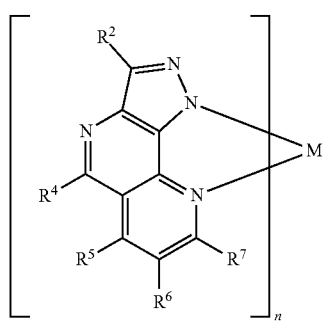
formula (38)
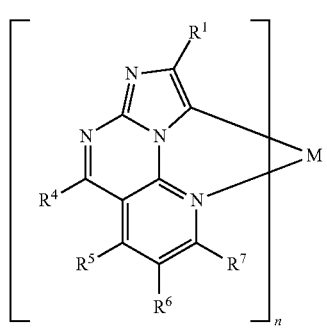
formula (39)
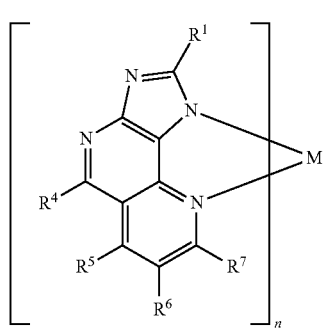
formula (40)
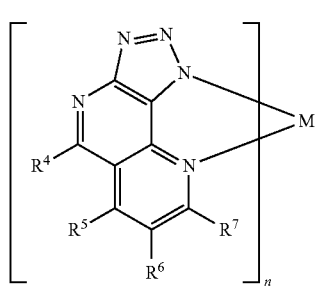
formula (41)
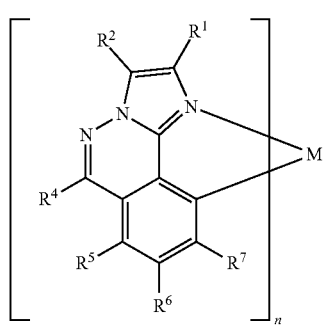
formula (42)
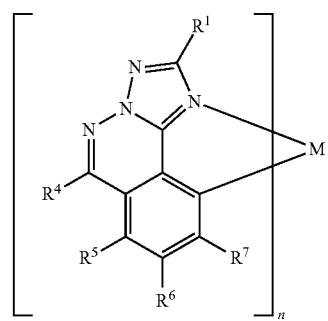
formula (43)
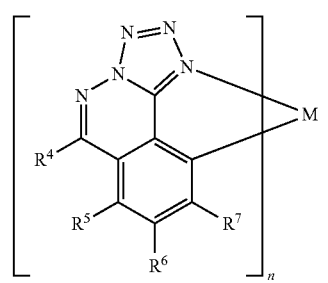
formula (44)
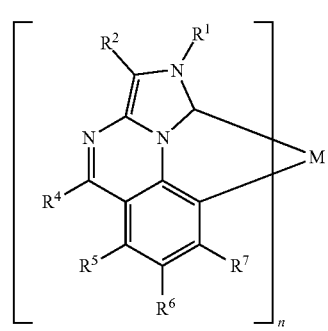
formula (45)
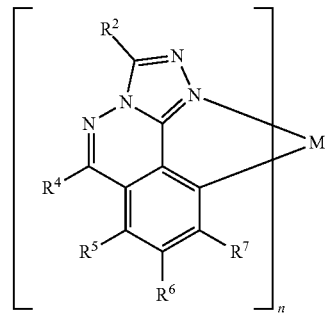
formula (46)
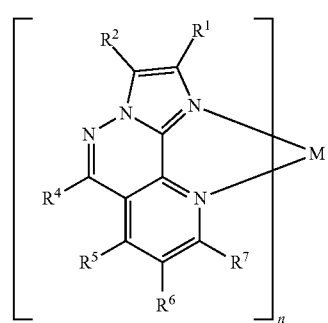

-continued
formula (47)
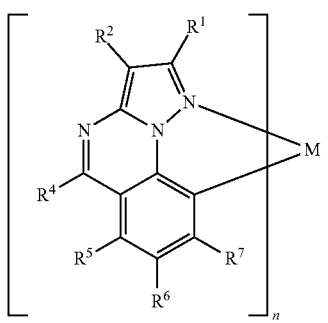
formula (48)
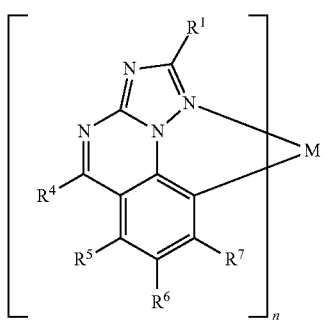
formula (49)
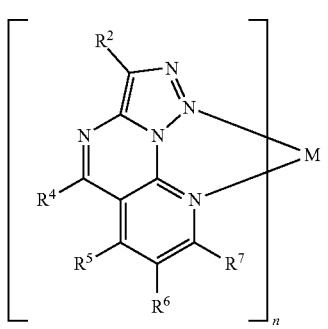
formula (50)
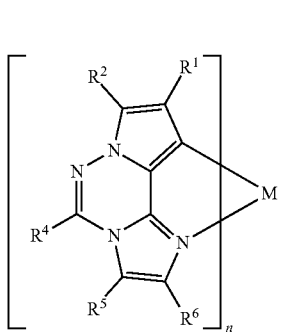
formula (51)
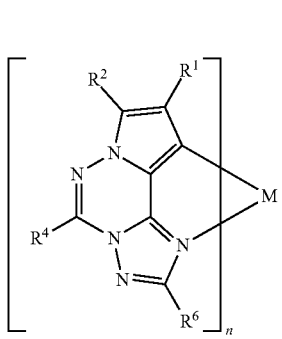
-continued
formula (52)
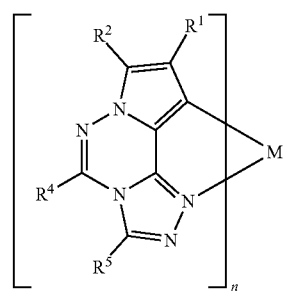
formula (53)
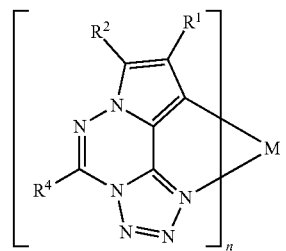
formula (54)
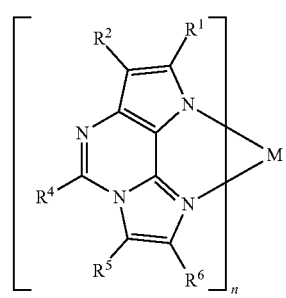
formula (55)
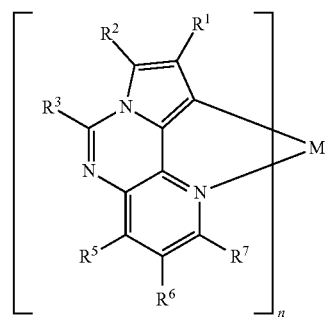
formula (56)
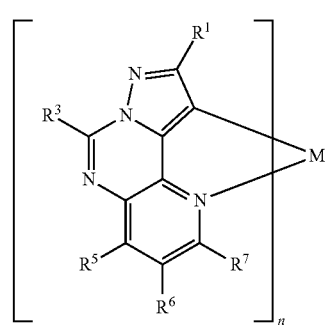

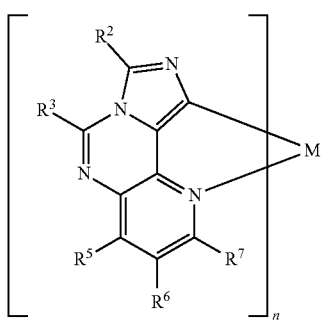
formula (57)
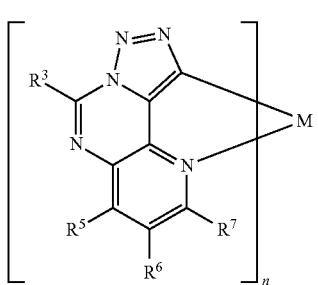
formula (58)
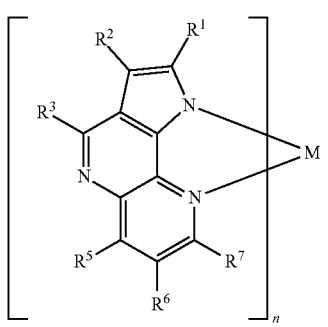
formula (59)
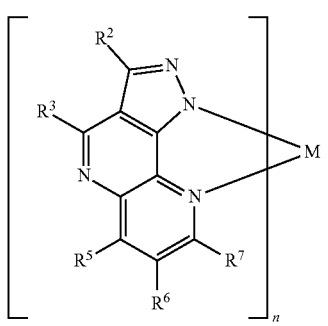
formula (60)
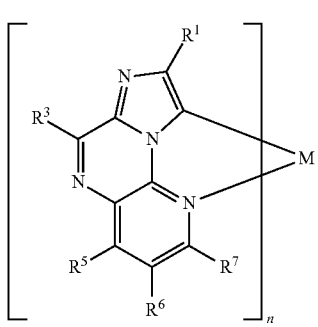
formula (61)
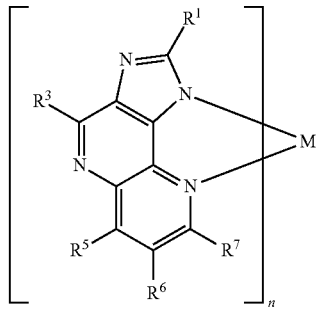
formula (62)
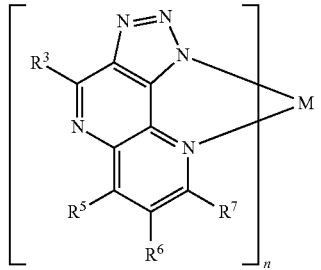
formula (63)
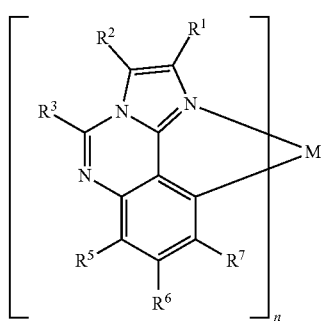
formula (64)
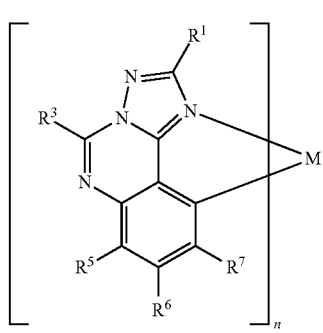
formula (65)
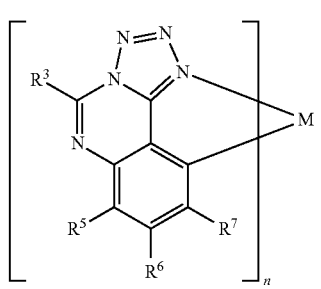
formula (66)

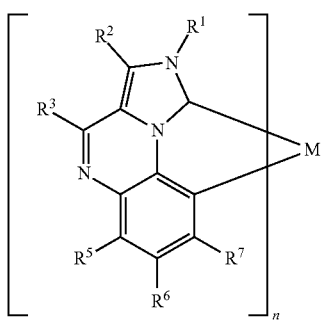
formula (67)
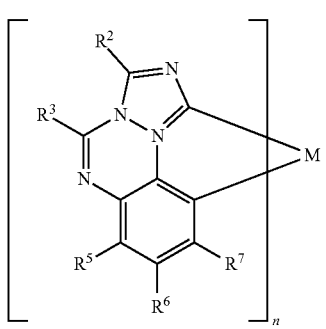
formula (68)
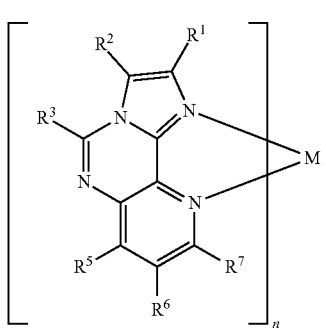
formula (69)
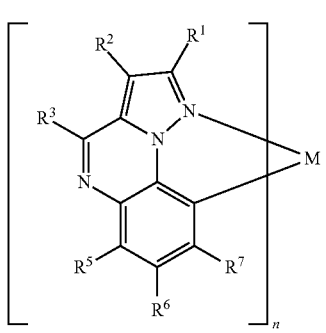
formula (70)
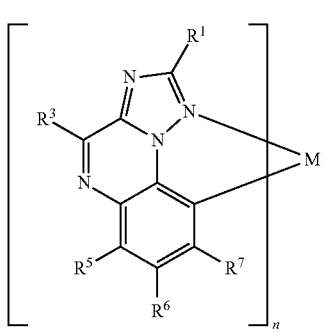
formula (71)
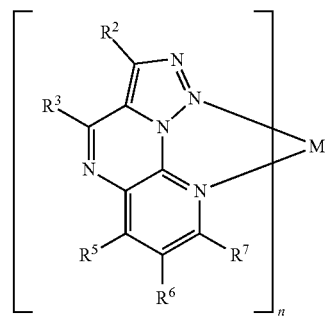
formula (72)
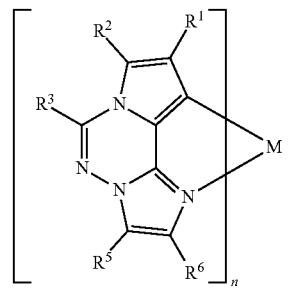
formula (73)
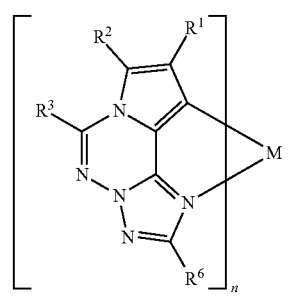
formula (74)
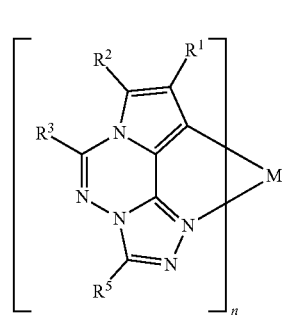
formula (75)
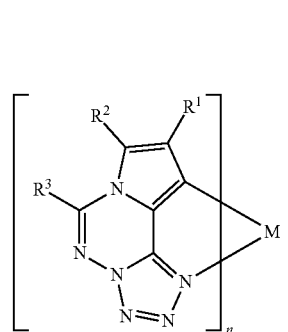
formula (76)

formula (77)

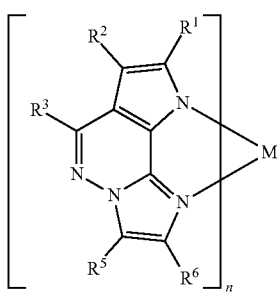

where the symbols and indices used have the meanings indicated above.

In a preferred embodiment of the invention, at least one of the substituents $R^1$, $R^2$, $R^3$ and/or $R^4$, particularly preferably $R^2$, $R^3$ and/or $R^4$, is not equal to hydrogen or deuterium. The substituent $R^2$ is very particularly preferably not equal to hydrogen or deuterium. In a very particularly preferred embodiment of the invention, the substituent $R^2$ is not equal to hydrogen or deuterium and the substituents $R^3$ and $R^4$ are equal to hydrogen or deuterium or the substituent $R^3$ is equal to hydrogen or deuterium and the substituent $R^4$ is not equal to hydrogen or deuterium or the substituent $R^3$ is not equal to hydrogen or deuterium and the substituent $R^4$ is equal to hydrogen or deuterium. This preference is due to the higher stability of the corresponding metal complexes.

Furthermore, larger condensed structures are possible and preferred through ring formation of the substituents. In a preferred embodiment of the invention, the substituents $R^1$ and $R^2$ form an aromatic ring system with one another. Preferred embodiments of such structures are the structures of the following formulae (78) and (79), formula (78)

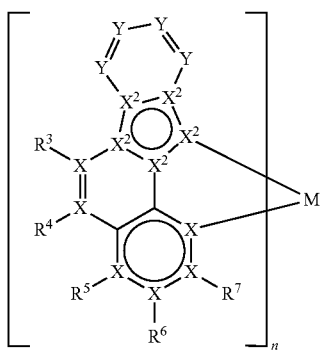

formula (79)

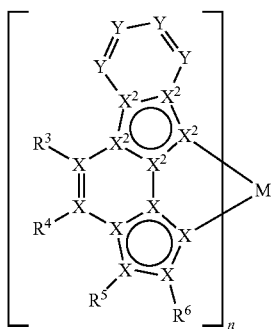

where the symbols and indices used have the meanings given above and furthermore:

Y is, identically or differently on each occurrence, $CR^8$ or N, with the proviso that a maximum of two symbols Y stand for N;

$X^2$ is, identically or differently on each occurrence, C or N, with the proviso that precisely two symbols $X^2$ stand for N and the other symbols $X^2$ stand for C.

Preferred embodiments of the formulae (78) and (79) are the following formulae (78a) to (78d) and (79a) to (79d), formula (78a)

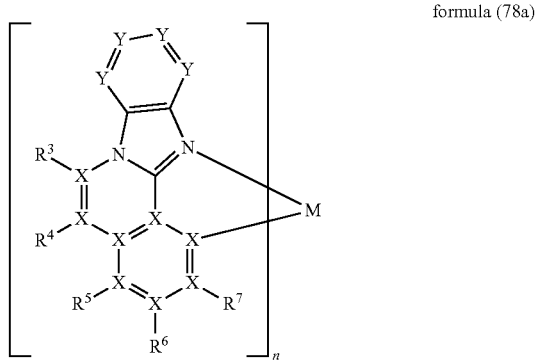

formula (78b)

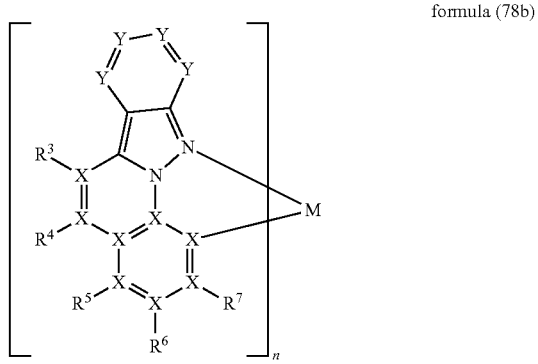

formula (78c)

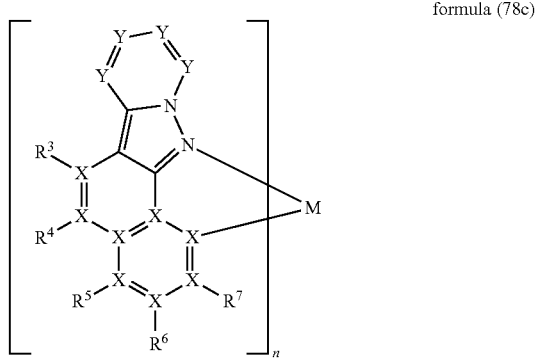

formula (78d)

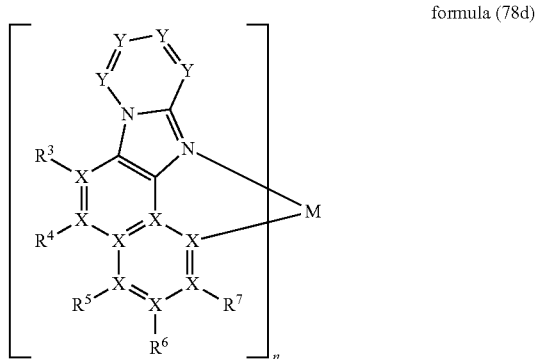

-continued

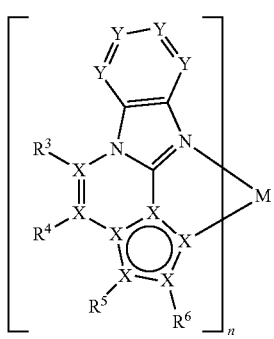
formula (79a)

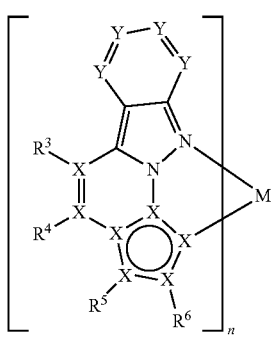
formula (79b)

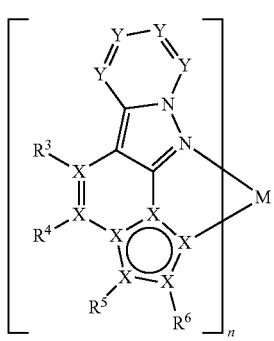
formula (79c)

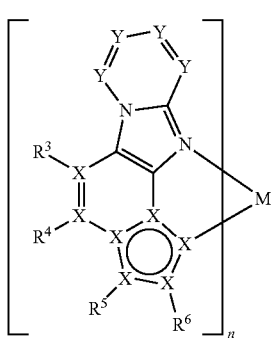
formula (79d)

where the symbols and indices used have the meanings given above.

In a preferred embodiment of the formulae (78a) to (79d), all symbols X stand for C and all symbols Y stand for $CR^8$ or precisely one symbol X or Y stands for N or precisely two of the symbols X or Y stands for N. Particularly preferably, precisely one symbol X or Y or precisely two of the symbols X or Y stand for N.

Particularly preferred embodiments of the formulae (78a) and (79a) are the structures of the following formulae (80) to (85), preferred embodiments of the formulae (78b) are the structures of the following formulae (151) to (157), preferred embodiments of the formulae (78c) are the structures of the following formulae (158) to (164) and preferred embodiments of the formulae (78d) are the structures of the following formulae (165) to (171); preference is furthermore given to the formulae (172) and (173);

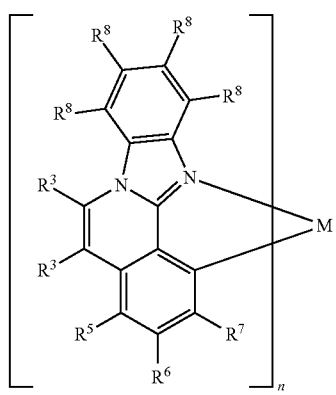
formula (80)

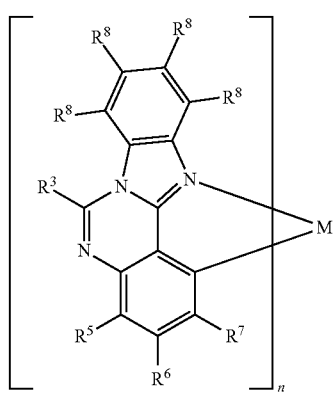
formula (81)

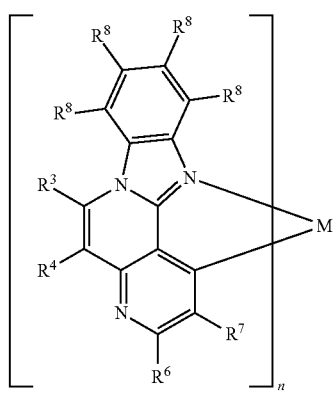
formula (82)

formula (83)
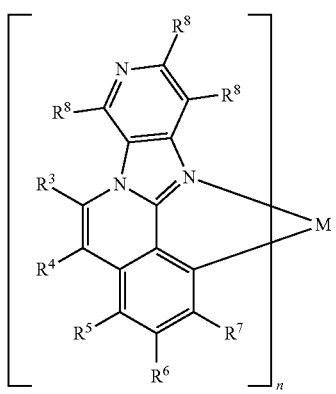
formula (84)
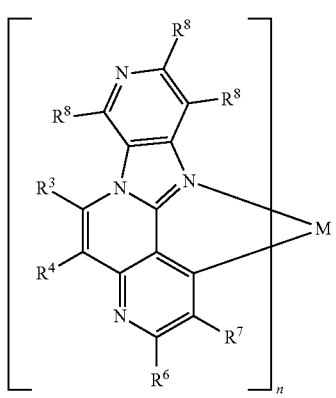
formula (85)
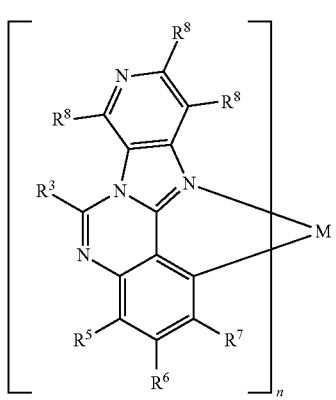
formula (151)
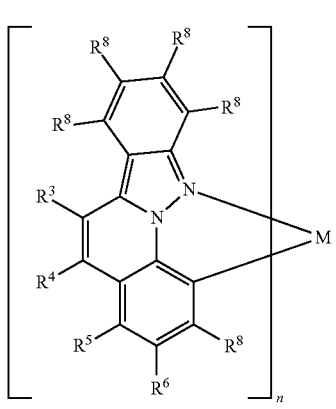
formula (152)
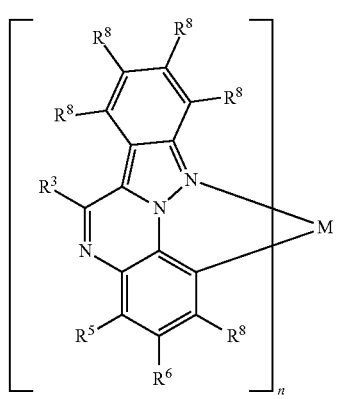
formula (153)
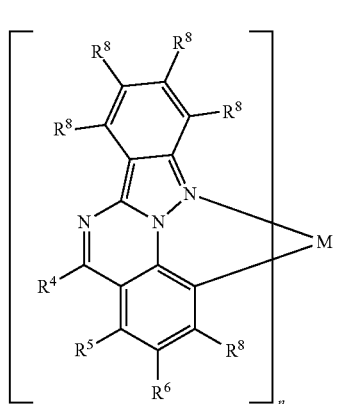
formula (154)
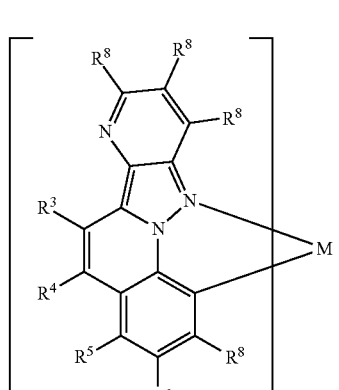
formula (155)

formula (156)
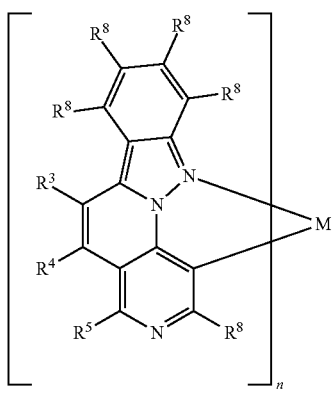
formula (157)
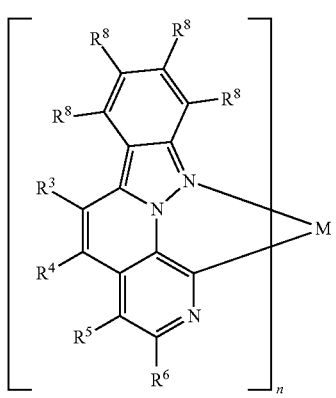
formula (158)
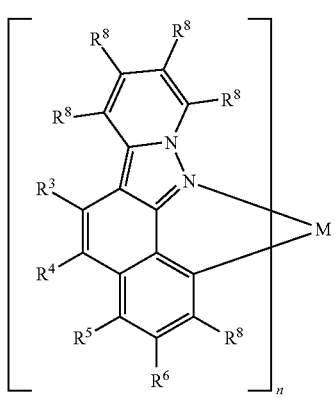
formula (159)
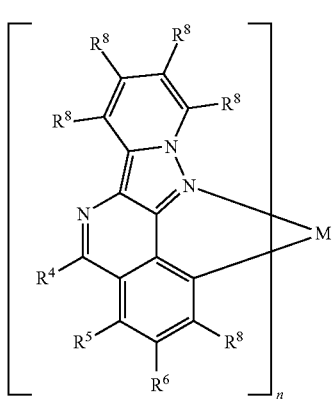
formula (160)
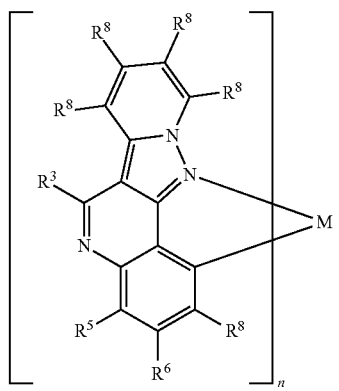
formula (161)
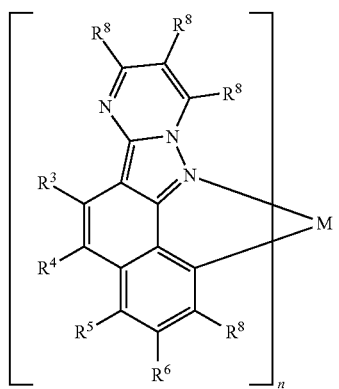
formula (162)
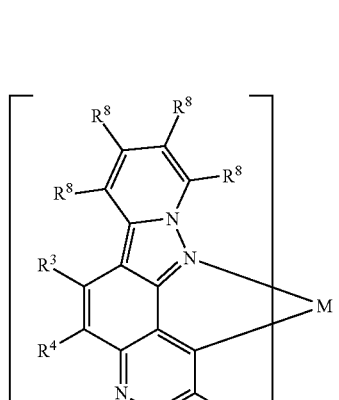
formula (163)
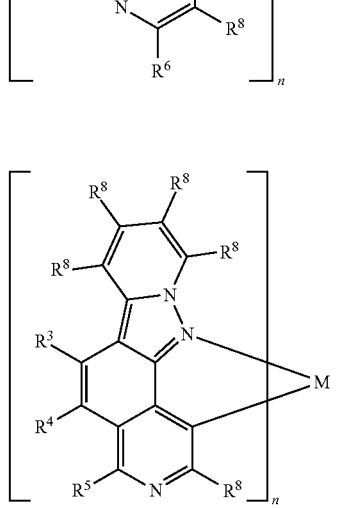

formula (164)
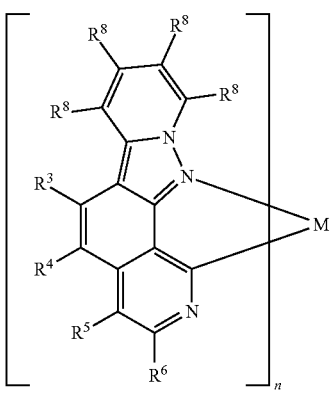
formula (165)
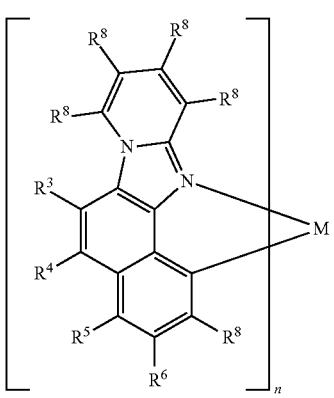
formula (166)
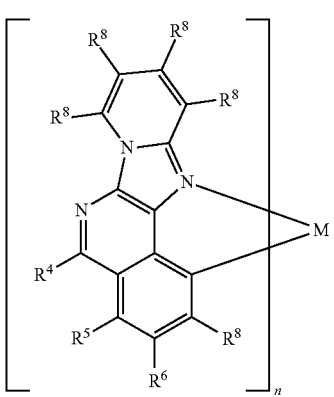
formula (167)
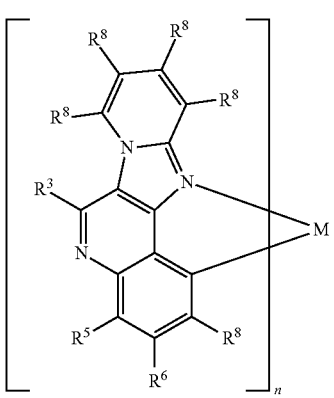
formula (168)
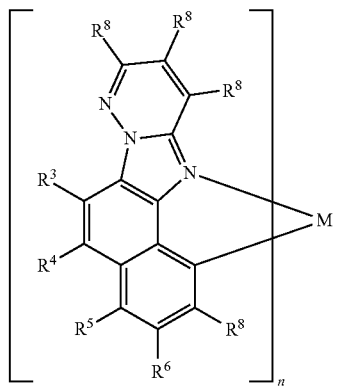
formula (169)
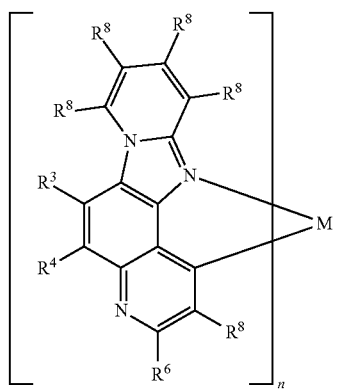
formula (170)
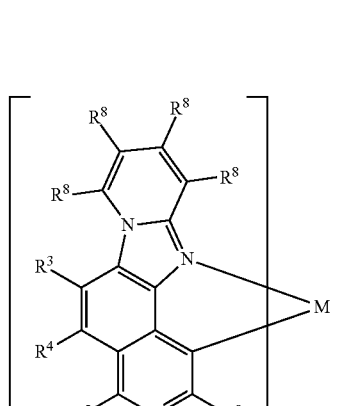
formula (171)
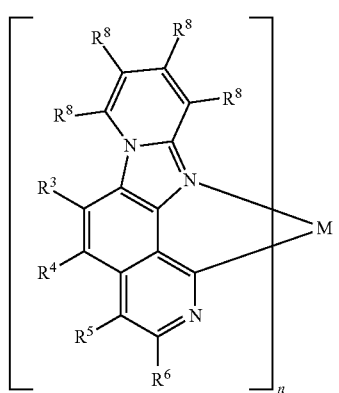

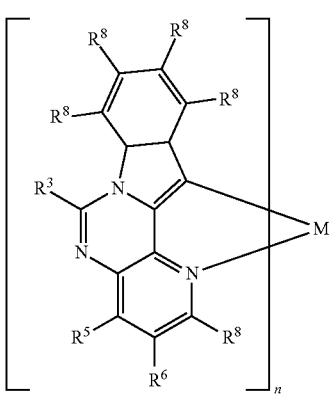

formula (172)

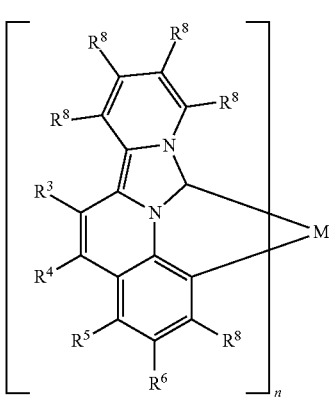

formula (173)

where the symbols and indices used have the meanings given above.

In the structures of the formulae (80) to (85) and (151) to (173), it is preferred for at least one, preferably precisely one, of the substituents which is adjacent to a nitrogen which is only bonded in a six-membered ring to be a substituent other than H or D. These are the radicals $R^3$ or $R^5$ in formula (81), $R^4$ or $R^6$ in formula (82), a radical $R^8$ adjacent to the nitrogen in formula (83), the radicals $R^8$ adjacent to the nitrogen and the radicals $R^4$ or $R^6$ in formula (84) and the radicals $R^8$ adjacent to the nitrogen and the radicals $R^3$ or $R^5$ in formula (85). A corresponding situation applies to the formulae (151) to (173). The same applies to the formulae (78) and (79) or (78a) to (78d) and (79a) to (79d) if at least one of the symbols X or Y stands for N.

In a preferred embodiment of the invention, in each case one of the substituents which is adjacent to a nitrogen which is only bonded in a six-membered ring is on each occurrence, identically or differently, $CF_3$, $OCF_3$, a branched or cyclic alkyl or alkoxy group having 3 to 20 C atoms, which may in each case be substituted by one or more radicals $R^8$, where one or more non-adjacent $CH_2$ groups which are not bonded directly to the aromatic carbon atom of the ligand may be replaced by $R^8C=CR^8$, $C\equiv C$, $Si(R^8)_2$, $C=O$, $NR^8$, O, S or $CONR^8$ and where one or more H atoms may be replaced by D, F, Cl, Br, I or CN, or $Si(R^8)_3$, where $R^8$ is other than H or D, a dialkylamino group, where the alkyl groups each have 1 to 10 C atoms and may be linear, branched or cyclic, or an aromatic or heteroaromatic ring system having 5 to 60 aromatic ring atoms, which may in each case be substituted by one or more radicals $R^8$, or an aralkyl or heteroaralkyl group having 5 to 40 aromatic ring atoms, which may be substituted by one or more radicals $R^8$.

It is furthermore possible for the substituent $R^7$ in formula (2) or the substituent $R^6$ in formula (3) which is in the ortho-position to the metal coordination to represent a coordinating group which likewise coordinates to the metal M. Preferred coordinating groups $R^6$ or $R^7$ are aryl and heteroaryl groups, for example phenyl or pyridyl, aryl or alkyl cyanides, aryl or alkyl-isocyanides, amines or amides, alcohols or alcoholates, thioalcohols or thioalcoholates, phosphines, phosphites, carbonyl functions, carboxylates, carbamides or aryl- or alkylacetylides. The moieties ML of the following formulae (86) to (93), for example, are accessible here:

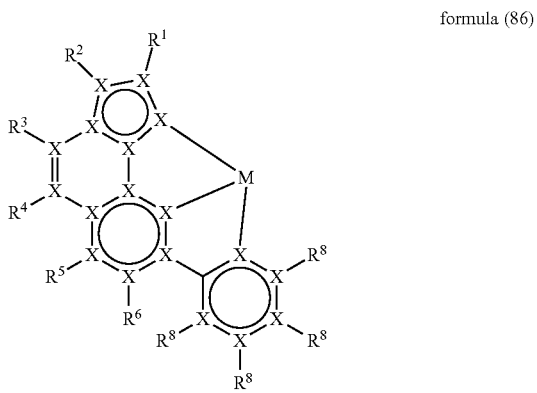

formula (86)

formula (87)

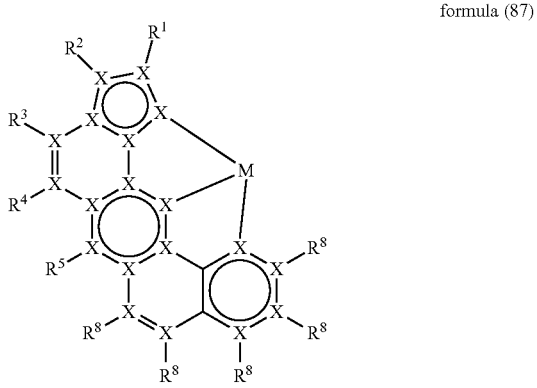

formula (88)

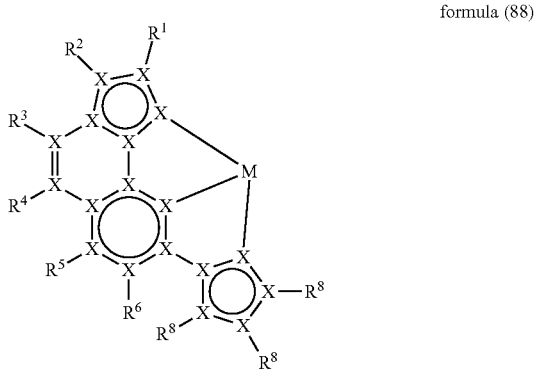

formula (89)

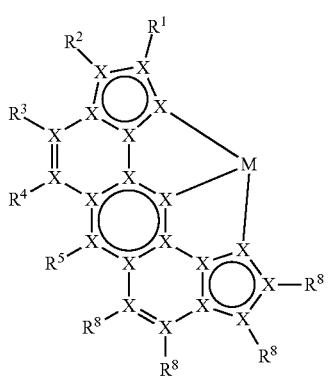

formula (90)

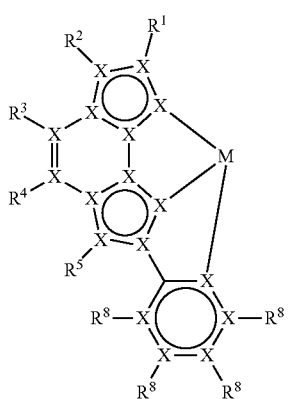

formula (91)

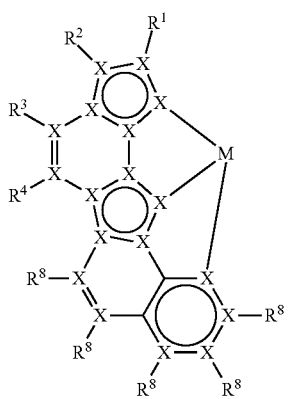

formula (92)

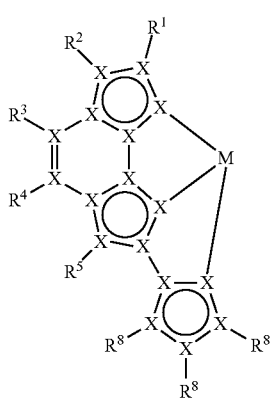

formula (93)

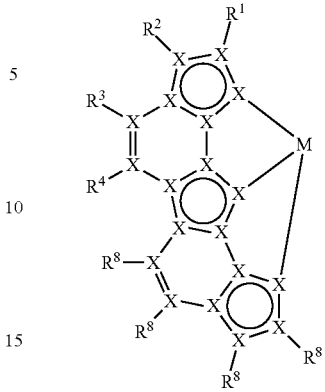

where the symbols used have the meanings given above. The preferences given above apply to the ligands.

The formulae (86) to (93) show merely by way of example how the substituent $R^6$ or $R^7$ can additionally coordinate to the metal. Other groups $R^6$ and $R^7$ which coordinate to the metal are also possible entirely analogously without further inventive step.

As described above, a single bond or a bridging unit V which links this ligand L to one or more further ligands L or L' may also be present instead of one of the radicals $R^1$ to $R^7$. In a preferred embodiment of the invention, a bridging unit V is present instead of one of the radicals $R^1$ to $R^7$, in particular instead of $R^1$, $R^2$, $R^6$ or $R^7$, so that the ligands have a tridentate or polydentate or polypodal character. Formula (2) preferably contains a bridging unit V instead of $R^1$ or $R^7$ and formula (3) preferably contains a bridging unit V instead of $R^1$ or $R^6$. It is also possible for two such bridging units V to be present. This results in the formation of macrocyclic ligands or in the formation of cryptates.

Preferred structures containing polydentate ligands are the metal complexes of the following formulae (94) to (101):

formula (94)

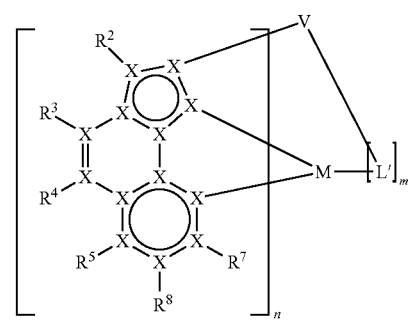

formula (95)

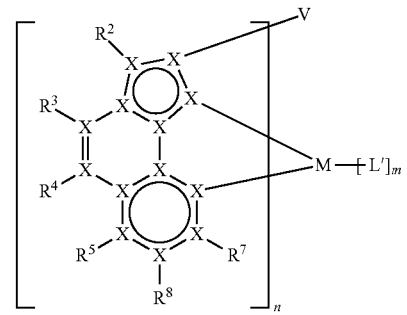

formula (96)
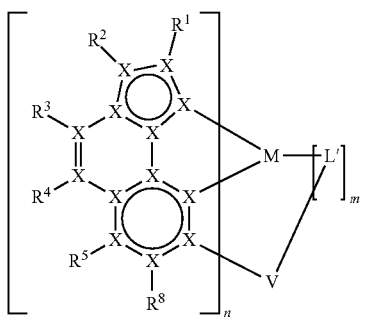

formula (97)
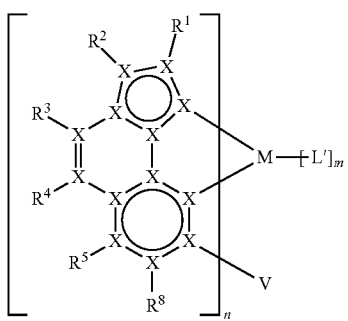

formula (98)
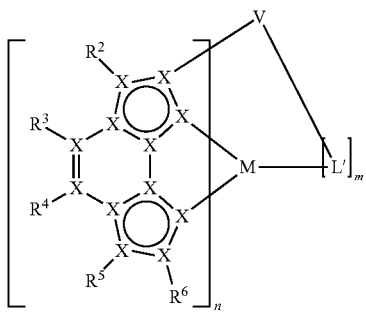

formula (99)
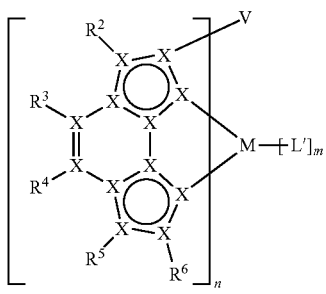

formula (100)
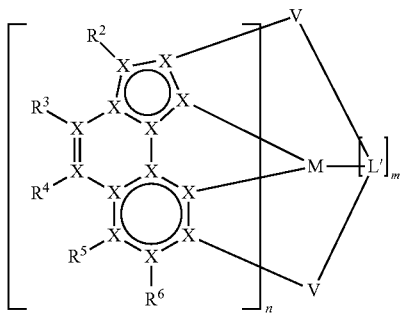

formula (101)
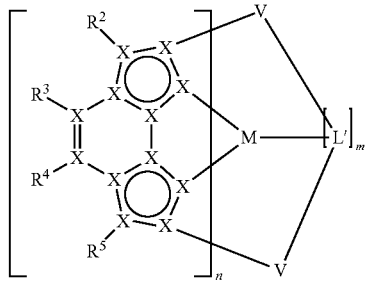

where the symbols used have the meanings given above, and V preferably represents a single bond or a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or covalently bonds L to L'. The bridging unit V here may also be substituted by the above-mentioned groups $R^8$. It may furthermore also have an asymmetrical structure, i.e. the linking of V to L and L' need not be identical. The bridging unit V can be neutral, singly, doubly or triply negatively charged or singly, doubly or triply positively charged. V is preferably neutral or singly negatively charged or singly positively charged. The charge of V is preferably selected so that overall a neutral complex forms. The preferences given above for the moiety $ML_n$ apply to the ligands.

The precise structure and chemical composition of the group V do not have a significant influence on the electronic properties of the complex since it is, in particular, the task of this group to increase the chemical and thermal stability of the complexes by bridging L to one another or to L'.

If V is a trivalent group, i.e. bridges three ligands L to one another or two ligands L to L' or one ligand L to two ligands L', V is preferably selected, identically or differently on each occurrence, from the group consisting of B, $B(R^8)^-$, $B(C(R^8)_2)_3$, $(R^8)B(C(R^8)_2)_3^-$, $B(O)_3$, $(R^8)B(O)_3^-$, $B(C(R^8)_2C(R^8)_2)_3$, $(R^8)B(C(R^8)_2C(R^8)_2)_3^-$, $B(C(R^8)_2O)_3$, $(R^8)B(C(R^8)_2 O)_3^-$, $B(OC(R^8)_2)_3$, $(R^8)B(OC(R^8)_2)_3^-$, $C(R^8)$, $CO^-$, $CN(R^8)_2$, $(R^8)C(C(R^8)_2)_3$, $(R^8)C(O)_3$, $(R^8)C(C(R^8)_2C(R^8)_2)_3$, $(R^8)C(C(R^8)_2O)_3$, $(R^8)C(OC(R^8)_2)_3$, $(R^8)C(Si(R^8)_2)_3$, $(R^8)C(Si(R^8)_2C(R^8)_2)_3$, $(R^8)C(C(R^8)_2Si(R^8)_2)_3$, $(R^8)C(Si(R^8)_2Si(R^8)_2)_3$, $Si(R^8)$, $(R^8)Si(C(R^8)_2)_3$, $(R^8)Si(O)_3$, $(R^8)Si(C(R^8)_2C(R^8)_2)_3$, $(R^8)Si(OC(R^8)_2)_3$, $(R^8)Si(C(R^8)_2O)_3$, $(R^8)Si(Si(R^8)_2)_3$, $(R^8)Si(Si(R^8)_2C(R^8)_2)_3$, $(R^8)Si(C(R^8)_2Si(R^8)_2)_3$, $(R^8)Si(Si(R^8)_2Si(R^8)_2)_3$, N, NO, $N(R^8)^+$, $N(C(R^8)_2)_3$, $(R^8)N(C(R^8)_2)_3^+$, $N(C=O)_3$, $N(C(R^8)_2C(R^8)_2)_3$, $(R^8)N(C(R^8)_2C(R^8)_2)_2^+$, P, $P(R^8)^+$, PO, PS, PSe, PTe, $P(O)_3$, $PO(O)_3$, $P(OC(R^8)_2)_3$, $PO(OC(R^8)_2)_3$, $P(C(R^8)_2)_3$, $P(R^8)(C(R^8)_2)_3^+$, $PO(C(R^8)_2)_3$, $P(C(R^8)_2C(R^8)_2)_3$, $P(R^8)(C(R^8)_2C(R^8)_2)_3^+$, $PO(C(R^8)_2C(R^8)_2)_3$, $S^+$, $S(C(R^8)_2)_3^+$, $S(C(R^8)_2C(R^8)_2)_3^+$, or a unit of the formula (102), (103), (104) or (105), formula (102)
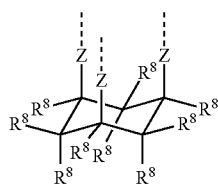

formula (103)

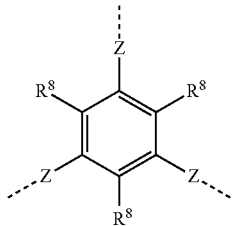

formula (104)

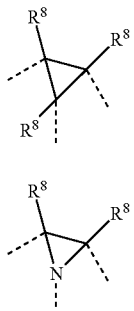

formula (105)

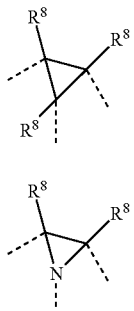

where the dashed bonds in each case indicate the bond to the part-ligands L or L', and Z is selected, identically or differently on each occurrence, from the group consisting of a single bond, O, S, S(═O), S(═O)$_2$, NR$^8$, PR$^8$, P(═O)R$^8$, P(═NR$^8$), C(R$^8$)$_2$, C(═O), C(═NR$^8$), C(═C(R$^8$)$_2$), Si(R$^8$)$_2$ and BR$^8$. The other symbols used have the meanings given above.

If V is a divalent group, i.e. bridges two ligands L to one another or one ligand L to L', V is preferably selected, identically or differently on each occurrence, from the group consisting of BR$^8$, B(R$^8$)$_2^-$, C(R$^8$)$_2$, C(═O), Si(R$^8$)$_2$, NR$^8$, PR$^8$, P(R$^8$)$_2^+$, P(═O)(R$^8$), P(═S)(R$^8$), AsR$^8$, As(═O)(R$^8$), As(═S)(R$^8$), O, S, Se, or a unit of the formulae (106) to (115), formula (106)

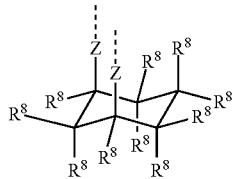

formula (107)

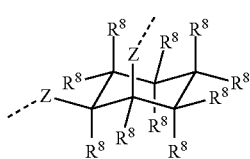

formula (108)

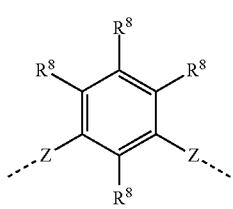

formula (109)

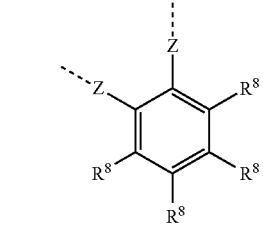

formula (110)

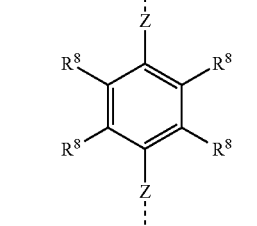

formula (111)

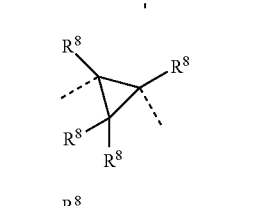

formula (112)

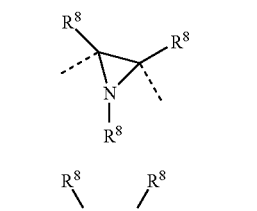

formula (113)

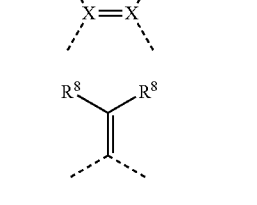

formula (114)

formula (115)

where the dashed bonds in each case indicate the bond to the part-ligands L or L', Y stands on each occurrence, identically or differently, for C(R$^8$)$_2$, N(R$^8$), O or S, and the other symbols used each have the meanings mentioned above.

Preferred ligands L' as occur in formula (1) are described below. The ligand groups L' can also be selected correspondingly if they are bonded to L via a bridging unit V, as indicated in formulae (94) to (101).

The ligands L' are preferably neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' can also be bonded to L via a bridging group V.

Furthermore, the ligands L' may also have one or more polymerisable groups PG.

Preferred neutral, monodentate ligands L' are selected from the group consisting of carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris-(pentafluorophenyl)phosphine, dimethylphenylphosphine, methyldiphenylphosphine, bis(tert-butyl) phenylphosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides F−, Cl−, Br− and I−, alkylacetylides, such as, for example, methyl-C≡C−, tert-butyl-C≡C−, arylacetylides, such as, for example, phenyl-C≡C−, cyanide, cyanate, isocyanate, thiocyanate, isothiocyanate, aliphatic or aromatic alcoholates, such as, for example, methanolate, ethanolate, propanolate, iso-propanolate, tert-butylate, phenolate, aliphatic or aromatic thioalcoholates, such as, for example, methanethiolate, ethanethiolate, propanethiolate, iso-propanethiolate, tert-thiobutylate, thiophenolate, amides, such as, for example, dimethylamide, diethylamide, di-iso-propylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are defined as above.

Preferred di- or trianionic ligands are $O^{2-}$, $S^{2-}$, carbides, which result in coordination in the form R—C≡M, and nitrenes, which result in coordination in the form R—N=M, where R generally stands for a substituent, or $N^{3-}$.

Preferred neutral or mono- or dianionic bidentate or polydentate ligands L' are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-di-iso-propylphenylimino)ethyl]pyridine, 2-[1-(methylimino)ethyl]-pyridine, 2-[1-(ethylimino)ethyl]pyridine, 2-[1-(iso-propylimino) ethyl]pyridine, 2-[1-(tert-butylimino)ethyl]pyridine, diimines, such as, for example, 1,2-bis(methylimino)ethane, 1,2-bis(ethylimino)ethane, 1,2-bis(iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tert-butylimino)butane, 1,2-bis(phenylimino)ethane, 1,2-bis(2-methylphenylimino)ethane, 1,2-bis(2,6-di-iso-propylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-di-iso-propylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis (diphenylphosphino)methane, bis(diphenylphosphino) ethane, bis(diphenylphosphino)propane, bis(diphenylphosphino)butane, bis(dimethylphosphino)methane, bis (dimethylphosphino)ethane, bis(dimethylphosphino) propane, bis(diethylphosphino)-methane, bis (diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)-methane, 2,2,6, 6-tetramethyl-3,5-heptanedione, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl)borate and tetrakis(1-pyrazolyl)borate.

Preference is furthermore given to bidentate monoanionic, neutral or dianionic ligands L', in particular monoanionic ligands, which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals $R^1$ to $R^6$. A multiplicity of such ligands is known to the person skilled in the art in the area of phosphorescent electroluminescent devices, and he will be able, without inventive step, to select further ligands of this type as ligand L' for compounds of the formula (1). The combination of two groups as depicted by the following formulae (116) to (143) is generally particularly suitable for this purpose, where one group is preferably bonded via a neutral nitrogen atom or a carbene atom and the other group is preferably bonded via a negatively charged carbon atom or a negatively charged nitrogen atom. The ligand L' can then be formed from the groups of the formulae (116) to (143) through these groups bonding to one another in each case at the position denoted by #. The position at which the groups coordinate to the metal is denoted by *. These groups may also be bonded to the ligand L via one or two bridging units V.

formula (116)

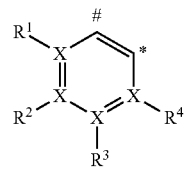

formula (117)
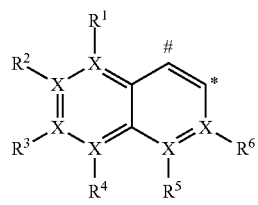
formula (118)
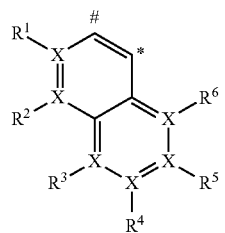
formula (119)
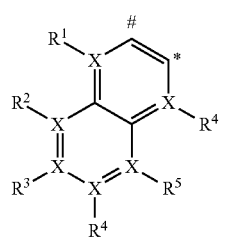
formula (120)
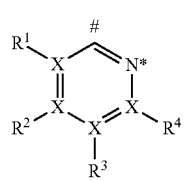
formula (121)
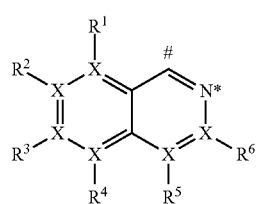
formula (122)
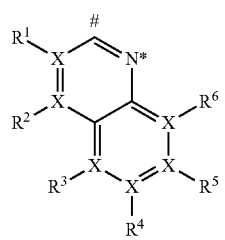
formula (123)
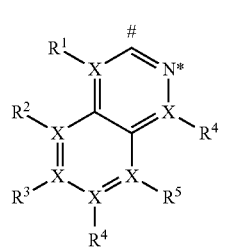
formula (124)
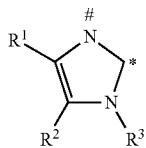
formula (125)
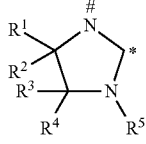
formula (126)
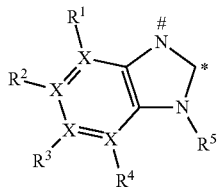
formula (127)
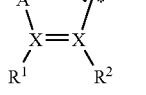
formula (128)
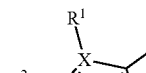
formula (129)
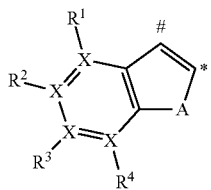
formula (130)
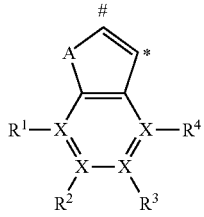
formula (131)
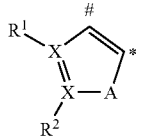
formula (132)
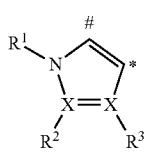

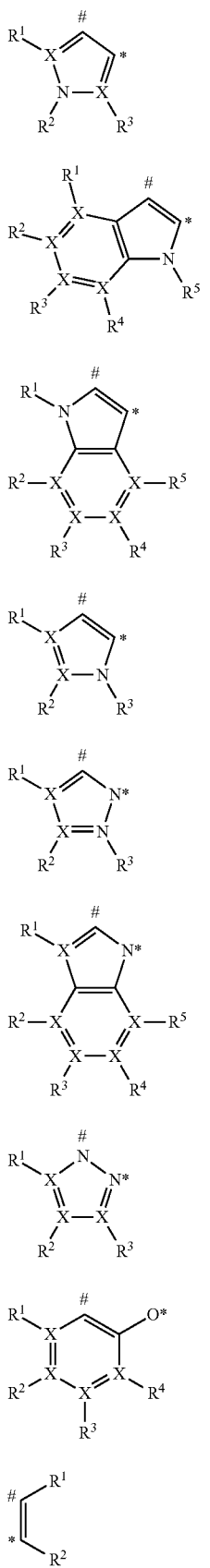

The symbols used here have the same meaning as described above, where $R^3$ and $R^4$ here may also form an aromatic ring system with one another, and preferably a maximum of three symbols X in each group stand for N, particularly preferably a maximum of two symbols X in each group stand for N, very particularly preferably a maximum of one symbol X in each group stands for N, especially preferably all symbols X stand for C. Furthermore, A stands for O or S.

Likewise preferred ligands L' are $\eta^5$-cyclopentadienyl, $\eta^5$-pentamethylcyclopentadienyl, $\eta^6$-benzene or $\eta^7$-cycloheptatrienyl, each of which may be substituted by one or more radicals $R^1$.

Likewise preferred ligands L' are 1,3,5-cis,cis-cyclohexane derivatives, in particular of the formula (144), 1,1,1-tri(methylene)methane derivatives, in particular of the formula (145), and 1,1,1-trisubstituted methanes, in particular of the formulae (146) and (147):

where the coordination to the metal M is shown in each of the formulae, $R^1$ has the meaning given above, and A stands, identically or differently on each occurrence, for $O^-$, $S^-$, $COO^-$, $P(R^1)_2$ or $N(R^1)_2$.

Preferred radicals $R^1$ to $R^7$ in the structures shown above are selected on each occurrence, identically or differently, from the group consisting of a polymerisable group PG or H, D, F, Br, $N(R^8)_2$, CN, $B(OR^8)_2$, $C(=O)R^8$, $P(=O)(R^8)_2$, a straight-chain alkyl group having 1 to 10 C atoms or an alkenyl or alkynyl group having 2 to 10 C atoms or a branched or cyclic alkyl group having 3 to 10 C atoms, each of which may be substituted by one or more radicals $R^8$, where one or more H atoms may be replaced by D or F, or an aromatic or heteroaromatic ring system having 5 to 14 aromatic ring atoms, which may in each case be substituted by one or more radicals $R^8$; $R^1$ and $R^2$ and/or $R^2$ and $R^3$ and/or $R^4$ and $R^5$ and/or $R^5$ and $R^6$ and/or $R^6$ and $R^7$ here may also form a mono- or polycyclic, aliphatic, aromatic and/or benzo-fused ring system with one another; furthermore, $R^3$ and $R^4$ may form a mono- or polycyclic, aliphatic ring system with one another. Particularly preferred radicals $R^1$ to $R^7$ are selected on each occurrence, identically or differently, from the group consisting of H, D, F, Br, CN, $B(OR^8)_2$, a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms, which may in each case be substituted by one or more radicals $R^8$; $R^1$ and $R^2$ and/or $R^2$ and $R^3$ and/or $R^4$ and $R^5$ and/or $R^5$ and $R^6$ and/or $R^6$ and $R^7$ here may also form a mono- or polycyclic, aliphatic, aromatic and/or benzo-fused ring system with one another; furthermore, $R^3$ and $R^4$ may form a mono- or polycyclic, aliphatic ring system with one another and may also form an aromatic ring system in formulae (116) to (143). Furthermore, preferred radicals which are adjacent to the nitrogen in the structures of the formulae (78) to (85) have already been mentioned in detail above.

The complexes according to the invention may be facial or pseudofacial or they may be meridional or pseudomeridional. Chiral complexes may thus also arise. The substituents $R^1$ to $R^8$ may also, depending on the precise structure, have one or more stereocentres. The formation of diastereomers is thus possible. The complexes according to the invention then encompass both the mixtures of the various diastereomers or the corresponding racemates and also the individual isolated diastereomers or enantiomers.

The preferred embodiments mentioned above can be combined with one another as desired. In a particularly preferred embodiment of the invention, the preferred embodiments mentioned above apply simultaneously.

As described above, at least one of the substituents $R^1$ to $R^7$ and/or one of the substituents on L' stands for a polymerisable group PG. If one or more of the radicals $R^1$ to $R^7$ as polymerisable group PG are selected from an alkenyl or an alkynyl group, this is a terminal alkenyl or alkynyl group having 3 to 40 C atoms, where individual $CH_2$ groups may also be replaced by the above-mentioned groups. If one or more of the radicals $R^1$ to $R^7$ as polymerisable group PG is selected from a group $Si(R^8)_3$, $R^8$ stands either for Cl or for an alkoxy group having 1 to 40 C atoms. Furthermore, the polymerisable group PG is not selected from Cl, Br, I or $B(OR^8)_2$. If the polymerisable group PG stands for $N(R^8)_2$, one radical $R^8$ is equal to H and the other radical $R^8$ is preferably not equal to H or D.

The precise structure of the polymerisable group PG has no significant influence on the properties of the complex. The job of this group is, in particular, to link the complexes to one another, optionally to further monomers, by a polymerisation reaction and thus to result in polymers or optionally in crosslinked layers.

A polymerisable group in the sense of the present invention is a functional group which is capable of reacting irreversibly or essentially irreversibly under the selected reaction conditions and thus forming a polymeric material, which may be soluble or also, for example through crosslinking, insoluble. A polymeric material in the sense of the present invention is also taken to mean an oligomeric or dendrimeric material. The reaction can be a polymerisation reaction in the classical sense, i.e. a chain reaction in which a polymer is formed, but also, for example, a polycondensation reaction, a polycycloaddition or a metathesis reaction. For a polycondensation reaction or for a polycycloaddition, it is necessary, for the incorporation of the compound of the formula (1), for at least two polymerisable groups to be present in the compound of the formula (1). If a polymerisation is described below, this means all types of reaction which result in a polymer. The polymerisation can generally be supported by heat and/or by UV, microwave, X-ray or electron radiation and/or through the use of free-radical formers, anions, cations, acids and/or photoacids. The presence of a further monomer which reacts with the polymerisable groups of the compound of the formula (1) may also be necessary for the polycondensation or for the polycycloaddition. Thus, for example, carboxylic acid groups can react with amino groups to form polyamides or with alcohols to form polyesters. The presence of catalysts may likewise be sensible or necessary, for example for the metathesis reaction.

Examples of polymerisable groups PG which are preferred in accordance with the invention are the units mentioned below.

A) Alkenyl or Alkynyl Groups:

Alkenyl or alkynyl groups having 2 to 40 C atoms, preferably having 2 to 10 C atoms, where, in addition, individual $CH_2$ groups and/or individual H atoms may be replaced by the groups mentioned above in the case of $R^1$ to $R^7$, are suitable. If one or more of the groups $R^1$ to $R^7$ are selected as polymerisable alkenyl or alkynyl group, they are alkenyl groups having 3 to 40 C atoms, preferably having 3 to 10 C atoms, which carry a terminal double bond, or alkynyl groups having 3 to 40 C atoms, preferably having 3 to 10 C atoms, which carry a terminal triple bond. Individual $CH_2$ groups in the terminal alkenyl or alkynyl groups may also be replaced here by the groups mentioned above in the case of $R^1$ to $R^7$.

Preferred polymerisable groups PG encompass vinyl, propenyl, butenyl, $C_{4-20}$-cycloalkenyl and ethynyl. Thus, for example, the groups mentioned below are suitable, where the link to the complex is indicated in each of these groups by R and these groups may each be substituted by one or more radicals $R^8$:

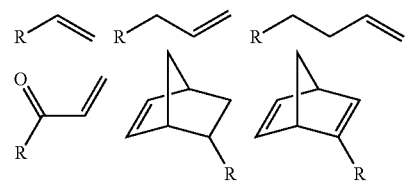

Furthermore, styryl groups in the broadest sense are suitable in this class of polymerisable groups. A styryl group in the sense of the present application are is taken to mean an aryl or heteroaryl group which is substituted by a vinyl group and which may also carry one or more further radicals. Thus, for example, the groups mentioned below are suitable, where the link to the complex is indicated in each of these groups by R and these groups may each be substituted by one or more radicals $R^8$:

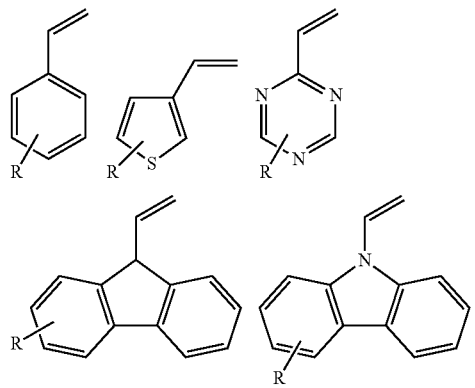

Furthermore, acrylic acid derivatives in the broadest sense, in particular acrylates, acrylamides, methacrylates and methacrylamides, are suitable in this class of polymerisable groups. Particular preference is given to $C_{1-10}$-alkyl acrylate and $C_{1-10}$-alkyl methacrylate. Thus, for example, the groups mentioned below are suitable, where the link to the complex is indicated in each of these groups by R and these groups may each be substituted by one or more radicals $R^8$:

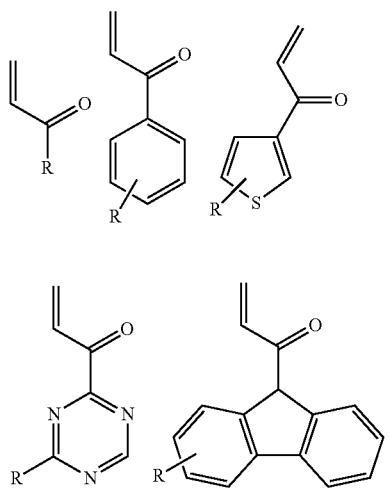

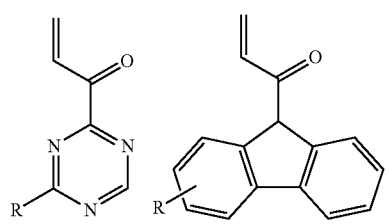

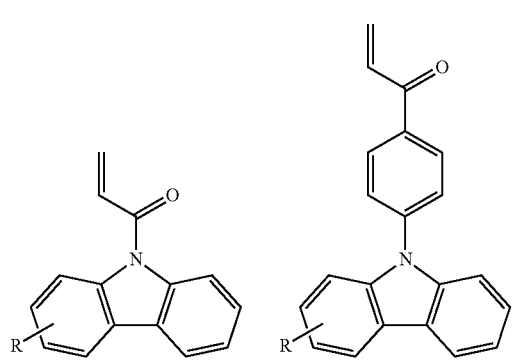

-continued

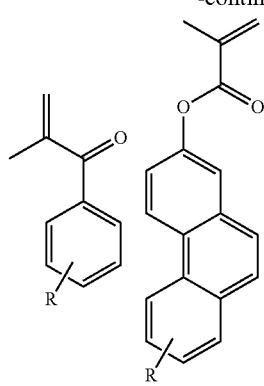

Furthermore, alkenyloxy or perfluoroalkenyloxy derivatives, in particular ethenyleneoxy or perfluoroethenyleneoxy, are suitable in this class of polymerisable groups. Thus, for example, the groups mentioned below are suitable, where the link to the complex is indicated in each of these groups by R and these groups may each be substituted by one or more radicals $R^8$:

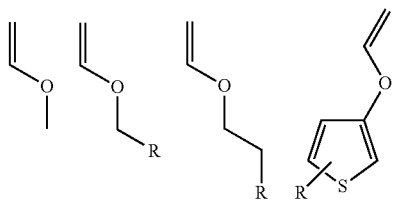

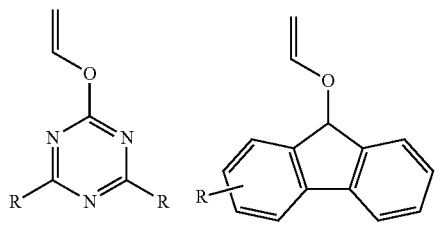

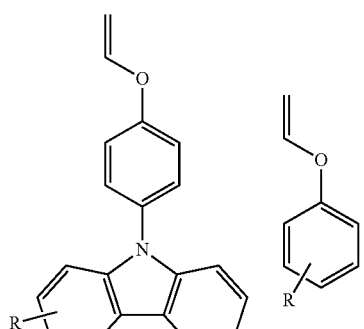

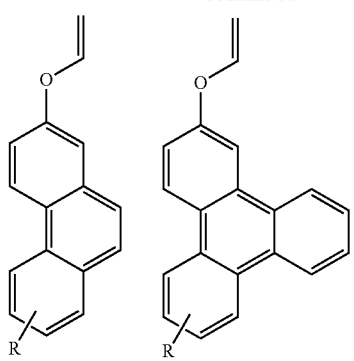

The polymerisation reaction of the above-mentioned groups can take place by a free-radical, cationic or anionic mechanism. It may be appropriate to add a corresponding initiator for the polymerisation reaction.

Suitable initiators for free-radical polymerisation are, for example, dibenzoyl peroxide, AIBN or TEMPO. Suitable initiators for cationic polymerisation are, for example, AlCl$_3$, BF$_3$, triphenylmethyl perchlorate, tropylium hexachloroantimonate, etc. Suitable initiators for anionic polymerisation are bases, in particular butyllithium.

B) Oxetanes and Oxiranes

A further suitable class of polymerisable groups are oxetanes and oxiranes, which polymerise cationically by ring opening. Thus, for example, the groups mentioned below are suitable, where the link to the complex is indicated in each of these groups by R and these groups may each be substituted by one or more radicals R$^8$:

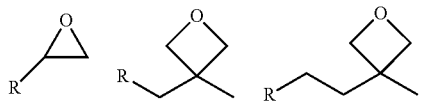

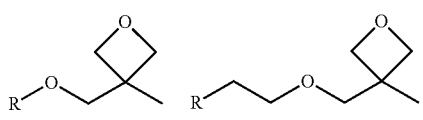

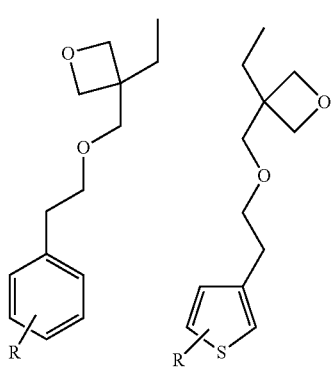

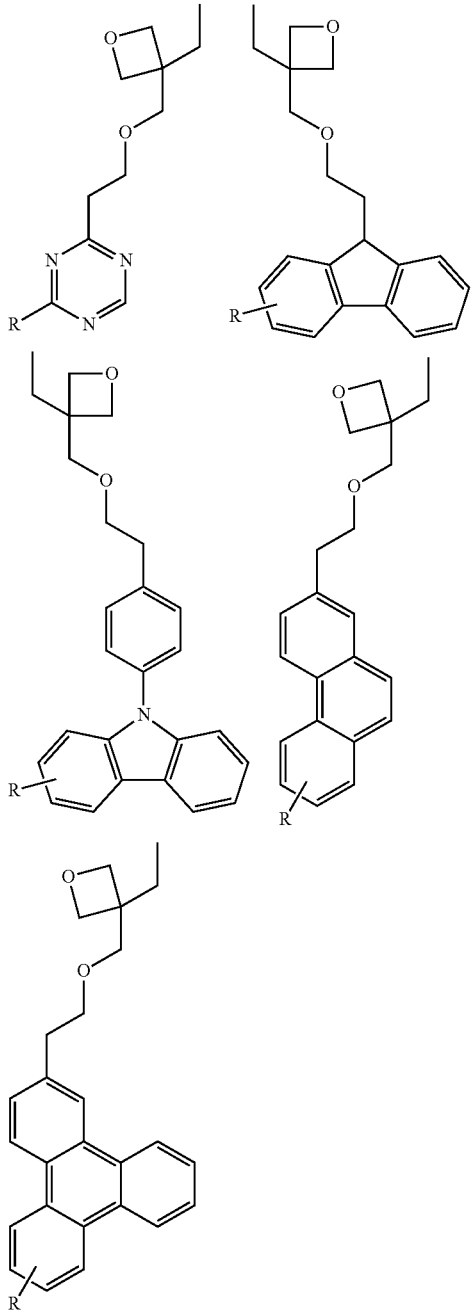

Thus, for example, it is also possible to link oxetane groups to an acetylacetonate co-ligand, so that the co-ligand L' in the complex has a polymerisable group PG of this type. An example of a co-ligand L' of this type is the following structure:

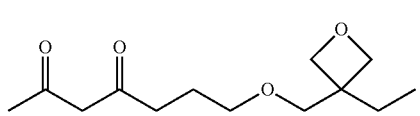 [SMILES: CCC1(COCCCC(=O)CC(C)=O)COC1]

It may be appropriate to add a corresponding initiator for the polymerisation reaction. Suitable initiators are, for example, $AlCl_3$, $BF_3$, triphenylmethyl perchlorate, tropylium hexachloroantimonate, etc. Photoacids can likewise be added as initiators.

c) Groups which Undergo a Polycycloaddition

In this class of polymerisable groups, suitable groups are, for example, those which undergo a 1,3-dipolar addition reaction. The reaction here takes place between two complementary groups, for example a reaction of an azide with a terminal alkenyl or alkynyl group. The compound of the formula (1) must therefore have at least two groups which are able to undergo a reaction of this type. The polymerisation then proceeds in accordance with the following general scheme, where R generally represents the metal complex, * indicates the linking in the polymer and further comonomers may of course also be employed:

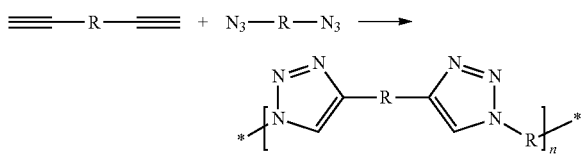

Furthermore, groups which undergo a Diels-Alder reaction are suitable in this class of polymerisable groups. The reaction here takes place between an alkenyl group and a dienyl group. Furthermore, it is also possible for two dienyl groups to react with one another, in which case the first of the two dienyl groups reacts as a simple alkenyl group. The compound of the formula (1) must have at least two groups which are able to undergo a reaction of this type. The compound of the formula (1) here can have either at least two alkenyl groups or at least one alkenyl group and at least one dienyl group or at least two dienyl groups. The polymerisation then proceeds in accordance with the following general scheme, where R generally represents the metal complex, * indicates the linking in the polymer and further comonomers may of course also be employed:

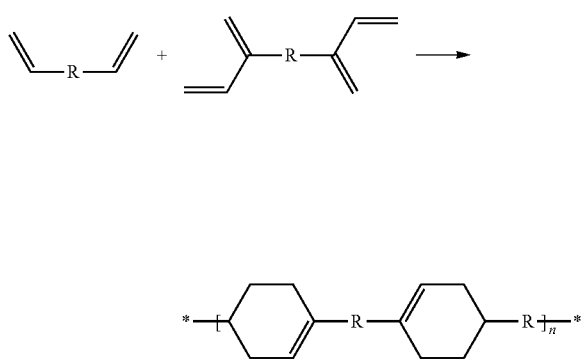

d) Carboxylic Acid Derivatives, Amines and Alcohols

Furthermore, groups which undergo a polycondensation reaction with one another are suitable as class of polymerisable groups. In particular, carboxylic acid derivatives which react with amines or alcohols are suitable here. Suitable carboxylic acid derivatives are, for example, carboxylic acids, carboxylic acid esters or carboxylic acid chlorides. Further suitable reactants are, for example, dithiols, dioxiranes, disulfuryl chlorides or diisocyanates. Thus, for example, the groups mentioned below are suitable, where the metal complex is indicated in each of these groups by R:

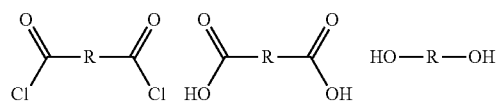

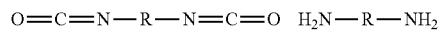

The compound of the formula (1) must have at least two groups of this type which are able to undergo a reaction of this type. The compound of the formula (1) here can have either at least two groups which are derived from carboxylic acids or at least one group which is derived from a carboxylic acid and at least one alcohol or amino group or at least two alcohol or amino groups. If the compound of the formula (1) only has groups which are derived from carboxylic acids, the use of a further monomer which has polymerisable alcohol or amino groups is necessary. If the compound of the formula (1) only has alcohol or amino groups as polymerisable groups, the use of a further monomer which has polymerisable groups which are derived from carboxylic acids is necessary.

e) Silanes

Furthermore, silane groups $Si(R^8)_3$ are suitable as class of polymerisable groups, where at least two groups $R^8$, preferably all three groups $R^8$, stands for Cl or an alkoxy group having 1 to 20 C atoms. This group reacts in the presence of water to give a polysiloxane. Depending on whether two or three such groups $R^8$ are bonded in the silane group, the polymer generated therefrom is a linear polymer or a crosslinked polymer.

Suitable further comonomers for the generation of polymers here are the structures depicted above in which R does not stand for a corresponding metal complex, but instead for any desired radical, in particular for a radical $R^8$.

The above-mentioned polymerisable groups PG are generally known to the person skilled in the art in the area of polymer chemistry, as are the suitable reaction conditions used for the polymerisation of these groups.

The complexes of the formula (1) according to the invention can contain one or more of the above-mentioned polymerisable groups PG. In a preferred embodiment of the invention, the complex of the formula (1) contains one, two or three polymerisable groups PG.

The metal complexes according to the invention can in principle be prepared by various processes. However, the processes described below have proven particularly suitable.

The present invention therefore furthermore relates to a process for the preparation of the metal complex compounds of the formula (1) by reaction of the corresponding free ligands with metal alkoxides of the formula (147), with metal ketoketonates of the formula (148), with metal halides of the formula (149) or with dimeric metal complexes of the formula (150):

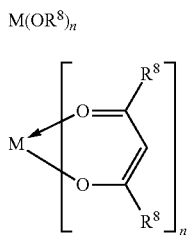

M(OR⁸)ₙ formula (147)

formula (148)

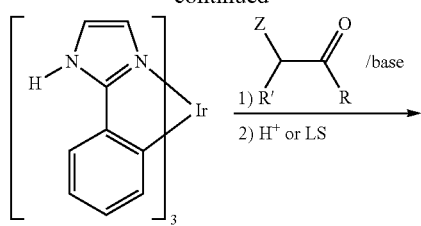

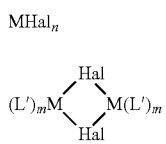

MHalₙ formula (149)

formula (150)

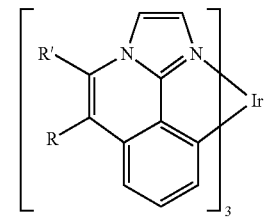

where the symbols M, L', m, n and R⁸ have the meanings indicated above, and Hal=F, Cl, Br or I.

It is likewise possible to use metal compounds, in particular iridium compounds, which carry both alkoxide and/or halide and/or hydroxyl radicals as well as ketoketonate radicals. These compounds may also be charged. Corresponding iridium compounds which are particularly suitable as starting materials are disclosed in WO 2004/085449. Particularly suitable is [IrCl₂(acac)₂]⁻, for example Na[IrCl₂(acac)₂]. Particularly preferred starting materials are furthermore Ir(acac)₃ and Ir(tBu-acac)₃.

Suitable platinum starting materials are, for example, PtCl₂, K₂[PtCl₄], PtCl₂(DMSO)₂, Pt(Me)₂(DMSO)₂ or PtCl₂(benzonitrile)₂.

It is furthermore possible firstly to prepare a precursor of the metal complex and to introduce the bridge between the two coordinating aryl or heteroaryl rings in a further step. This is shown by way of example for a complex in the following scheme:

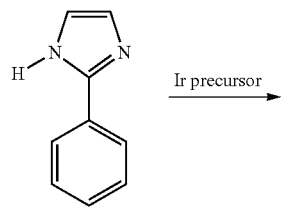

R, R' = radicals as defined
Z = Cl, Br, I, OMes, O(F₃Mes), OTos,
LS = Lewis acid, such as BZ₃, AlZ₃

It is furthermore possible to synthesise compounds of the formula (1) which carry no polymerisable groups PG, and to introduce the polymerisable group on the finished complex in a further synthetic step.

The synthesis of the complexes is preferably carried out as described in WO 2002/060910 and in WO 2004/085449. Heteroleptic complexes can also be synthesised, for example, in accordance with WO 2005/042548. The synthesis here can also be activated, for example, thermally, photochemically and/or by microwave radiation. In a preferred embodiment of the invention, the reaction is carried out in the melt without the use of an additional solvent. "Melt" here means that the ligand is in molten form and the metal precursor is dissolved or suspended in this melt.

These processes enable the compounds of the formula (1) according to the invention to be obtained in high purity, preferably greater than 99% (determined by means of ¹H-NMR and/or HPLC).

The synthetic methods explained here enable, inter alia, the synthesis of structures 1 to 96 according to the invention which are depicted below.

1

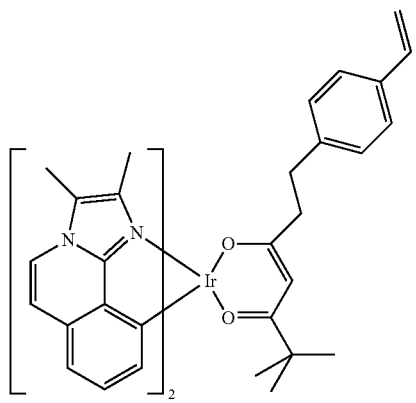

2

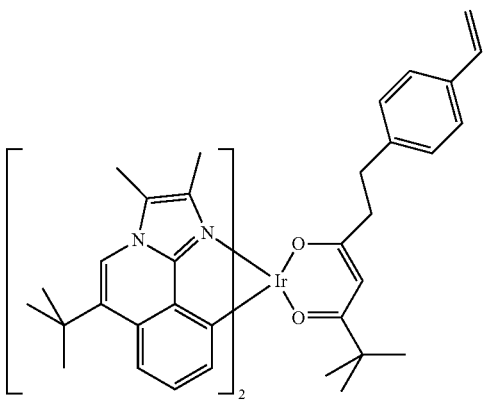

-continued
3
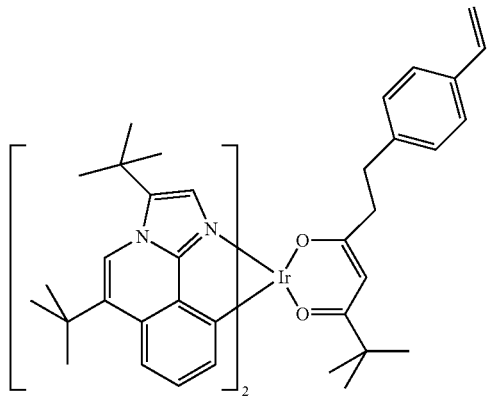
4
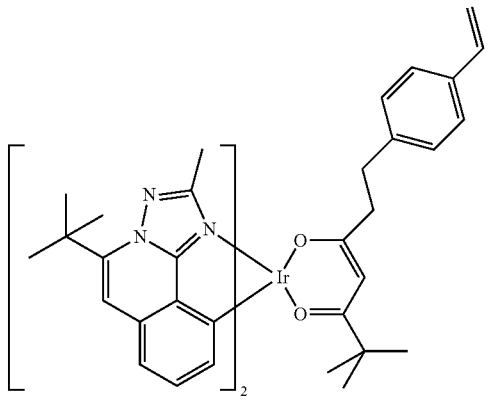
5
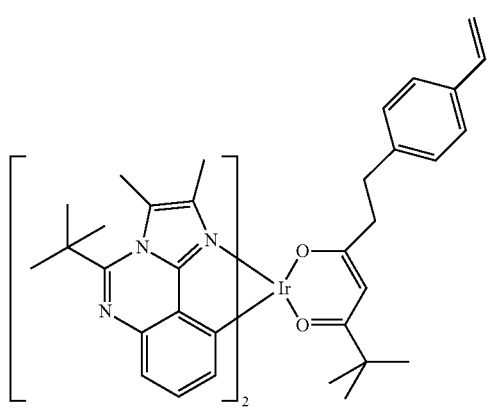
6
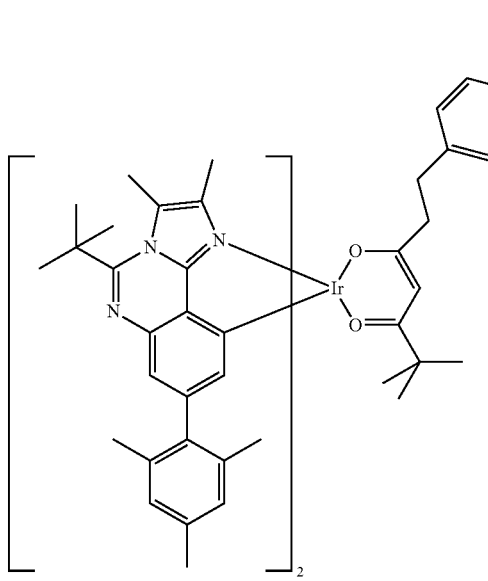
7
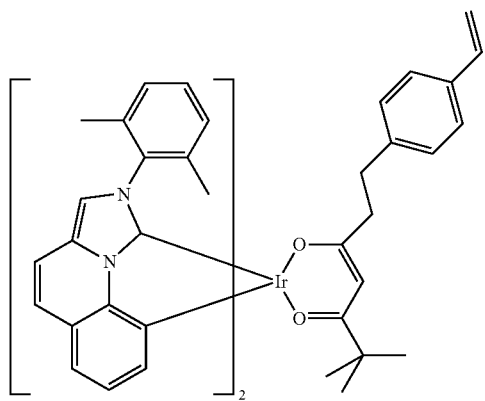
8
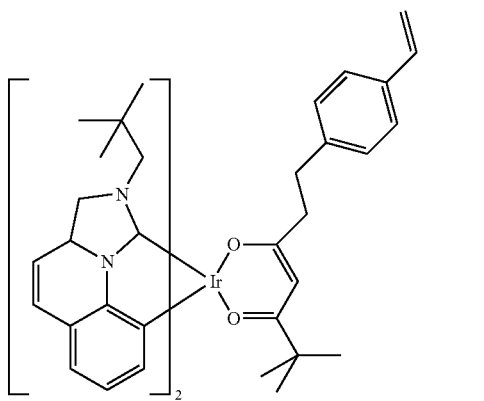

-continued
9
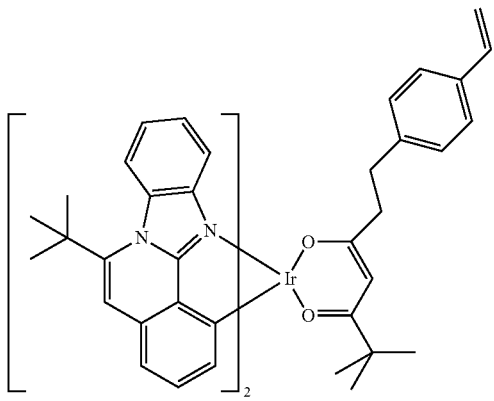
10
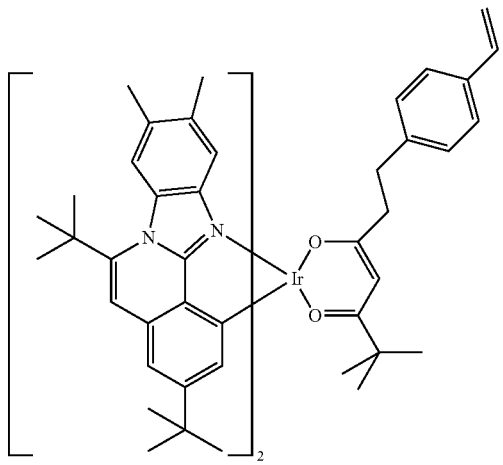
11
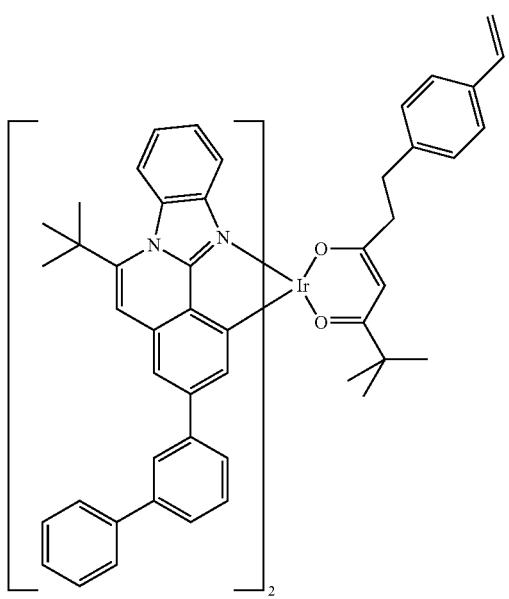
12
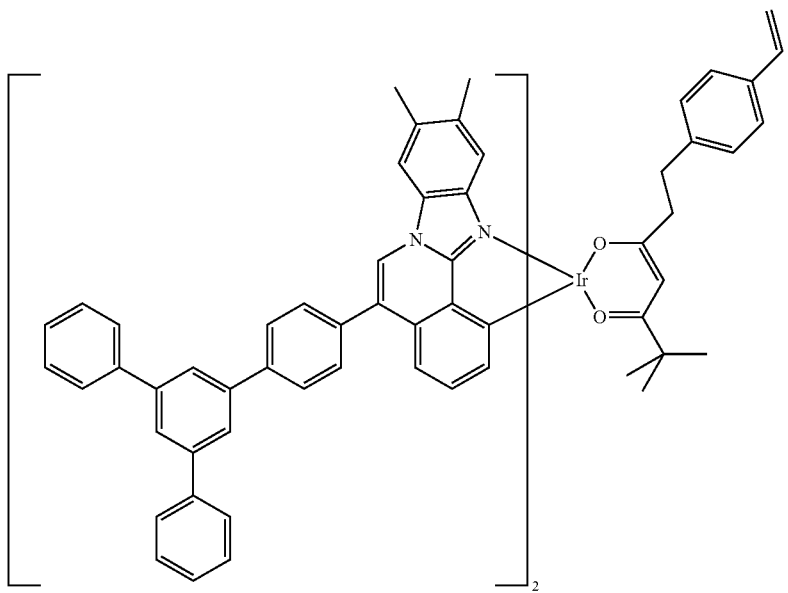

-continued
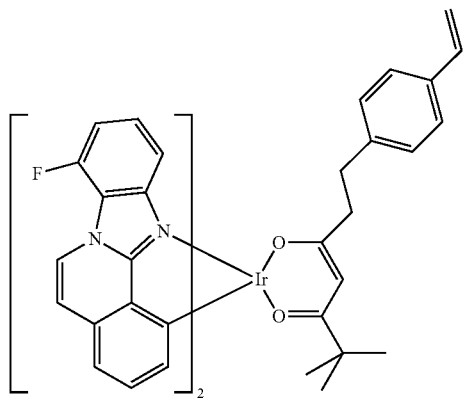
13
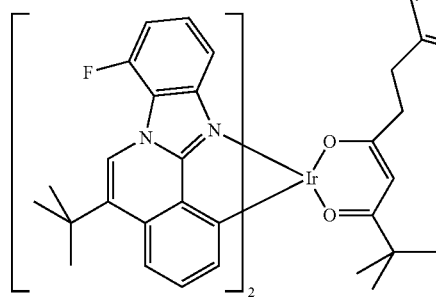
14
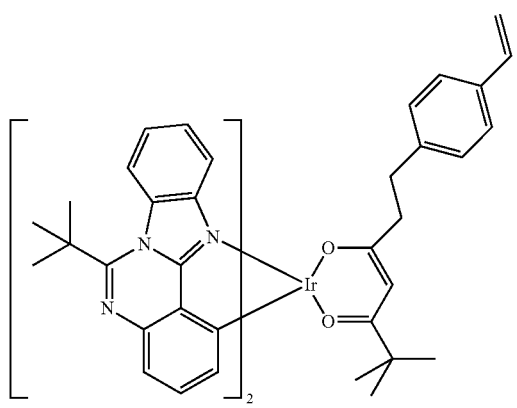
15
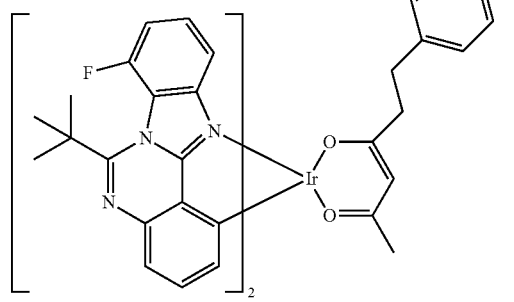
16
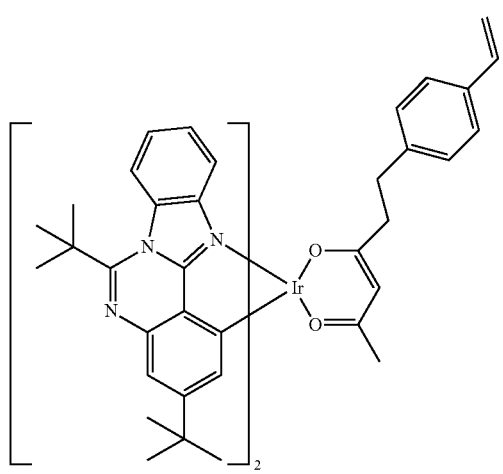
17
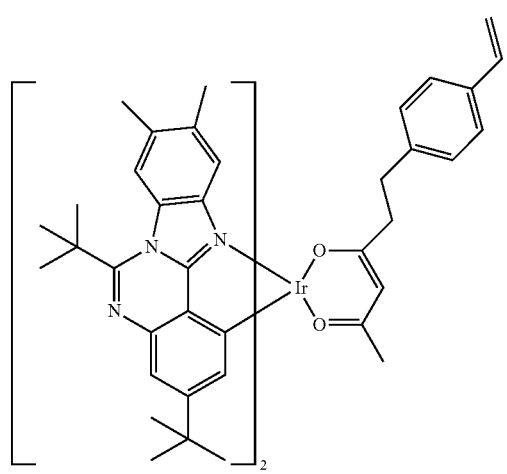
18

-continued
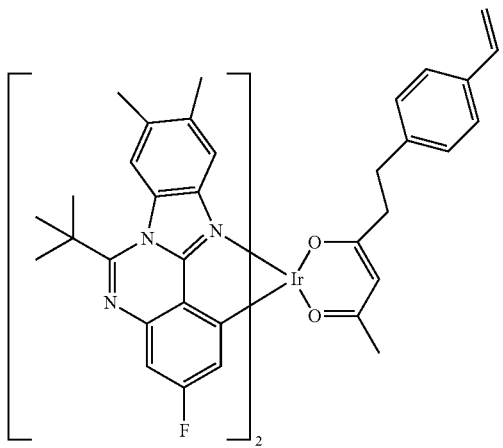
19
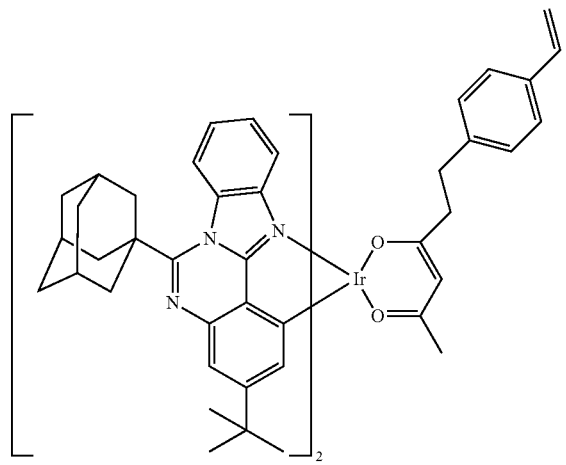
20
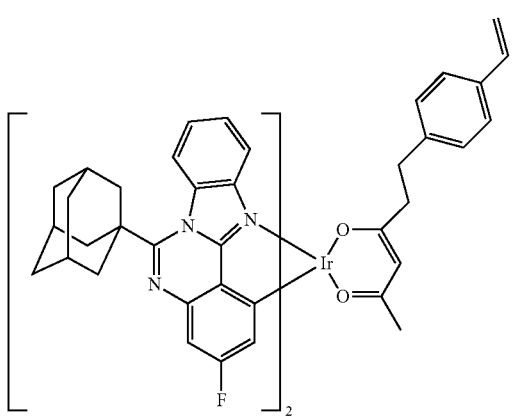
21
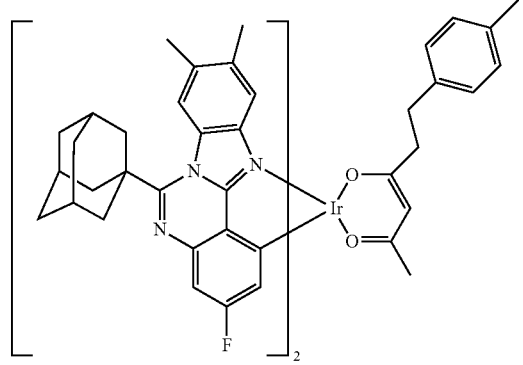
22
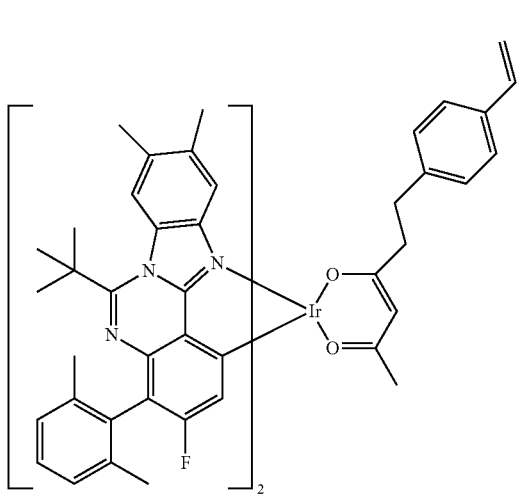
23
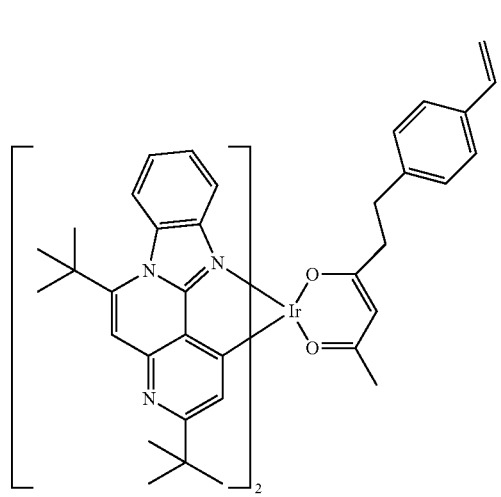
24

25
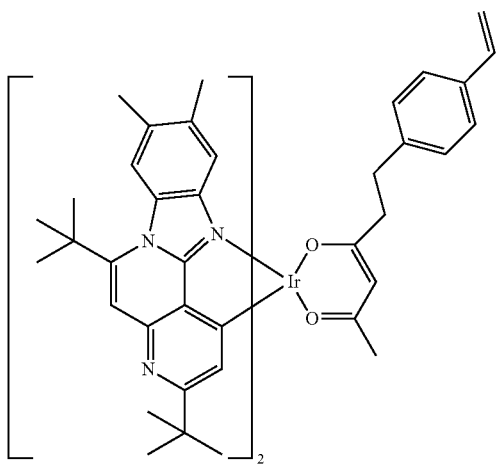
26
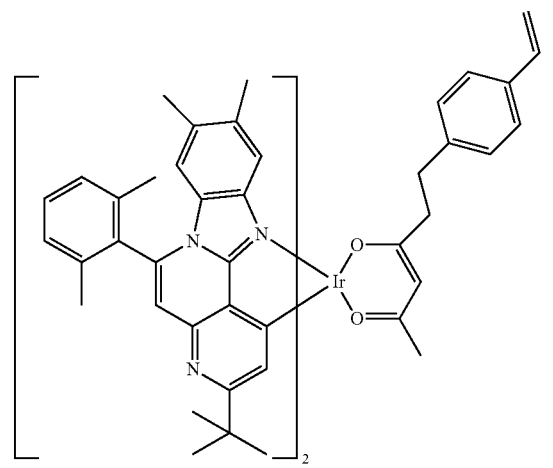
27
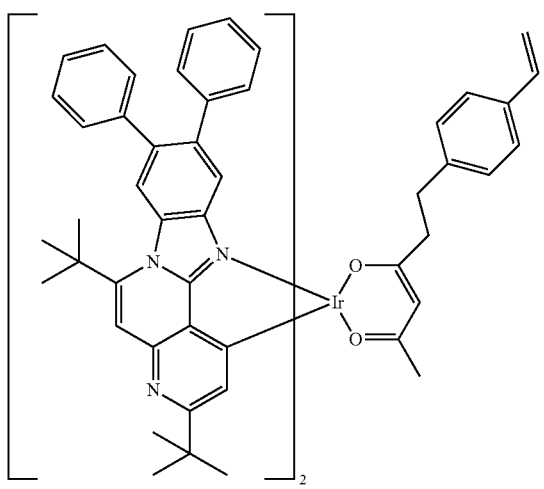
28
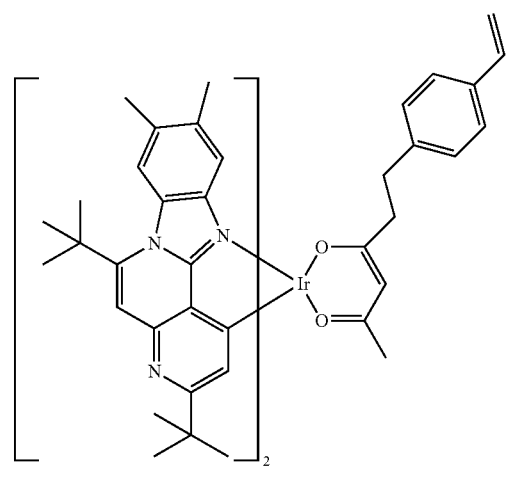
29
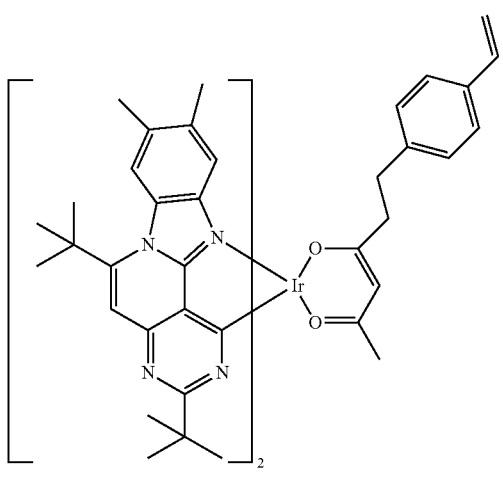
30
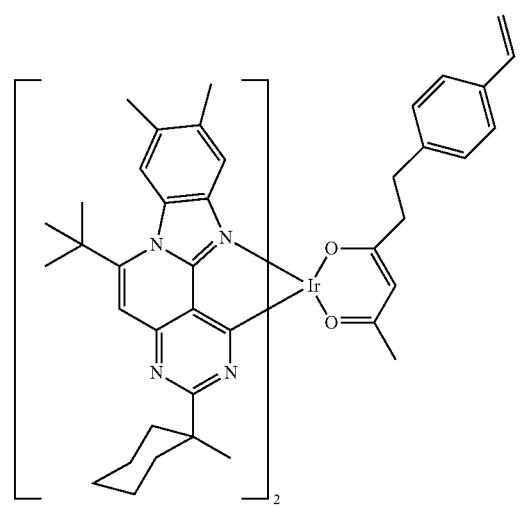

-continued
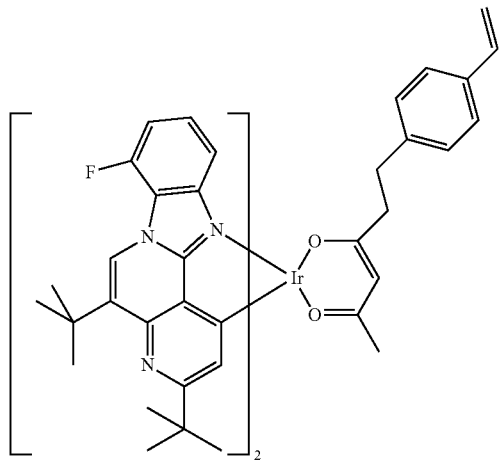
31
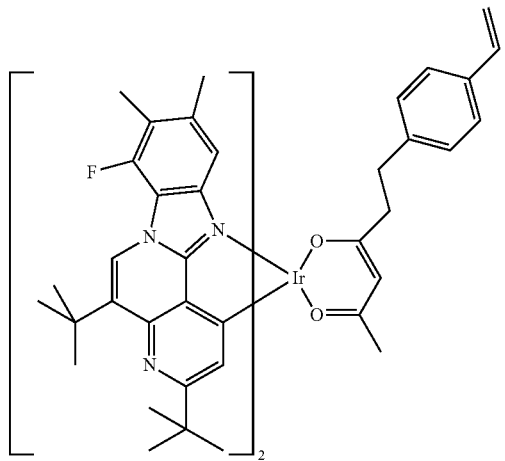
32
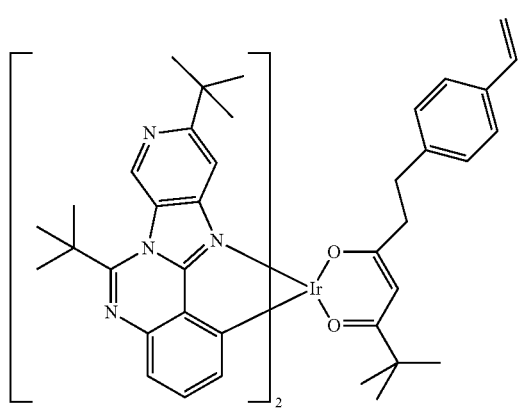
33
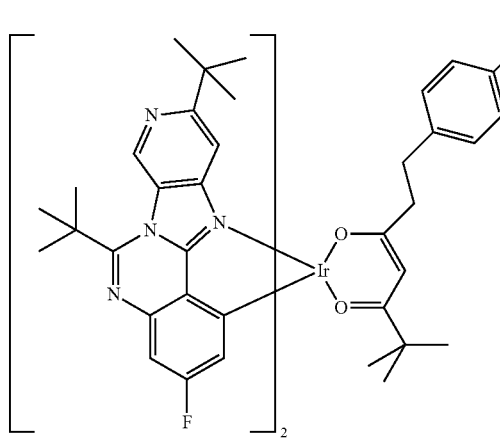
34
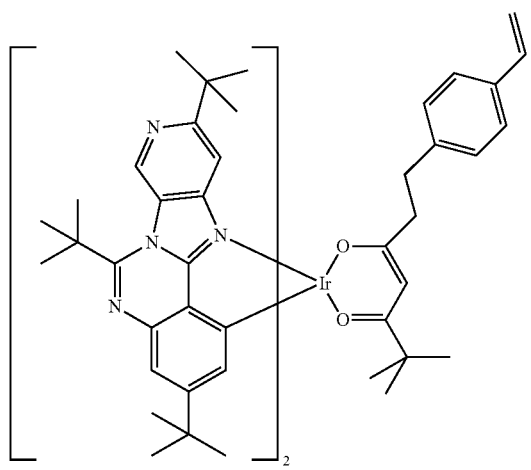
35
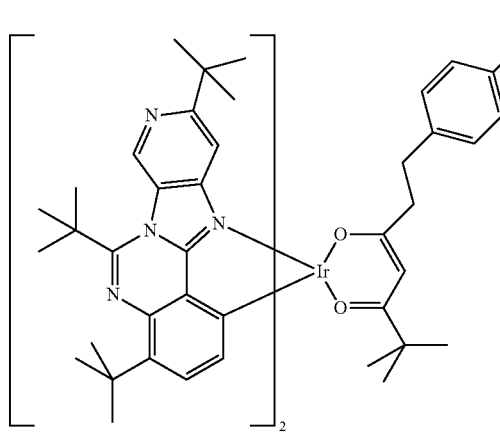
36

-continued
37
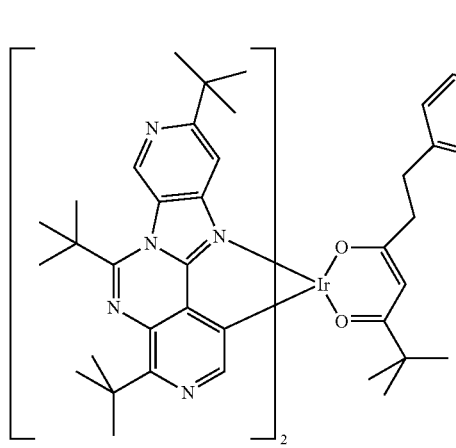
38
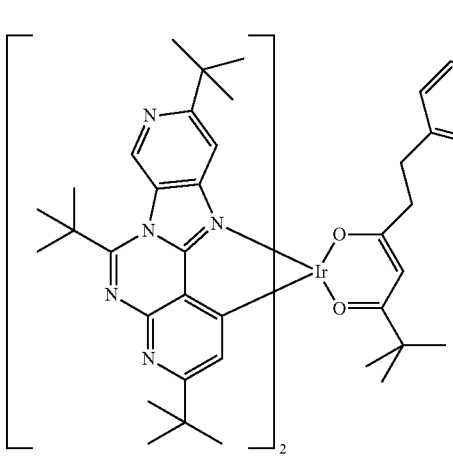
39
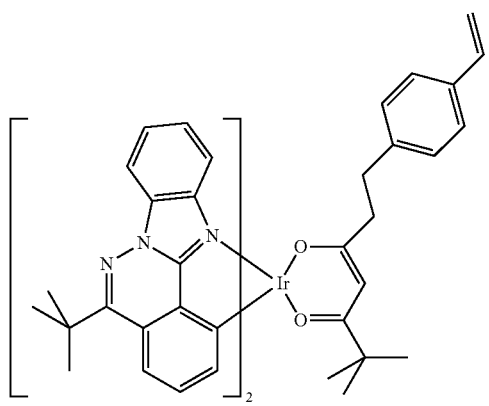
40
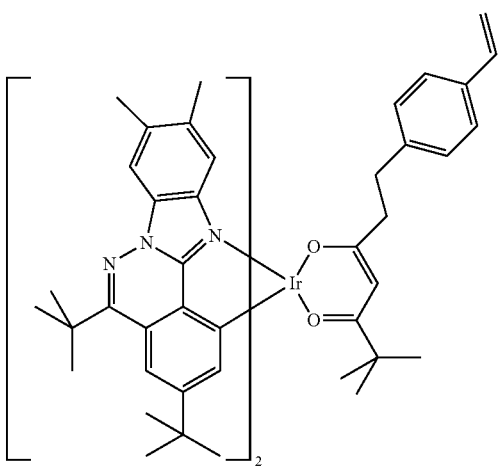
41
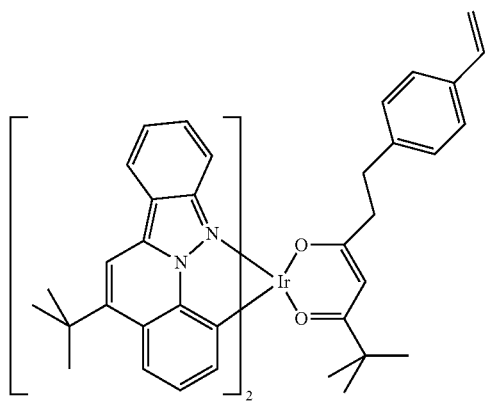
42
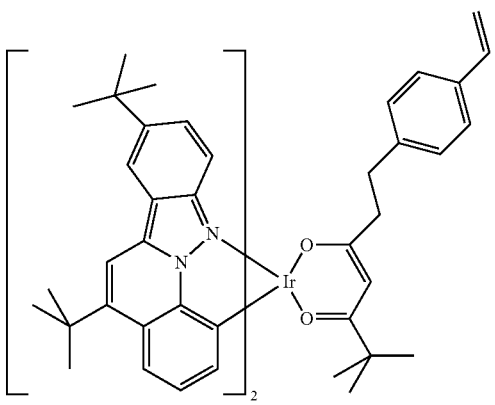

43
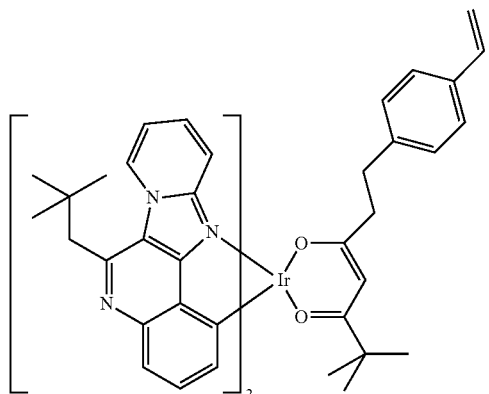
44
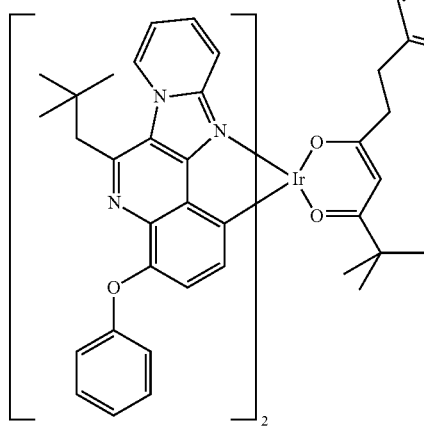
45
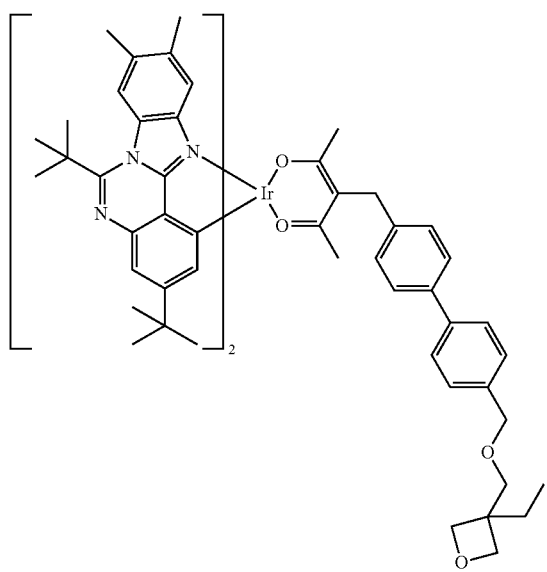
46
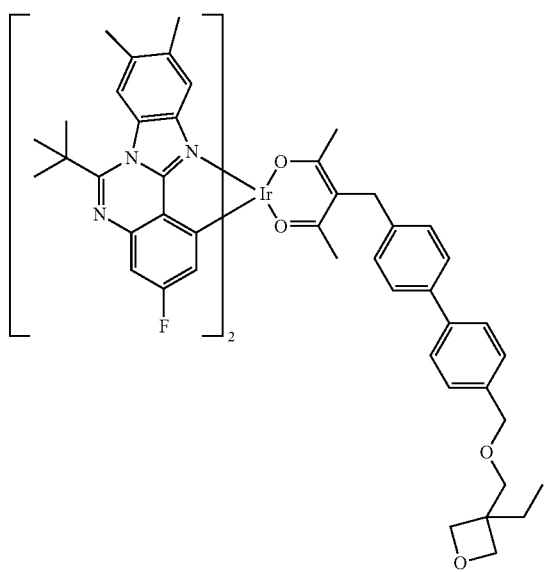

47
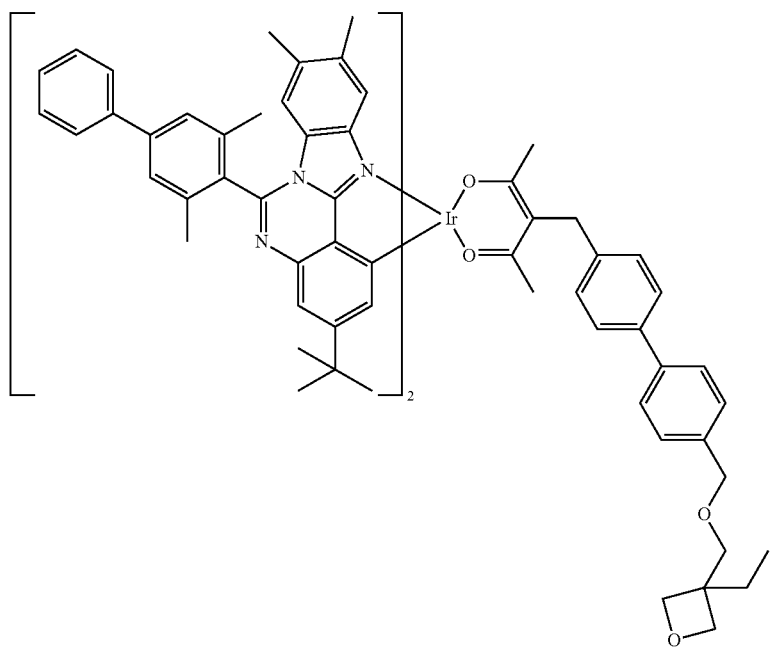
48
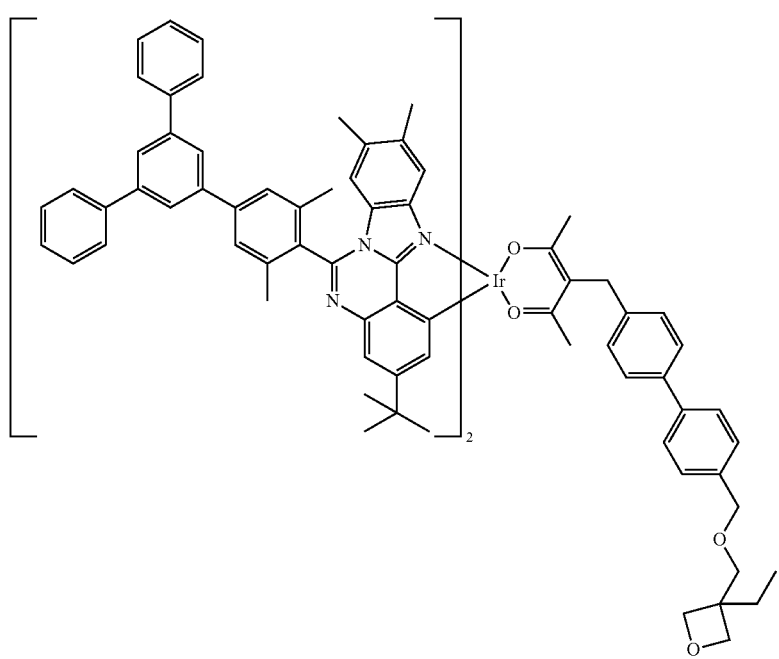

-continued
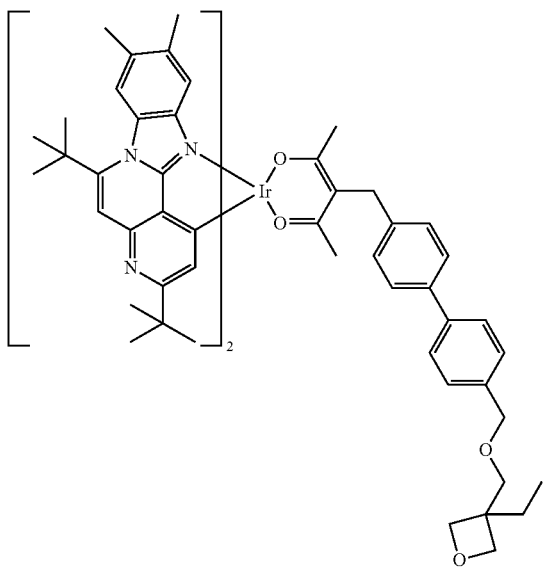
49
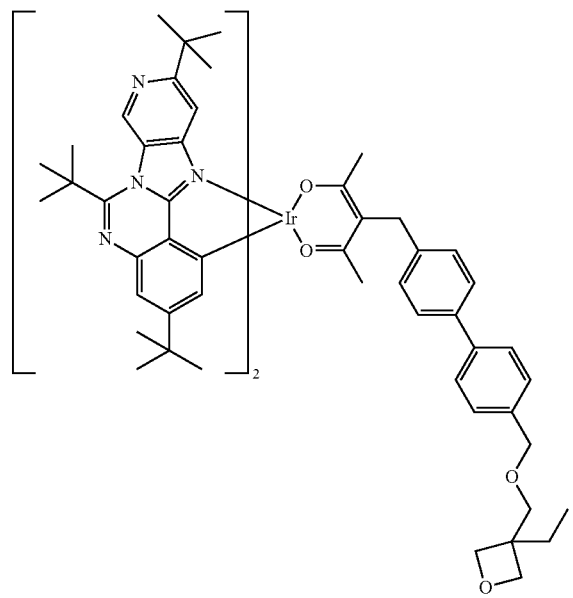
50
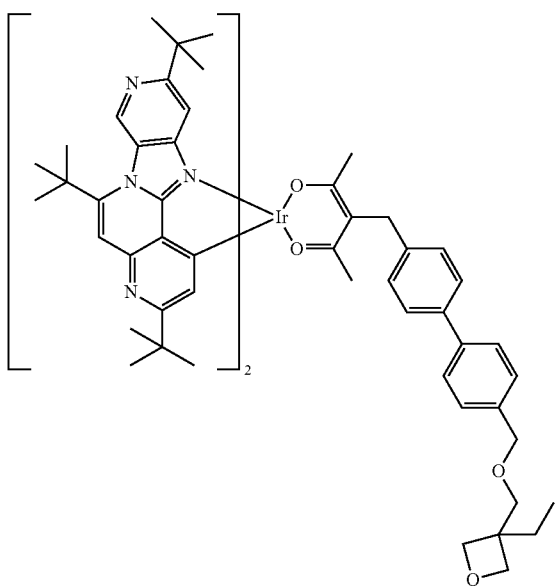
51
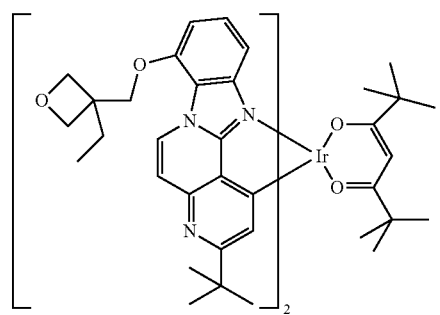
52
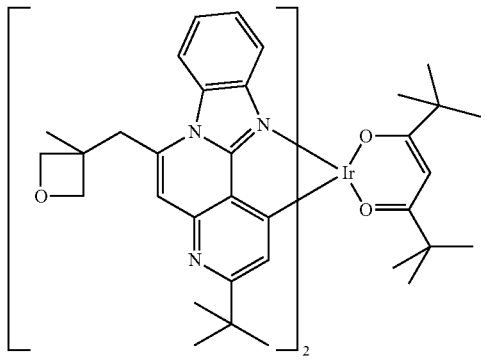
53
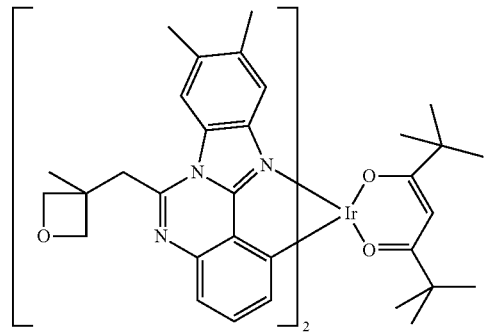
54

-continued
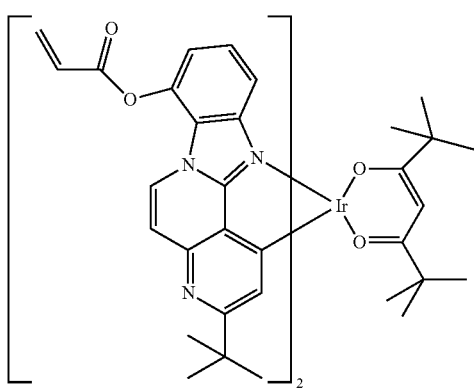
55
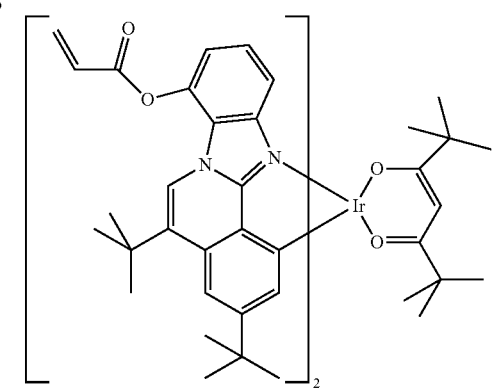
56
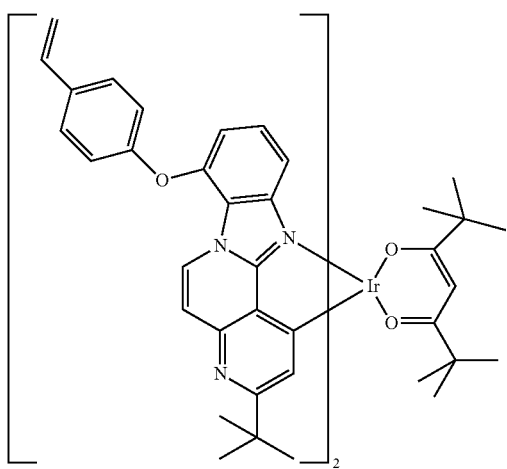
57
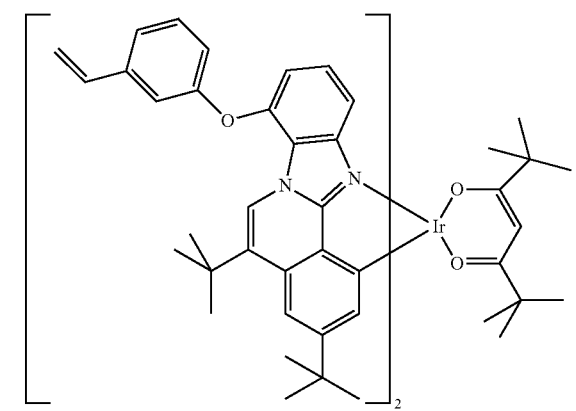
58
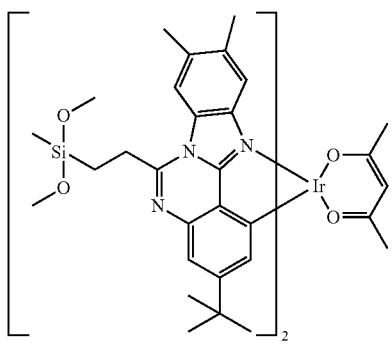
59
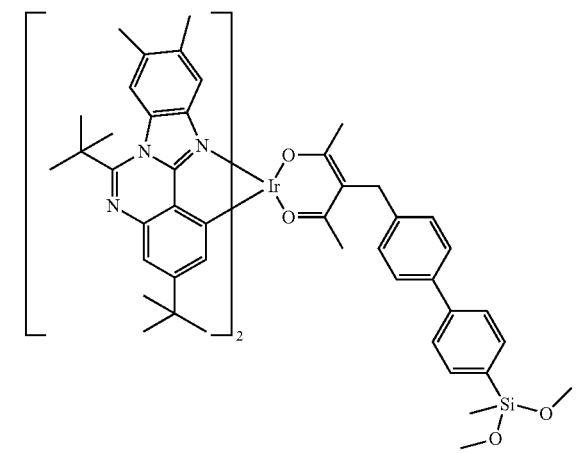
60

-continued
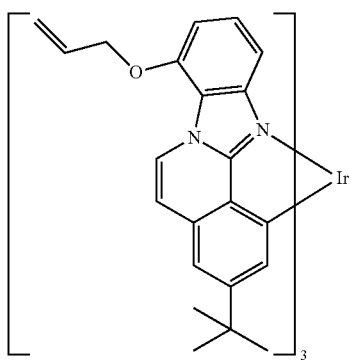
61
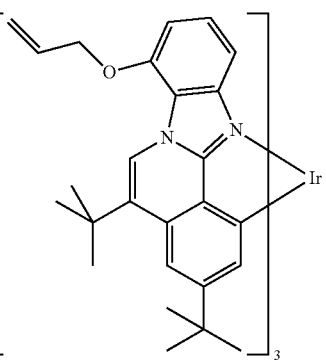
62
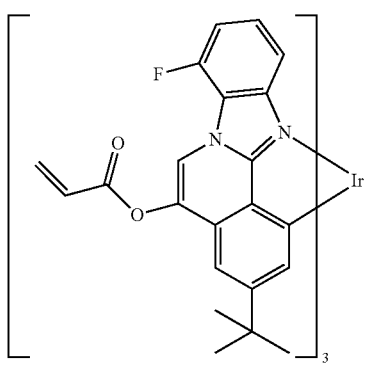
63
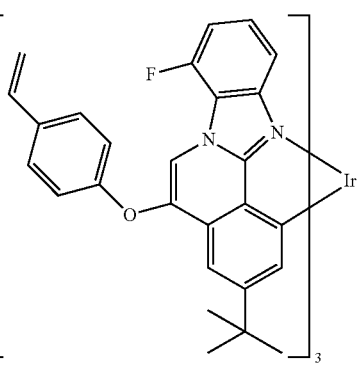
64
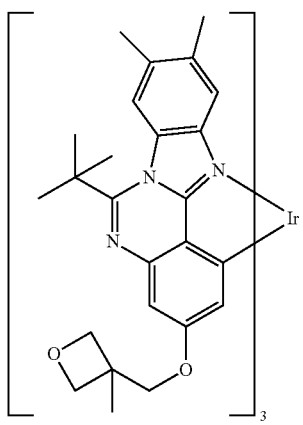
65
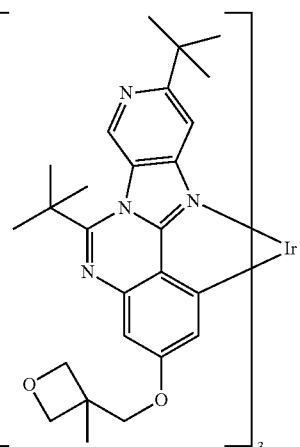
66
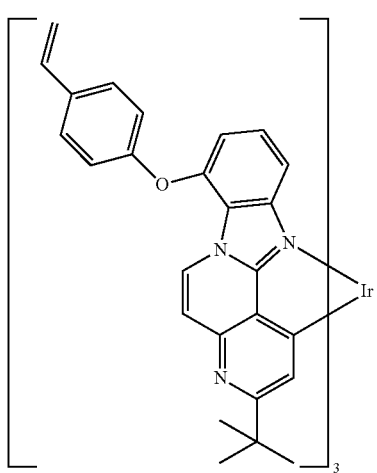
67
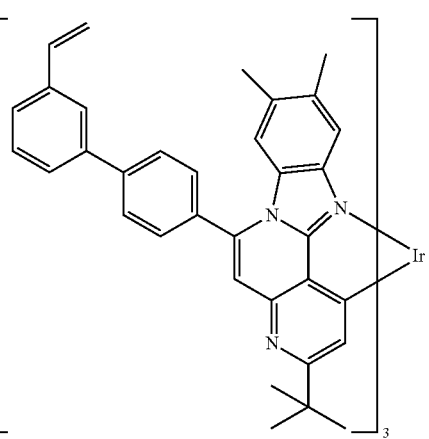
68

-continued
69
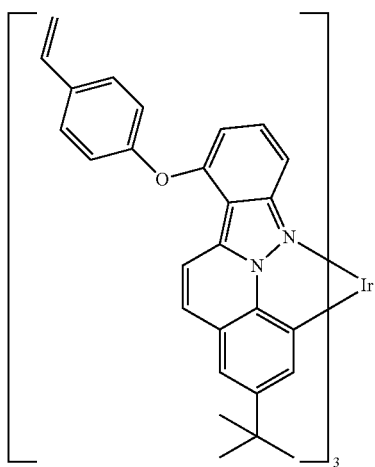
70
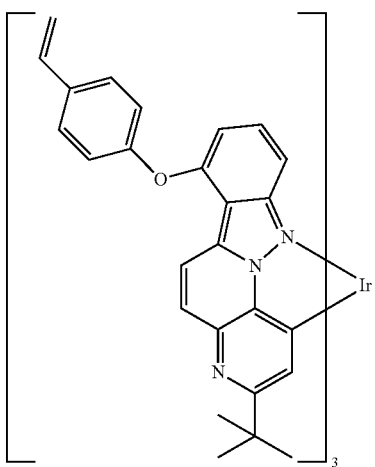
71
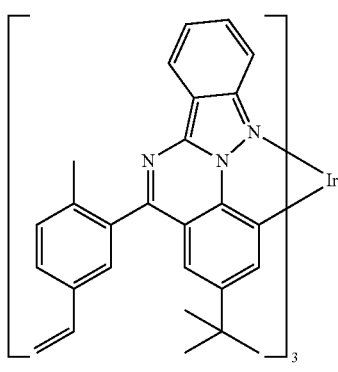
72
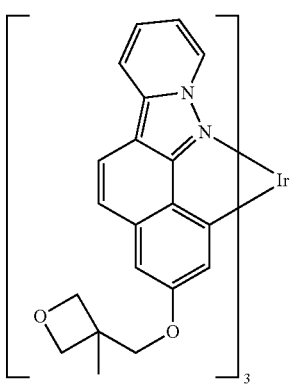
73
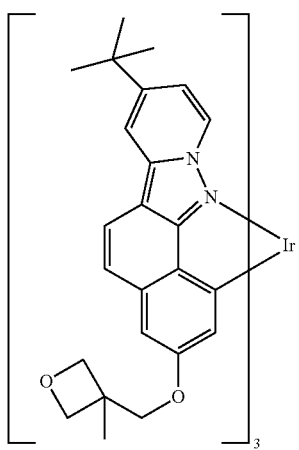
74
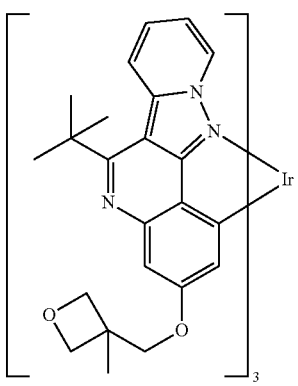

-continued
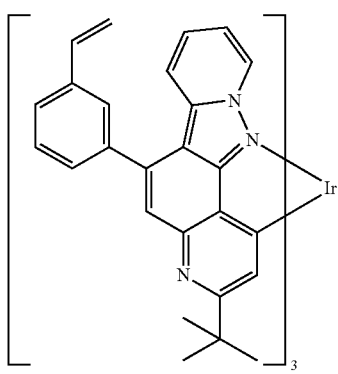
75
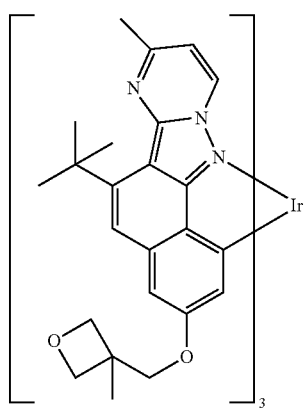
76
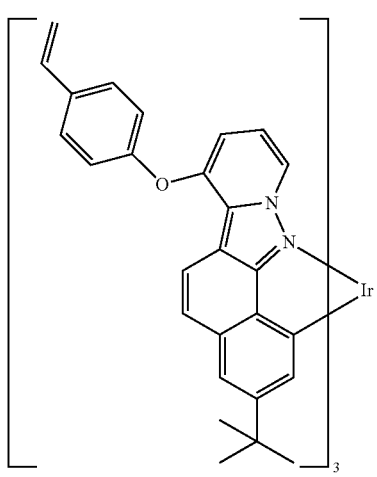
77
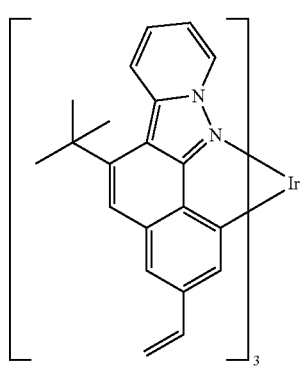
78
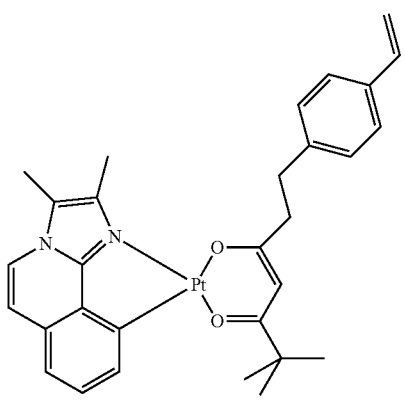
79
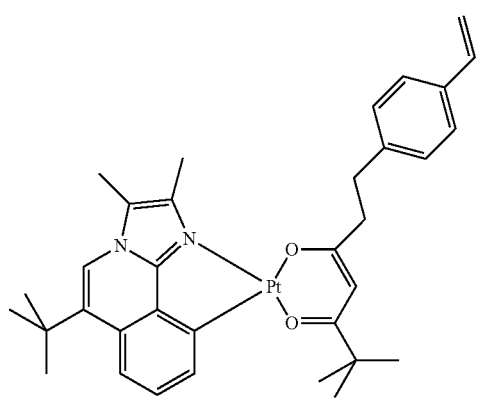
80

-continued
81
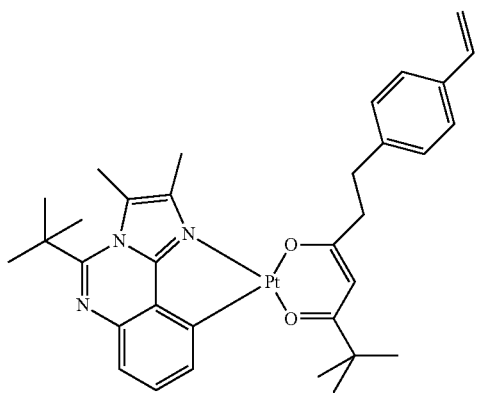
82
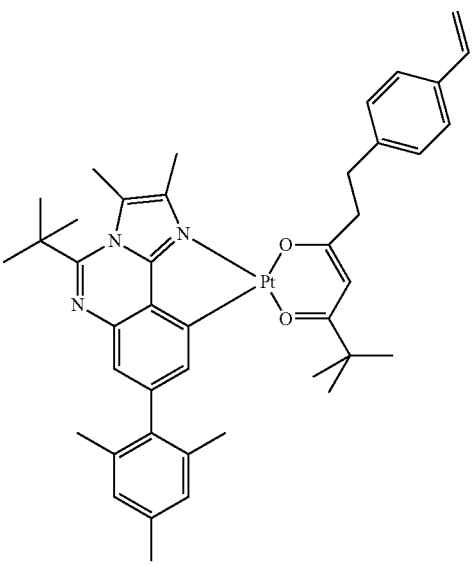
83
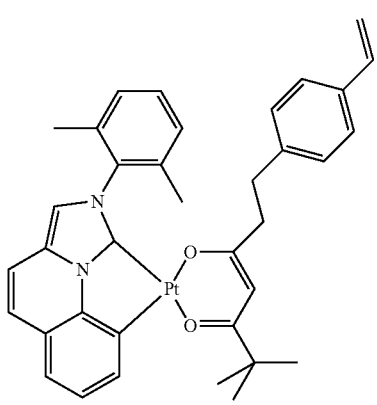
84
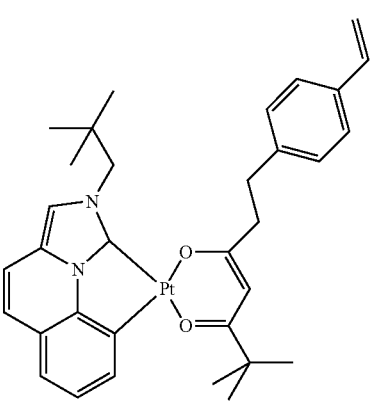
85
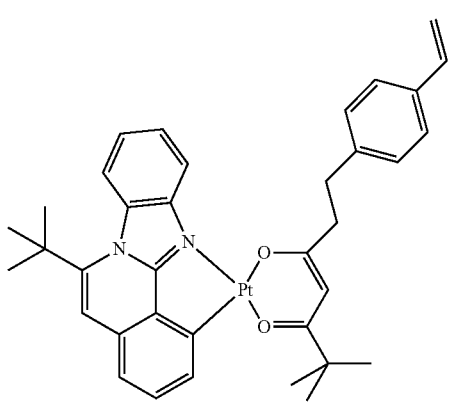
86
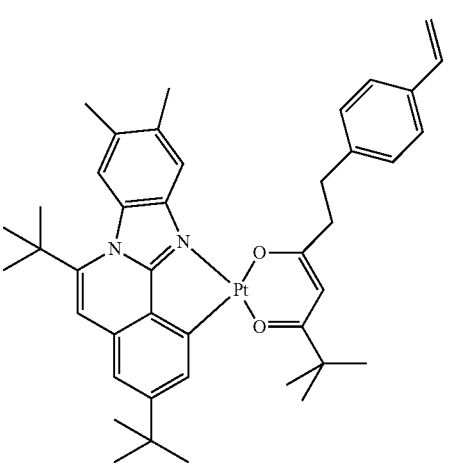

-continued
87
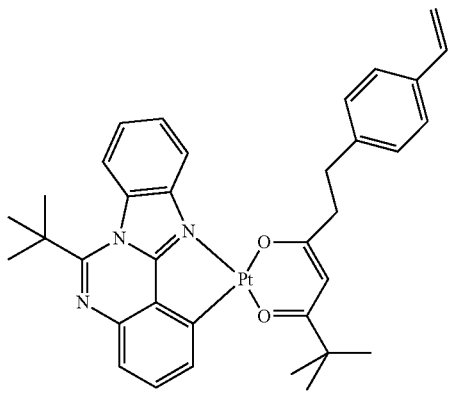
88
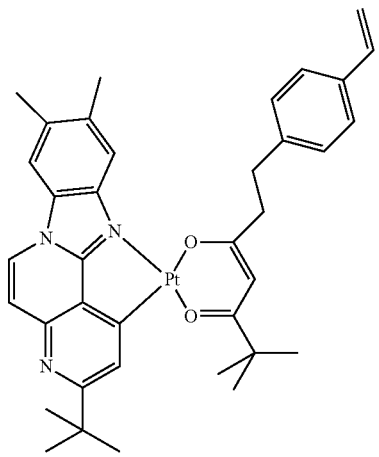
89
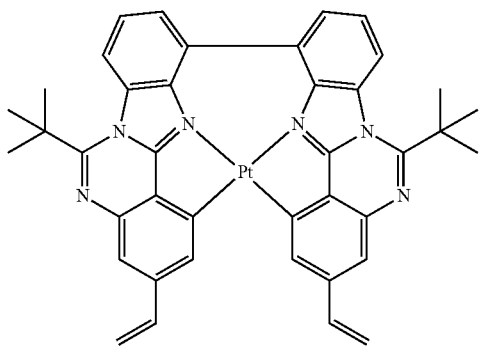
90
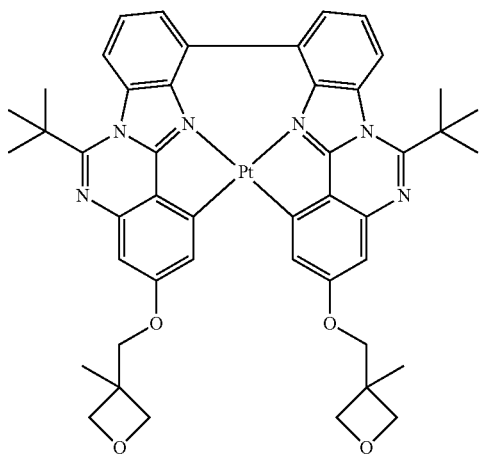
91
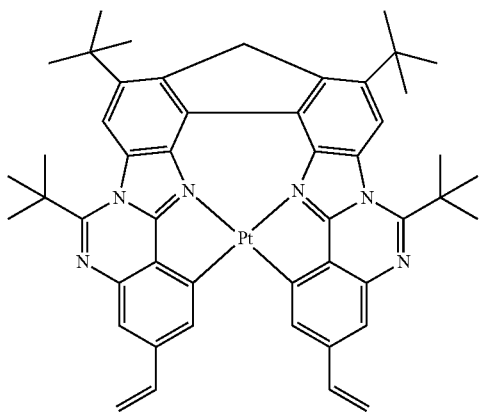
92
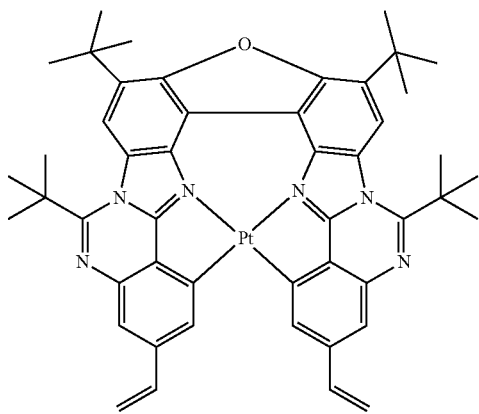

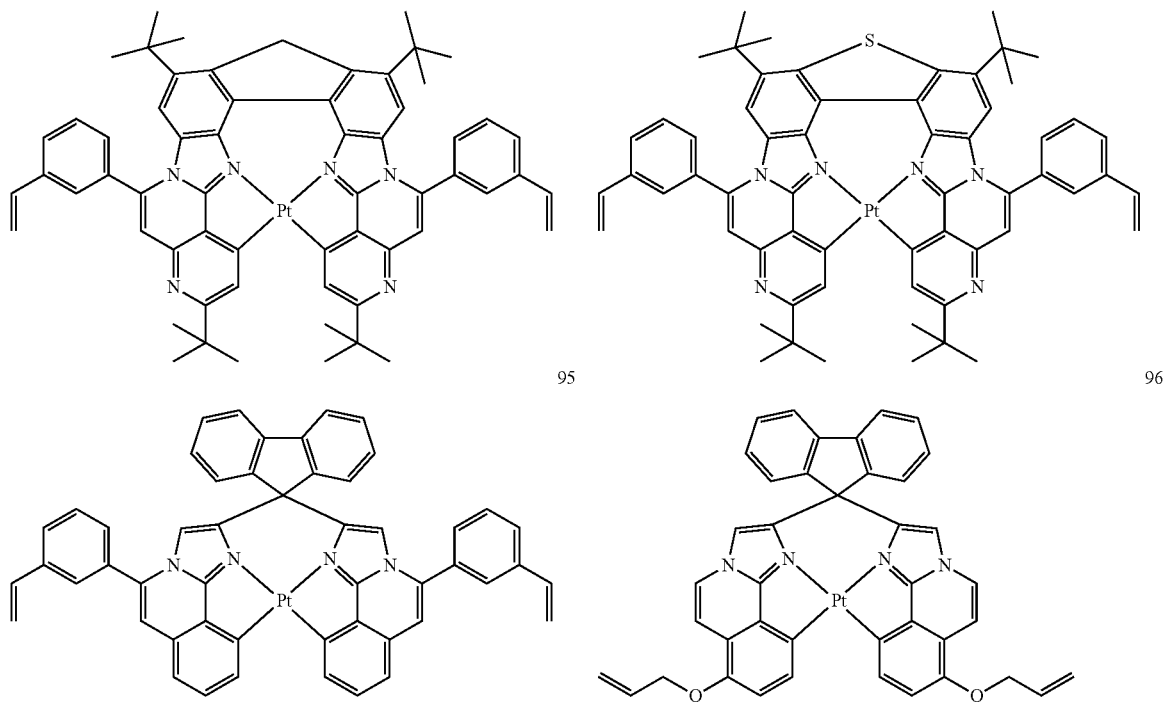

The compounds of the formula (1) according to the invention are used, as described above, as monomers for the preparation of polymers, where the polymerisation takes place via the polymerisable group PG.

The term "polymer" in the sense of the present invention also encompasses oligomers and dendrimers.

The term oligomer in the sense of the present invention is applied to a compound which has three to nine recurring units. A polymer in the sense of the present invention is taken to mean a compound which has ten or more recurring units. The branching factor of the polymers here is between 0 (linear polymer, no branching points) and 1 (fully branched dendrimer).

The present invention therefore furthermore relates to the use of a compound of the formula (1) for the preparation of a polymer.

The present invention still furthermore relates to a polymer obtainable by polymerisation of a compound of the formula (1) and optionally further monomers, where the polymerisation reaction takes place via the polymerisable group PG.

For units of the formula (1), the same preferences apply in polymers as already described above. Apart from the units mentioned above, the polymers may contain further units selected, for example, from recurring units which have hole-transport properties or electron-transport properties. Suitable for this purpose are the materials or recurring units known from the prior art.

The above-mentioned homopolymers and copolymers are distinguished by high efficiency and stability in electroluminescent devices and, if they are uncrosslinked polymers, by their good solubility in organic solvents.

The units of the formula (1) may be bonded in the main chain or to the side chain in the polymer according to the invention. In a preferred embodiment of the invention, the units of the formula (1) are bonded in the side chain. Depending on the structure of the units of the formula (1), these units may also form the branching point of branched or crosslinked polymers.

The proportion of the structural unit of the general formula (1) in the polymer is in the range from 0.001 to 100 mol %, preferably in the range from 0.01 to 50 mol % and particularly preferably in the range from 0.1 to 40 mol %, in particular from 0.5 to 30 mol %.

It is also possible for different structural units of the formula (1) to be present in the polymer, oligomer or dendrimer, for example structural units which emit blue, green and red, so that overall white emission is generated. The structural units of the formula (1) and other emitting structural units, which may be fluorescent or phosphorescent, may likewise be present in the polymer, oligomer or dendrimer, for example structural units which emit blue, green and red, so that overall white emission is generated.

Besides one or more structural units of the general formula (1), the polymers according to the invention may also contain further structural units. These are, inter alia, those as disclosed and listed extensively, for example, in WO 2002/077060 and in WO 2005/014689. These are incorporated into the present invention by way of reference. The further structural units can originate, for example, from the following classes:

group 1: units which have hole-injection and/or hole-transport properties;
group 2: units which have electron-injection and/or electron-transport properties;
group 3: units which exhibit electrophosphorescence;
group 4: units which improve the transfer from the singlet to the triplet state;
group 5: units which influence the emission colour of the resultant polymers;
group 6: units which are typically used as polymer backbone;

group 7: units which influence the film morphology and/or the rheological properties of the resultant polymers.

In a preferred embodiment of the invention, the triplet level $T_1$ of all structural units used in the polymer, oligomer or dendrimer which do not exhibit phosphorescence is higher than the triplet level of the triplet emitter emitting at the shortest wavelength (metal complex) which is present in the polymer, oligomer or dendrimer. "Structural unit" in conjugated polymers is regarded as being the conjugation length and not the structure of the individual recurring unit.

Preferred polymers according to the invention are those in which at least one structural unit has charge-transport properties, i.e. which contain units from group 1 and/or 2.

Structural units from group 1 which have hole-injection and/or hole-transport properties are, for example, triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives and further O-, S- or N-containing heterocycles having a high HOMO (HOMO=highest occupied molecular orbital). These arylamines and heterocycles preferably result in an HOMO in the polymer of greater than −5.8 eV (against vacuum level), particularly preferably greater than −5.5 eV.

Structural units from group 2 which have electron-injection and/or electron-transport properties are, for example, pyridine, pyrimidine, pyridazine, pyrazine, oxadiazole, quinoline, quinoxaline, triphenylene, benzimidazole, triazine, ketone, phosphine oxide and phenazine derivatives, but also triarylboranes and further O-, S- or N-containing heterocycles having a low LUMO (LUMO=lowest unoccupied molecular orbital). These units in the polymer preferably result in an LUMO of less than −2.5 eV (against vacuum level), particularly preferably less than −2.7 eV.

Structural units from group 3 are those which are able to emit light from the triplet state with high efficiency, even at room temperature, i.e. exhibit electrophosphorescence instead of electrofluorescence. Suitable for this purpose are firstly compounds which contain heavy atoms having an atomic number of greater than 36. Preference is given to compounds which contain d- or f-transition metals which satisfy the above-mentioned condition. Particular preference is given here to corresponding structural units which contain elements from groups 8 to 10 (Ru, Os, Rh, Ir, Pd, Pt). For the purposes of the present invention, all luminescent metal complexes which contain the above-mentioned metals are to be regarded as phosphorescent.

Structural units from group 4 are those which improve the transfer from the singlet state to the triplet state and which improve the phosphorescence properties of these structural elements. Suitable for this purpose are, in particular, carbazole and bridged carbazole dimer units, as described, for example, in WO 2004/070772 and WO 2004/113468. Also suitable for this purpose are triazines, ketones, phosphine oxides, sulfoxides, sulfones, silane derivatives and similar compounds, as described, for example, in WO 2005/040302.

Structural units from group 5, besides those mentioned above, are those which have at least one further aromatic structure or another conjugated structure which does not fall under the above-mentioned groups, i.e. which have only little influence on the charge-carrier mobilities, are not organometallic complexes or have no or no significant influence on the singlet-triplet transfer. Structural elements of this type can influence the emission colour of the resultant polymers. Depending on the unit, they can therefore also be employed as emitters. Preference is given here to aromatic structures having 6 to 40 C atoms and also tolan, stilbene or bisstyrylarylene derivatives, each of which may be substituted by one or more radicals R. Particular preference is given here to the incorporation of 1,4-phenylene, 1,4-naphthylene, 4,4'-biphenylylene, 4,4"-terphenylylene, 4,4'-bi-1,1'-naphthylylene, 4,4'-tolanylene, 4,4'-stilbenzylene, 4,4"-bisstyrylarylene, benzothiadiazole and corresponding oxygen derivatives, quinoxaline, phenothiazine, phenoxazine, dihydrophenazine, bis(thiophenyl)arylene, oligo(thiophenylene), or phenazine derivatives, which are substituted or unsubstituted.

Structural units from group 6 are units which contain aromatic structures having 6 to 40 C atoms, which are typically used as polymer backbone.

These are, for example, 4,5-dihydropyrene derivatives, 4,5, 9,10-tetrahydropyrene derivatives, fluorene derivatives, 9,9'-spirobifluorene derivatives, phenanthrene derivatives, 9,10-dihydrophenanthrene derivatives, 5,7-dihydrodibenzoxepine derivatives and cis- and trans-indenofluorene derivatives.

Structural units from group 7 are those which influence the film morphology and/or the rheological properties of the polymers, such as, for example, siloxanes, long alkyl chains or fluorinated groups, but also particularly rigid or flexible units, such as, for example, liquid crystal-forming units or crosslinkable groups.

Preference is given to polymers according to the invention which at the same time, besides the structural units of the general formula (1), additionally contain one or more units selected from groups 1 to 7, which may be different from the structural units according to the invention. It may likewise be preferred for more than one structural unit from a group to be present simultaneously.

It is particularly preferred for the polymers according to the invention to contain units which improve the charge transport or charge injection, i.e. units from groups 1 and/or 2; a proportion of 0.5 to 30 mol % of these units is particularly preferred; a proportion of 1 to 10 mol % of these units is very particularly preferred.

The above-mentioned preferences also apply to the units of the formula (1) in polymers.

The present invention furthermore relates to a formulation, in particular a solution, a dispersion or a mini-emulsion, comprising at least one polymer according to the invention and at least one solvent.

The polymers according to the invention are suitable for use in an electronic device.

In an embodiment of the invention, an electronic device is produced which comprises the compound of the formula (1), which still contains the polymerisable group PG, and optionally further monomers. This compound of the formula (1) and the optionally further monomers are then polymerised or crosslinked in the layer of the electronic device. This process is particularly suitable if the polymer obtained by the polymerisation reaction is an insoluble polymer, for example a crosslinked polymer.

In a further embodiment of the invention, firstly a polymer according to the invention is prepared from the compound of the formula (1) and optionally further monomers and is then employed for the production of the electronic device. This process is particularly suitable if the polymer obtained by the polymerisation reaction is a polymer which has sufficient solubility in a suitable solvent to be processed from solution.

An electronic device is taken to mean a device which comprises anode, cathode and at least one layer, where this layer comprises at least one organic or organometallic compound. The electronic device according to the invention thus comprises anode, cathode and at least one layer which comprises at least one polymer according to the invention which contains units of the formula (1) indicated above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components in an electronic device are generally the organic or inorganic materials which have been introduced between the anode and cathode, for example charge-injection, charge-transport or charge-blocking materials, but in particular emission materials and matrix materials. The polymers according to the invention exhibit particularly good properties as emission material in organic electroluminescent devices. Organic electroluminescent devices are therefore a preferred embodiment of the invention.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present. In particular if the polymer according to the invention, apart from units of the formula (1), has units for hole transport and/or electron transport, separate hole-transport or electron-transport layers can be omitted.

The organic electroluminescent device may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce. It is likewise possible for a plurality of emitting layers to be present in a layer or, for example, also to be bonded in a polymer, oligomer or dendrimer, so that the generation of white emission from a single layer is also possible.

If crosslinked and thus insoluble polymers are suitable in the case of the polymers according to the invention, these are particularly suitable for the production of electroluminescent devices having a plurality of emission layers, since it is possible to apply a further layer from solution to an emission layer which is already in crosslinked form and is therefore insoluble, without partially dissolving the emission layer which is already present.

In a preferred embodiment of the invention, the organic electroluminescent device comprises the polymer according to the invention in one or more emitting layers.

If the polymer according to the invention is employed as emitting material in an emitting layer, it can be employed, depending on the composition, as pure substance or in a mixture with one or more further polymers or low-molecular-weight compounds.

In a preferred embodiment of the invention, the polymer according to the invention is employed as a mixture with one or more matrix materials. This is the case, in particular, if the polymer itself contains no units which can usually serve as matrix material for phosphorescent compounds. It may likewise be appropriate to admix, for example, hole-transport materials and/or electron-transport materials with the polymer in order selectively to adjust the charge transport in the layer.

The matrix material employed can in general be all materials which are known for this purpose in accordance with the prior art. The triplet level of the matrix material is preferably higher than the triplet level of the emitter, i.e. the unit of the formula (1) in the polymer according to the invention.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 and WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778 or the unpublished applications DE 102009048791.3 and DE 102010005697.9.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-transporting matrix material and an electrically inert matrix material which is not involved or not significantly involved in charge transport, as described, for example, in WO 2010/108579.

It is furthermore preferred to employ two or more triplet emitters together with a matrix, where at least one of the triplet emitters is a polymer which contains units of the formula (1). The further triplet emitter here may likewise be polymerised into the same polymer according to the invention or may be admixed in a further polymer or may be admixed as low-molecular-weight compound. The triplet emitter having the shorter-wave emission spectrum serves here as co-matrix for the triplet emitter having the longer-wave emission spectrum. Thus, for example, the polymers according to the invention containing units of the formula (1) can be employed as co-matrix for triplet emitters emitting at relatively long wavelength, for example for green- or red-emitting triplet emitters. The generation of white emission is furthermore possible in this way.

The cathode preferably comprises metals having a low work function, metal alloys or multilayered structures containing various metals, such as, for example, alkaline-earth metals, alkali metals, main-group metals or lanthanoids (for example Ca, Ba, Mg, Al, In, Mg, Yb, Sm, etc.). Also suitable are alloys containing an alkali metal or alkaline-earth metal and silver, for example an alloy containing magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example Liq (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order either to facilitate irradiation of the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers If further layers are present apart from the emission layer comprising the polymer according to the invention, all materials as are used in accordance with the prior art for the layers can generally be used in these further layers, and the person skilled in the art will be able to combine each of these materials with the materials according to the invention in an electronic device without inventive step.

In a preferred embodiment of the invention, a polymeric hole-injection layer is used. Examples of suitable materials for the hole-injection layer are copolymers triarylamines and aromatic or heteroaromatic groups, for example of triarylamines and indenofluorenes or of triarylamines and carbazoles.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers, in particular the layer comprising the polymer according to the invention, are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing.

The organic electroluminescent device may also be produced as a hybrid system by applying one or more layers from solution and applying one or more other layers by vapour deposition. Thus, for example, it is possible to apply an emitting layer comprising a polymer according to the invention containing a unit of the formula (1) from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished by the following surprising advantages over the prior art:

1. Organic electroluminescent devices comprising polymers obtained using compounds of the formula (1) have a very good lifetime.
2. Organic electroluminescent devices comprising polymers obtained using compounds of the formula (1) have very good efficiency.
3. Using the polymers according to the invention, organic electroluminescent devices which phosphoresce in the blue, green, orange or red colour region are accessible. In particular, blue phosphorescence can only be achieved with difficulty with good efficiencies and lifetimes in accordance with the prior art.
4. The polymers according to the invention have high solubility, if they are uncrosslinked polymers, meaning that they can readily be processed from solution, for example by printing processes.
5. Crosslinked polymers are also accessible simply from the metal complexes according to the invention. This enables simple construction of multilayered electroluminescent devices from solution.

These advantages mentioned above are not accompanied by an impairment of the other electronic properties.

The invention is explained in greater detail by the following examples, without wishing to restrict it thereby. The person skilled in the art will be able to produce further electronic devices according to the invention without inventive step on the basis of the descriptions and will thus be able to carry out the invention throughout the range claimed.

EXAMPLES

The following syntheses are, unless indicated otherwise, carried out under a protective-gas atmosphere in dried solvents. The metal complexes are additionally handled with exclusion of light. The solvents and reagents can be purchased, for example, from Sigma-ALDRICH or ABCR. The synthesis of ligands L1 to L7 is described in the as yet unpublished application EP 10006208.2. Naphth[1',2':4,5]imidazo

[1,2-a]pyridine, [239-25-8], L9, is prepared in accordance with G. Morgan et al., J. Chem. Soc., 1057, 1939.

1) Synthesis of the Ligands 1.1) Ligand L8

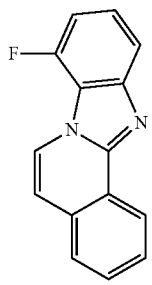

A vigorously stirred mixture of 81.8 g (500 mmol) of 1-chloroisoquinoline [19493-44-8], 75.7 g (520 mmol) of 2-chloro-3-fluoroaniline [21397-08-0], 172.8 g (1250 mmol) of potassium carbonate, 200 g of glass beads (diameter 3 mm), 2.6 g (10 mmol) of triphenylphosphine and 449 mg (2 mmol) of palladium(II) acetate in 1000 ml of o-xylene is heated under reflux for 16 h until the 1-chloroisoquinoline has been consumed. After cooling, the mixture is filtered through a silica-gel bed, rinsed with 1000 ml of THF, and the filtrate is evaporated to dryness. The residue is taken up in 200 ml of ethyl acetate, and 100 ml of n-heptane are slowly added at the boiling temperature. After cooling, the solid which has crystallised out is filtered off with suction, washed twice with 100 ml of n-heptane each time and dried in vacuo. The crude product is recrystallised twice from ethanol and then sublimed in vacuo (p about $10^{-5}$ mbar, T about 150° C.). Yield: 66.2 g (280 mmol), 56%. Purity: 99.5% (HPLC).

1.2) Ligand L10

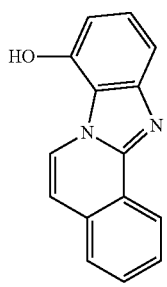 [SMILES: Oc1cccc2nc3c4ccccc4ccn3c12]

Step 1: 2-Bromo-3-methoxymethoxyphenylamine

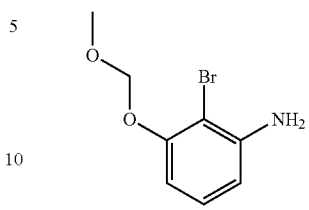

20.0 g (500 mmol) of sodium hydride (60% by weight in mineral oil) are added in portions to a solution of 94.0 g (500 mmol) of 3-amino-2-bromophenol [100367-36-0] in 1000 ml of THF, and the mixture is stirred until the evolution of gas is complete. 38.0 ml (500 mmol) of methoxymethyl chloride [107-30-2] are then added dropwise, and the mixture is stirred at 60° C. for a further 6 h. After cooling, the THF is removed in vacuo, the residue is taken up in 1000 ml of dichloromethane, the organic phase is washed twice with 300 ml of 0.1N NaOH each time, once with 300 ml of saturated sodium chloride solution, dried over potassium carbonate, and the solvent is removed in vacuo. Yield: 112.6 g (485 mmol), 97%. Purity: 99.0% (NMR).

Step 2

A vigorously stirred mixture of 81.8 g (500 mmol) of 1-chloroisoquinoline [19493-44-8], 120.7 g (520 mmol) of 2-bromo-3-methoxymethoxyphenylamine, 172.8 g (1250 mmol) of potassium carbonate, 200 g of glass beads (diameter 3 mm), 2.6 g (10 mmol) of triphenylphosphine and 449 mg (2 mmol) of palladium(II) acetate in 1000 ml of o-xylene is heated under reflux for 16 h until the 1-chloroisoquinoline has been consumed. After cooling, the mixture is filtered through a silica-gel bed, rinsed with 1000 ml of THF, and the filtrate is evaporated to dryness. The residue is dissolved in 500 ml of THF, 50 ml of 0.1N hydrochloric acid are added, and the mixture is stirred at 60° C. for 6 h. After cooling, the THF is removed in vacuo, and the residue is recrystallised three times from ethanol.

Yield: 63.1 g (269 mmol), 54%. Purity: 99.5% (HPLC).

2) Synthesis of Heteroleptic Iridium Complexes

Variant A

Step 1

A mixture of 10 mmol of sodium bisacetylacetonatodichloroiridate(III) [770720-50-8] and 24 mmol of ligand L is melted into a 50 ml glass ampoule in vacuo ($10^{-3}$ mbar). The ampoule is heated at the temperature indicated for the time indicated, during which the molten mixture is stirred with the aid of a magnetic stirrer. After cooling (NOTE: the ampoules are usually under pressure!), the ampoule is opened, the sinter cake is stirred with 100 g of glass beads (diameter 3 mm) in 100 ml of dichloromethane for 3 h and mechanically digested in the process. The fine suspension is decanted off from the glass beads, the solid is filtered off with suction and dried in vacuo.

Step 2

The crude chloro-bridged dimer of the formula [Ir(L)$_2$Cl]$_2$ obtained in this way is suspended in 300 ml of acetone, 4.4 g (20 mmol) of silver(I) trifluoroacetate [2966-50-9] are added to the suspension, and the mixture is heated under reflux for 2 h. After cooling, the silver chloride precipitate is filtered off (P4), 4.8 g (22 mmol) of 6-(4-vinylphenyl)-2,4-hexanedione [59990-76-0], CL1, or 3.3 g (22 mmol) of 5-vinyl-2-pyridinecarboxylic acid [45946-64-3], CL2, or 5.9 g (22 mmol) of 3-[(4-bromophenyl)methyl]-2,4-pentanedione [204927-96-8], CL3, or 4.1 g (22 mmol) of 2,2,6,6-tetramethyl-3,5-heptanedione [1118-71-4], CL4, and 10 ml of triethylamine are added to the filtrate, and the mixture is stirred at room temperature for 20 h. After removal of the acetone in vacuo, the residue is taken up in 200 ml of dichloromethane and filtered through an aluminium oxide column (aluminium oxide, basic, activity grade 1) with a length of about 10 cm. After evaporation of the filtrate, the residue is chromatographed on aluminium oxide (aluminium oxide, basic, activity grade 1) with dichloromethane until a purity >99.5%, preferably greater than 99.9% (HPLC), has been reached.

| Ex. | Ligand L | Ir complex Step 1: Reaction time/temperature | Yield |
|---|---|---|---|
| Ir(L1)$_2$(CL1) | L1 | 260° C./60 h | 25% |
| Ir(L2)$_2$(CL1) | L2 | 260° C./60 h | 23% |
| Ir(L3)$_2$(CL1) | L3 | 260° C./60 h | 27% |

| Ex. | Ligand L | Ir complex Step 1: Reaction time/temperature | Yield |
|---|---|---|---|
| Ir(L4)₂(CL1) | 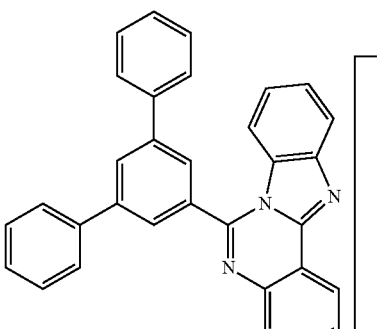<br>L4 | 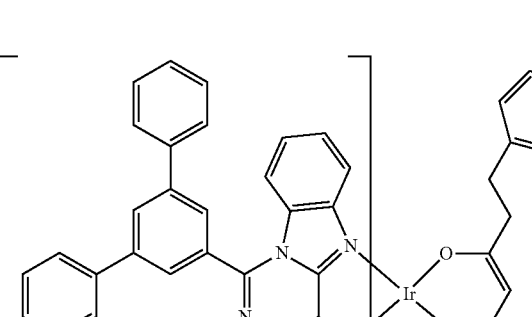<br>260° C./60 h | 32% |
| Ir(L5)₂(CL1) | 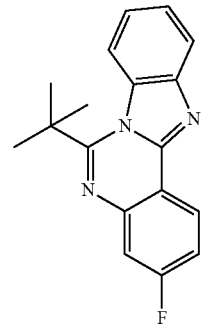<br>L5 | 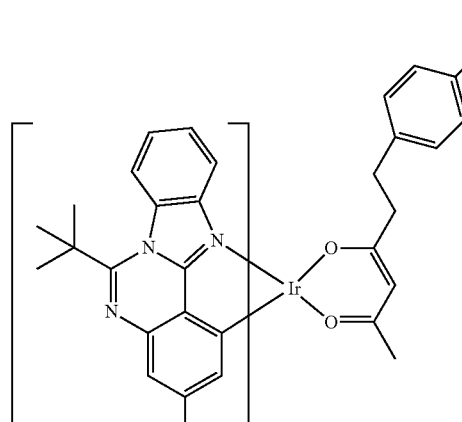<br>265° C./70 h | 18% |
| Ir(L6)₂(CL1) | 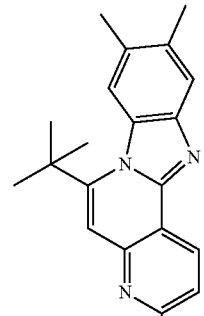<br>L6 | 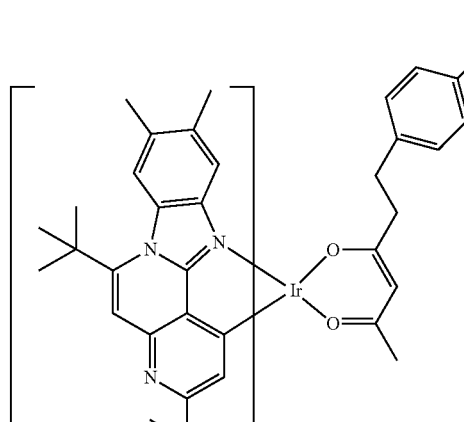<br>270° C./60 h | 21% |

-continued

| Ex. | Ligand L | Ir complex Step 1: Reaction time/temperature | Yield |
|---|---|---|---|
| Ir(L7)₂(CL1) | L7 | 270° C./70 h | 23% |
| Ir(L8)₂(CL1) | L8 | 260° C./30 h | 25% |
| Ir(L9)₂(CL1) | L9 239-25-8 | | 29% |

-continued

| Ex. | Ligand L | Ir complex Step 1: Reaction time/temperature | Yield |
|---|---|---|---|
| Ir(L1)₂(CL2) | L1 | such as Ir(L1)₂(CL1) | 20% |
| Ir(L5)₂(CL2) | L5 | such as Ir(L5)₂(CL1) | 19% |
| Ir(L1)₂(CL3) | L1 | such as Ir(L1)₂(CL1) | 26% |
| Ir(L10)₂(CL4) | Only 25 mmol of triethylamine are added. | 255° C./24 h | 23% |

Variant B

Example Ir(L1)₂(CL5)

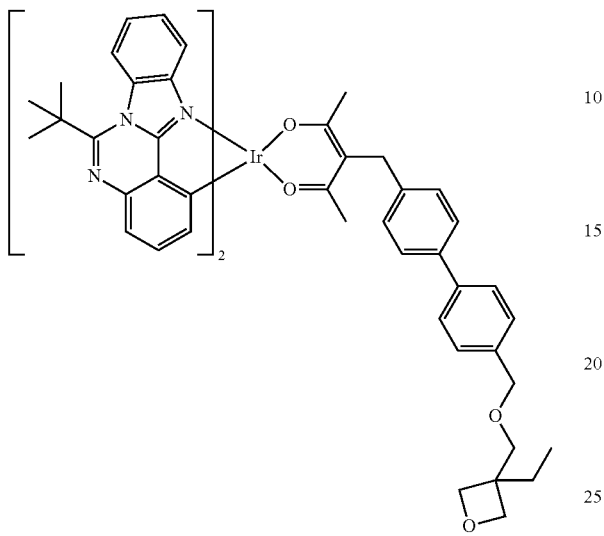

A mixture of 10.1 g (10 mmol) of Ir(L1)₂ (CL3), 3.7 g (11 mmol) of (2-[4-[[(3-ethyl-3-oxetanyl)methoxy]methyl]phenyl]-4,4,5,5-tetramethyl-1,3,2-dioxaborolane [1083097-22-6], 2.8 g (20 mmol) of potassium carbonate, 183 mg (0.6 mmol) of tri-o-tolylphosphine, 22 mg (0.1 mmol) of palladium-(II) acetate, 150 ml of toluene, 50 ml of dioxane and 75 ml of water is heated under reflux for 12 h. After cooling, the organic phase is separated off, washed twice with 100 ml of water each time, once with 100 ml of saturated sodium chloride solution and then dried over magnesium sulfate. The mixture is filtered through a short Celite bed, the filtrate is evaporated in vacuo, and the residue is chromatographed on aluminium oxide (aluminium oxide, basic, activity grade 1) until a purity >99.5 has been reached. Yield: 3.7 g (3.2 mmol), 32%. Purity: 99.5% (HPLC).

Variant C

Example Ir(L11)₂(CL6)

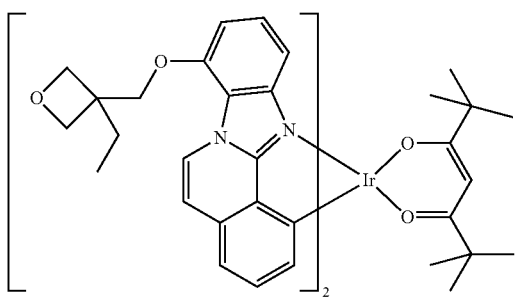

A mixture of 8.4 g (10 mmol) of Ir(L10)₂(CL4), 4.8 g (25 mmol) of 3-ethyl-3-methanesulfonyloxymethyloxetane [3893-75-2], 2.8 g (20 mmol) of potassium carbonate, 332 mg (2 mmol) of potassium iodide and 100 ml of DMF is heated at 130° C. for 4 h. After cooling, 500 ml of dichloromethane are added, the organic phase is washed five times with 500 ml of water, once with 500 ml of saturated sodium chloride solution and dried over potassium carbonate. The potassium carbonate is filtered off via a short Celite bed, the residue is evaporated in vacuo and chromatographed on silica gel with dichloromethane with addition of 1% by weight of triethylamine. Yield: 3.3 g (3.2 mmol), 32%. Purity: 99.8% (HPLC).

3) Synthesis of the Comonomers

3.1) Synthesis of Comonomer M1

Step 1: 2,4-Bisbiphenyl-3-yl-6-(3-bromophenyl)-1,3,5-triazine

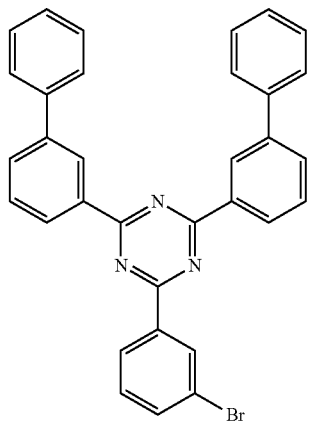 [SMILES: Brc1cccc(-c2nc(-c3cccc(-c4ccccc4)c3)nc(-c3cccc(-c4ccccc4)c3)n2)c1]

171 g (954 mmol) of biphenyl-3-carbonitrile [24973-50-0] are slowly added at 100° C. to a suspension of 60 ml (454 mmol) of 3-bromobenzoyl chloride [1711-09-7], 10 ml (137 mmol) of thionyl chloride and 60.6 g (454 mmol) of aluminium chloride in 800 ml of dichlorobenzene. The temperature increases slightly, and the reaction solution becomes an orange colour. The reaction is stirred at 115° C. until the cloudiness has disappeared. The reaction mixture is cooled to 100° C., aluminium chloride (60.6 g, 454 mmol) is added, and the mixture is stirred at 100° C. for 20 h. The solution is cooled to room temperature, poured into 3 l of methanol, stirred for a further hour, and the precipitate formed is filtered off with suction. The precipitate obtained is washed in hot ethanol, filtered off with suction and dried in vacuo, giving 92 g (170 mmol) of a white solid.

Step 2: 2,4-Bisbiphenyl-3-yl-6-(4'-vinylbiphenyl-3-yl)-1,3,5-triazine (comonomer M1)

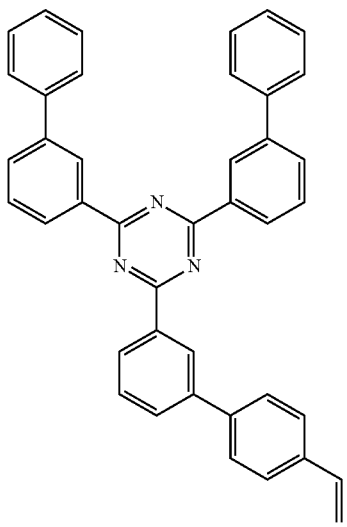 [SMILES: C=Cc1ccc(-c2cccc(-c3nc(-c4cccc(-c5ccccc5)c4)nc(-c4cccc(-c5ccccc5)c4)n3)c2)cc1]

50 g (92.5 mmol) of 2,4-bisbiphenyl-3-yl-6-(3-bromophenyl)-1,3,5-triazine and 13.8 g (93.2 mmol) of styreneboronic acid [2156-04-9] are dissolved in 300 ml of toluene, and 100 ml of a 2 M sodium carbonate solution are added. The reaction mixture is carefully degassed, 200 mg of tetrakistriphenylphosphinepalladium are added, and the mixture is heated under reflux for 20 h. The solution is cooled to room temperature, and the phases are separated. The aqueous phase is extracted three times with toluene, the combined organic phases are subsequently washed twice with water, dried over magnesium sulfate, filtered, and the solvent is stripped off in vacuo. The residue is recrystallised from isopropanol, giving 18.8 g (33.3 mmol) (36%) of a white solid in a purity of 99.7%.

3.2) Synthesis of 5'-p-vinylphenyl-1,1',3',5"-terphenyl (comonomer M2)

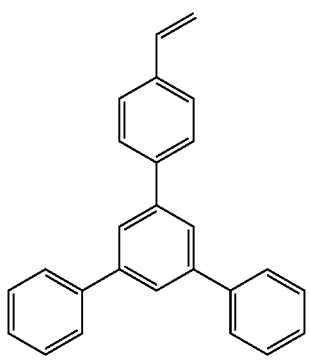 [SMILES: C=Cc1ccc(-c2cc(-c3ccccc3)cc(-c3ccccc3)c2)cc1]

35 g (113 mmol) of 5'-bromoterphenyl [103068-20-8] and 16.7 g (113 mmol) of styreneboronic acid [2156-04-9] are dissolved in 300 ml of toluene, and 100 ml of a 2 M sodium carbonate solution are added. The reaction mixture is carefully degassed, 200 mg of tetrakistriphenylphosphinepalladium are added, and the mixture is heated under reflux for 20 h. The solution is cooled to room temperature, and the phases are separated. The aqueous phase is extracted three times with toluene, the combined organic phases are subsequently washed twice with water, dried over magnesium sulfate, filtered, and the solvent is stripped off in vacuo. The residue is recrystallised from isopropanol, giving 14 g (42 mmol) (37%) of a white solid having a purity of 99.5%.

3.3) Synthesis of [1,1';3',1"]-terphenyl-5'-yl 4'-vinylbiphenyl-3-yl ketone (comonomer M3)

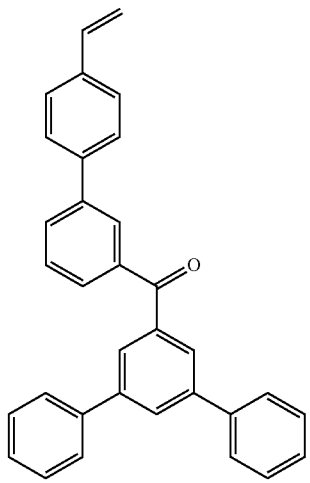 [SMILES: C=Cc1ccc(-c2cccc(C(=O)c3cc(-c4ccccc4)cc(-c4ccccc4)c3)c2)cc1]

25 g (60.5 mmol) of (3-bromophenyl)[1,1';3',1"]-terphenyl-5'-ylmethanone and 9 g (60.5 mmol) of styreneboronic acid [2156-04-9] are dissolved in 300 ml of toluene, and 100 ml of a 2 M sodium carbonate solution are added. The reaction mixture is carefully degassed, 200 mg of tetrakistriphenylphosphinepalladium are added, and the mixture is heated under reflux for 20 h. The solution is cooled to room temperature, and the phases are separated. The aqueous phase is extracted three times with toluene, the combined organic phases are subsequently washed twice with water, dried over magnesium sulfate, filtered, and the solvent is stripped off in vacuo. The residue is recrystallised from heptane/acetonitrile 1:1, giving 12 g (27 mmol) (45%) of a white solid having a purity of 99.9%.

3.4) Synthesis of diphenyl-(4-vinylphenyl)amine (comonomer M4)

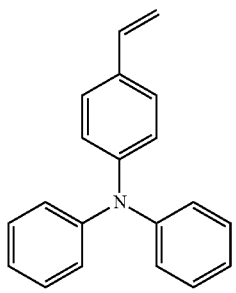 [SMILES: C=Cc1ccc(N(c2ccccc2)c2ccccc2)cc1]

19 g (53 mmol) of methyltriphenylphosphonium bromide [1779-49-3] are suspended in dried THF under protective gas, and 6 g (53 mmol) of potassium tert-butoxide are added in portions at 0° C.; an immediate colour change to orange occurs. 14 g (51.2 mmol) of N,N-diphenyl-p-aminobenzaldehyde [4181-05-9] are added to the reaction solution at 0° C. The mixture is warmed to room temperature and stirred for a further 20 h. The solvent is stripped off in vacuo, the residue is taken up in dichloromethane, the solution is extracted with water, dried over magnesium sulfate, filtered, and the solvent is stripped off in vacuo. The yellow oil obtained is chromatographed over silica gel, giving 12 g (44 mmol) (86%) of a white solid having a purity of 99.5%.

3.5) Synthesis of 2,4-bis-biphenyl-3-yl-6-{3-[2-(3-ethyloxetan-3-yl-methoxy)ethyl]phenyl}-1,3,5-triazine (comonomer M5)

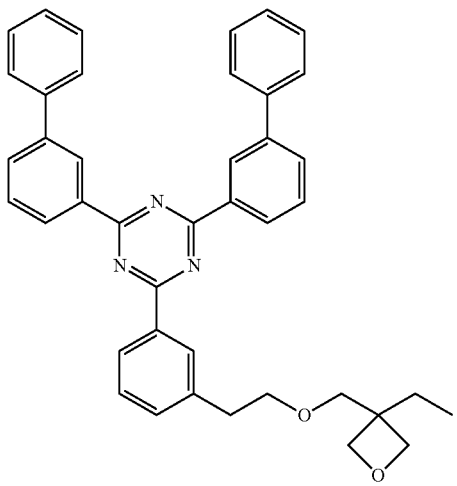 [SMILES: CCC1(COCCc2cccc(-c3nc(-c4cccc(-c5ccccc5)c4)nc(-c4cccc(-c5ccccc5)c4)n3)c2)COC1]

13.1 g (92 mmol) of 3-ethyl-3-vinyloxymethyloxetane and 11.3 g (60.8 mmol) of 9-BBN dimer are dissolved in 200 ml of toluene at room temperature under protective gas and stirred for 20 h. During the reaction, the suspension of 9-BBN slowly dissolves. 50 g (92 mmol) of 2,4-bis-biphenyl-3-yl-6-(3-bromophenyl)-1,3,5-triazine and 50 ml of a 1 M NaOH solution are subsequently added to the reaction solution. The reaction mixture is carefully degassed, 200 mg of tetrakistriphenylphosphino-palladium are added, and the mixture is heated under reflux for 20 h. The solution is cooled to room temperature, and the phases are separated. The aqueous phase is extracted three times with toluene, the combined organic phases are subsequently washed twice with water, dried over magnesium sulfate, filtered, and the solvent is stripped off in vacuo. The residue is recrystallised from ethanol/toluene 3:1, giving 54 g (89 mmol) (97%) of a white solid in a purity of 99:8%.

4) Polymerisation Procedures 4.1) General Polymerisation Procedure for the Styryl Group as Polymerisable Group The monomers are dissolved in the composition indicated in Table 1 in 20 ml of toluene in a concentration of 1 mol/l at 80° C. under protective gas. 64 mg of AIBN are subsequently added, and the mixture is stirred at 80° C. for a further 2 h. The reaction solution is cooled to room temperature, and the polymer is obtained by precipitation in 100 ml of methanol (slowly using a Pasteur pipette). The precipitate is filtered off with suction and subsequently re-dissolved in toluene and again precipitated in methanol and filtered off with suction. The polymer is dried in a vacuum drying cabinet. This polymerisation procedure is used for polymers P1 to P9.

4.2) General Polymerisation Procedure for the Oxetane Groups as Polymerisable Group The monomers are dissolved in the composition indicated in Table 1 in 20 ml of toluene in a concentration of 1 mol/l at room temperature under protective gas. 31 mg of tropylium hexachloroantimonate are subsequently added, and the mixture is stirred at 40° C. for a further 5 h. The reaction solution is cooled to room temperature, and the polymer is obtained by precipitation in 100 ml of methanol (slowly using a Pasteur pipette). The precipitate is filtered off with suction and subsequently re-dissolved in toluene and again precipitated in methanol and filtered off with suction. The polymer is dried in a vacuum drying cabinet. This polymerisation procedure is used for polymers P10 to P13.

TABLE 1

Composition of the polymers

| Polymer | M1 [%] | M2 [%] | M3 [%] | M4 [%] | M5 [%] | Ir complex/[%] |
|---|---|---|---|---|---|---|
| P1 |  | 48 | 48 |  |  | Ir(L1)$_2$(CL1)/4 |
| P2 | 48 |  | 48 |  |  | Ir(L1)$_2$(CL1)/4 |
| P3 | 40 |  | 40 | 16 |  | Ir(L1)$_2$(CL1)/4 |
| P4 | 40 |  | 40 | 16 |  | Ir(L1)$_2$(CL5)/4 |
| P5 |  | 48 | 48 |  |  | Ir(L9)$_2$(CL1)/4 |
| P6 |  | 44 | 44 |  |  | Ir(L9)$_2$(CL1)/12 |
| P7 | 40 |  | 40 | 16 |  | Ir(L5)$_2$(CL1)/4 |
| P8 | 40 |  | 40 | 16 |  | Ir(L7)$_2$(CL1)/4 |
| P9 | 40 |  | 40 | 12 |  | Ir(L7)$_2$(CL1)/8 |
| P10 |  |  |  |  | 96 | Ir(L1)$_2$(CL5)/4 |
| P11 |  |  |  |  | 92 | Ir(L1)$_2$(CL5)/8 |
| P12 |  |  |  |  | 96 | Ir(L11)$_2$(CL6)/4 |
| P13 |  |  |  |  | 92 | Ir(L11)$_2$(CL6)/8 |

TABLE 2

Molecular weights and yield of the polymers according to the invention

| Polymer | Mn [gmol⁻¹] | Mw [gmol⁻¹] | PD | Yield |
|---|---|---|---|---|
| P1 | 47,000 | 15,400 | 3.05 | 48% |
| P2 | 133,000 | 49,300 | 2.70 | 61% |
| P3 | 125,000 | 82,700 | 1.51 | 58% |
| P4 | 123,000 | 71,200 | 1.73 | 58% |
| P5 | 66,200 | 28,600 | 2.31 | 53% |
| P6 | 76,800 | 39,300 | 2.95 | 55% |
| P7 | 153,000 | 88,300 | 1.73 | 63% |
| P8 | 105,200 | 62,700 | 1.68 | 55% |
| P9 | 121,500 | 68,800 | 1.77 | 64% |
| P10 | 185,200 | 102,700 | 1.80 | 45% |
| P11 | 203,400 | 123,600 | 1.64 | 43% |
| P12 | 164,400 | 98,600 | 1.67 | 47% |
| P13 | 208,000 | 122,100 | 1.70 | 43% |

5) Production of a PLED

The production of a polymeric organic light-emitting diode (PLED) has already been described many times in the literature (for example WO 2004/037887). In order to explain the present invention by way of example, a PLED is produced by spin coating with polymers P1 to P11 from Table 2.

To this end, use is made of substrates from Technoprint (soda-lime glass) to which the ITO structure (indium tin oxide, a transparent, conductive anode) is applied.

The substrates are cleaned with deionised water and a detergent (Deconex 15 PF) in a clean room and then activated by UV/ozone plasma treatment. An 80 nm layer of PEDOT (PEDOT is a polythiophene derivative (Baytron P VAI 4083sp.) from H. C. Starck, Goslar, which is supplied as aqueous dispersion) is then applied as buffer layer by spin coating, likewise in a clean room. The spin rate required depends on the degree of dilution and the specific spin coater geometry (typical for 80 nm: 4500 rpm). In order to remove residual water from the layer, the substrates are dried by heating at 180° C. on a hotplate for 10 minutes. Then, firstly 20 nm of an interlayer (typically a hole-dominated polymer, here HIL-012 from Merck) and then 65 nm of the polymer layers are applied from toluene solutions (concentration of interlayer 5 g/l, for polymers P1 to P5 in each case 8 g/l) under an inert-gas atmosphere (nitrogen or argon). The two layers are dried by heating at 180° C. for at least 10 minutes. The Ba/Al cathode is then applied by vapour deposition (high-purity metals from Aldrich, particularly barium 99.99% (Order No. 474711); vapour-deposition units from Lesker, inter alia, typical vapour-deposition pressure 5×10⁻⁶ mbar). In order to protect, in particular, the cathode against air and atmospheric moisture, the device is finally encapsulated and then characterised.

To this end, the devices are clamped in holders specifically manufactured for the substrate size and provided with spring contacts. A photodiode with eye response filter can be placed directly on the measurement holder in order to exclude influences from extraneous light.

The voltages are typically increased from 0 to max. 20 V in 0.2 V steps and reduced again. For each measurement point, the current through the device and the photocurrent obtained is measured by the photodiode. In this way, the IVL data of the test devices are obtained. Important characteristic quantities are the maximum efficiency measured ("eff." in cd/A) and the voltage required for 1000 cd/m².

In order, in addition, to know the colour and the precise electroluminescence spectrum of the test devices, the voltage required for 1000 cd/m² is applied again after the first measurement, and the photodiode is replaced by a spectrum measuring head. This is connected to a spectrometer (Ocean Optics) by an optical fibre. The colour coordinates (CIE: Commission International de l'éclairage, 1931 standard observer) can be derived from the measured spectrum.

TABLE 3

Device results of the polymers according to the invention

| Polymer | CIE [x:y] | U [V] @ 1000 cd/m² | Eff. [cd/A] at 100 cd/m² | EQE [%] at 1000 cd/m² |
|---|---|---|---|---|
| P1 | 0.15:0.31 | 4.8 | 30.4 | 14.7 |
| P2 | 0.15:0.29 | 4.9 | 33.1 | 16.3 |
| P3 | 0.15:0.29 | 4.4 | 31.5 | 15.6 |
| P4 | 0.15:0.30 | 4.6 | 34.2 | 16.9 |
| P5 | 0.39:0.55 | 3.5 | 43.2 | 12.6 |
| P6 | 0.40:0.57 | 3.4 | 49.0 | 14.5 |
| P7 | 0.15:0.24 | 5.1 | 24.2 | 14.4 |
| P8 | 0.15:0.24 | 5.2 | 28.0 | 16.8 |
| P9 | 0.15:0.24 | 4.8 | 26.9 | 16.2 |
| P10 | 0.15:0.29 | 4.9 | 28.1 | 14.2 |
| P11 | 0.15:0.31 | 4.4 | 31.3 | 15.9 |
| P12 | 0.16:0.31 | 4.9 | 28.6 | 13.8 |
| P13 | 0.17:0.33 | 4.6 | 33.0 | 16.0 |

The invention claimed is:
1. A compound of the formula (1),

$$M(L)_n(L')_m \qquad \text{formula (1)}$$

containing a moiety $M(L)_n$ of the formula (2) or formula (3):

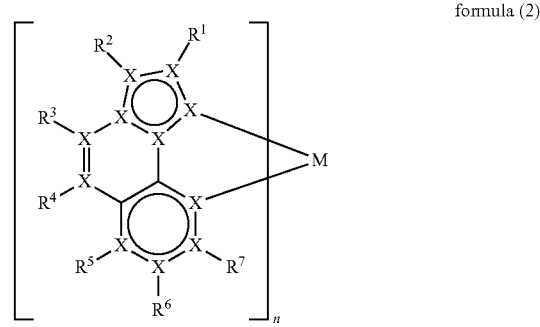

formula (2)

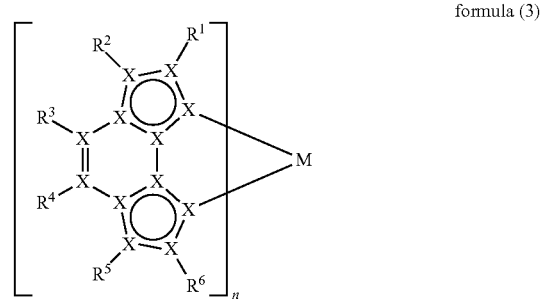

formula (3)

where the following applies to the symbols and indices used:

M is a metal;

X is selected on each occurrence, identically or differently, from the group consisting of C and N; all X here together represent a 14 π electron system;

R¹ to R⁷ is on each occurrence, identically or differently, a polymerisable group PG or H, D, F, Cl, Br, I, N(R⁸)₂, CN, NO₂, Si(R⁸)₃, B(OR⁸)₂, C(=O)R⁸, P(=O)(R⁸)₂, S(=O)R$^8$, S(=O)$_2$R$^8$, OSO$_2$R$^8$, a straight-chain alkyl, alkoxy or thioalkoxy group having 1 to 40 C atoms or an alkenyl, alkynyl or imine group having 2 to 40 C atoms or a branched or cyclic alkyl, alkoxy or thioalkoxy group having 3 to 40 C atoms, where the above-mentioned alkyl, alkoxy, thioalkoxy, alkenyl, alkynyl and imine groups may each be substituted by one or more radicals R$^8$, where one or more non-adjacent CH$_2$ groups is optionally replaced by R$^8$C=CR$^8$, Si(R$^8$)$_2$, Ge(R$^8$)$_2$, Sn(R$^8$)$_2$, C=O, C=S, C=Se, C=NR$^8$, P(=O)(R$^8$), SO, SO$_2$, NR$^8$, O, S or CONR$^8$ and where one or more H atoms is optionally replaced by D, F, Cl, Br, I, CN or NO$_2$, or an aromatic or heteroaromatic ring system having 5 to 60 aromatic ring atoms, which is optionally in each case be substituted by one or more radicals R$^8$, or an aryloxy or heteroaryloxy group having 5 to 60 aromatic ring atoms, which is optionally substituted by one or more radicals R$^8$, or an aralkyl or heteroaralkyl group having 5 to 60 aromatic ring atoms, which is optionally substituted by one or more radicals R$^8$, or a diarylamino group, diheteroarylamino group or arylheteroarylamino group having 10 to 40 aromatic ring atoms, which is optionally substituted by one or more radicals R$^8$; R$^1$ and R$^2$ and/or R$^2$ and R$^3$ and/or R$^4$ and R$^5$ and/or R$^5$ and R$^6$ and/or R$^6$ and R$^7$ here may also form a mono- or polycyclic, aliphatic, aromatic and/or benzo-fused ring system with one another; furthermore, R$^3$ and R$^4$ may form a mono- or polycyclic, in each case aliphatic ring system with one another;

with the proviso that R$^1$, R$^2$, R$^3$, R$^4$, R$^5$, R$^6$ or R$^7$ represents a free electron pair if the group X to which this radical R$^1$, R$^2$, R$^3$, R$^4$, R$^5$, R$^6$ or R$^7$ is bonded is a nitrogen atom having a saturated valence;

R$^8$ is on each occurrence, identically or differently, H, D, F, Cl, Br, I, N(R$^9$)$_2$, CN, NO$_2$, Si(R$^9$)$_3$, B(OR$^9$)$_2$, C(=O)R$^9$, P(=O)(R$^9$)$_2$, S(=O)R$^9$, S(=O)$_2$R$^9$, OSO$_2$R$^9$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals R$^9$, where one or more non-adjacent CH$_2$ groups is optionally replaced by R$^9$C=CR$^9$, C=C, Si(R$^9$)$_2$, Ge(R$^9$)$_2$, Sn(R$^9$)$_2$, C=O, C=S, C=Se, C=NR$^9$, P(=O)(R$^9$), SO, SO$_2$, NR$^9$, O, S or CONR$^9$ and where one or more H atoms is optionally replaced by D, F, Cl, Br, I, CN or NO$_2$, or an aromatic or heteroaromatic ring system having 5 to 60 aromatic ring atoms, which is optionally in each case be substituted by one or more radicals R$^9$, or an aryloxy or heteroaryloxy group having 5 to 60 aromatic ring atoms, which is optionally substituted by one or more radicals R$^9$, or an aralkyl or heteroaralkyl group having 5 to 60 aromatic ring atoms, which is optionally substituted by one or more radicals R$^8$, or a diarylamino group, diheteroarylamino group or arylheteroarylamino group having 10 to 40 aromatic ring atoms, which is optionally substituted by one or more radicals R$^9$; two or more adjacent radicals R$^8$ here may form a mono- or polycyclic, aliphatic or aromatic ring system with one another;

R$^9$ is on each occurrence, identically or differently, H, D, F, CN or an aliphatic, aromatic and/or heteroaromatic hydrocarbon radical having 1 to 20 C atoms, in which, in addition, one or more H atoms is optionally replaced by D or F; two or more substituents R$^9$ here optionally forms a mono- or polycyclic, aliphatic or aromatic ring system with one another;

PG is a polymerisable group, with the proviso that the polymerisable group is not selected from Cl, Br, I and B(OR$^8$)$_2$; and furthermore with the proviso that, if one or more of the radicals R$^1$ to R$^7$ as polymerisable group PG are selected from an alkenyl or an alkynyl group, it is a terminal alkenyl or alkynyl group having 3 to 40 C atoms, where individual CH$_2$ groups or individual H atoms may also be replaced by the groups mentioned above in the case of R$^1$ to R$^7$; and furthermore with the proviso that, if one or more of the radicals R$^1$ to R$^7$ as polymerisable group PG is selected from a group Si(R$^8$)$_3$, R$^8$ stands either for Cl or for an alkoxy group having 1 to 40 C atoms;

L' is, identically or differently on each occurrence, a co-ligand;

n is 1, 2 or 3;

m is 0, 1, 2, 3 or 4;

a plurality of ligands L here may also be linked to one another or L is optionally linked to L' via a single bond or a bridge V and thus form a tridentate, tetradentate, pentadentate or hexadentate ligand system;

wherein at least one of the radicals R$^1$ to R$^7$ and/or at least one radical on the ligand stands for a polymerisable group PG.

2. The compound according to claim 1, wherein the moieties of the formula (2) are selected from the formula (2a) and the moieties of the formula (3) are selected from the formula (3a),

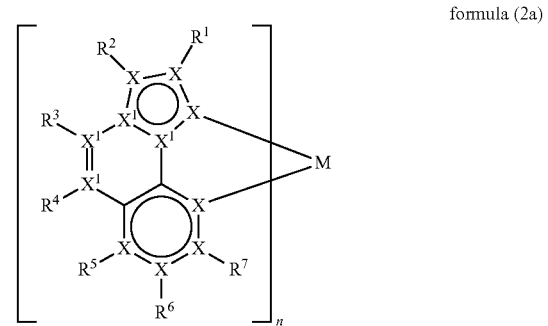

formula (2a)

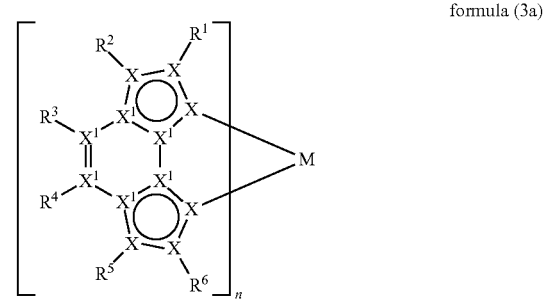

formula (3a)

where symbols and indices used have the meanings given in claim 1 and furthermore:

X$^1$ is, identically or differently on each occurrence, C or N, with the proviso that at least one group X$^1$ stands for N.

3. The compound according to claim 1, wherein the moieties of the formula (2) are selected from the formulae (4), (5) and (6) and the moieties of the formula (3) are selected from the formulae (7) and (8), formula (4)
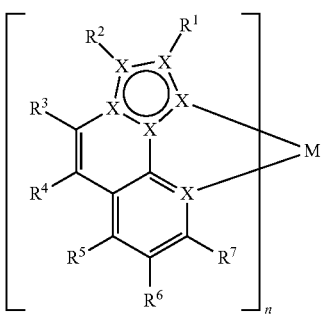

formula (5)
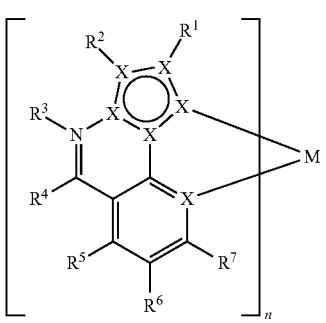

formula (6)
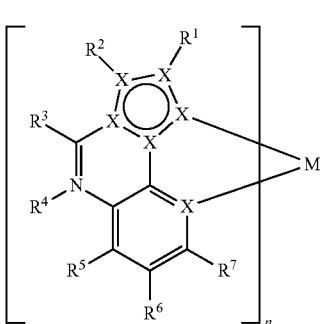

formula (7)
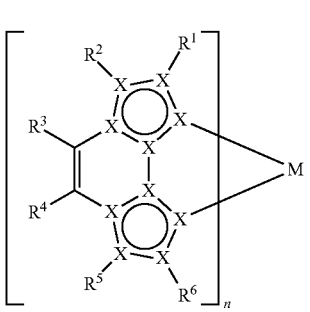

formula (8)
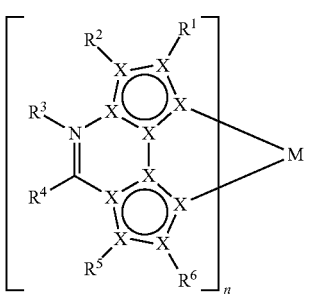

where the symbols and indices have the meanings indicated in claim 1.

4. The compound according to claim 1, wherein the moieties of the formula (2) or (3) are selected from the formulae (78) and (79),

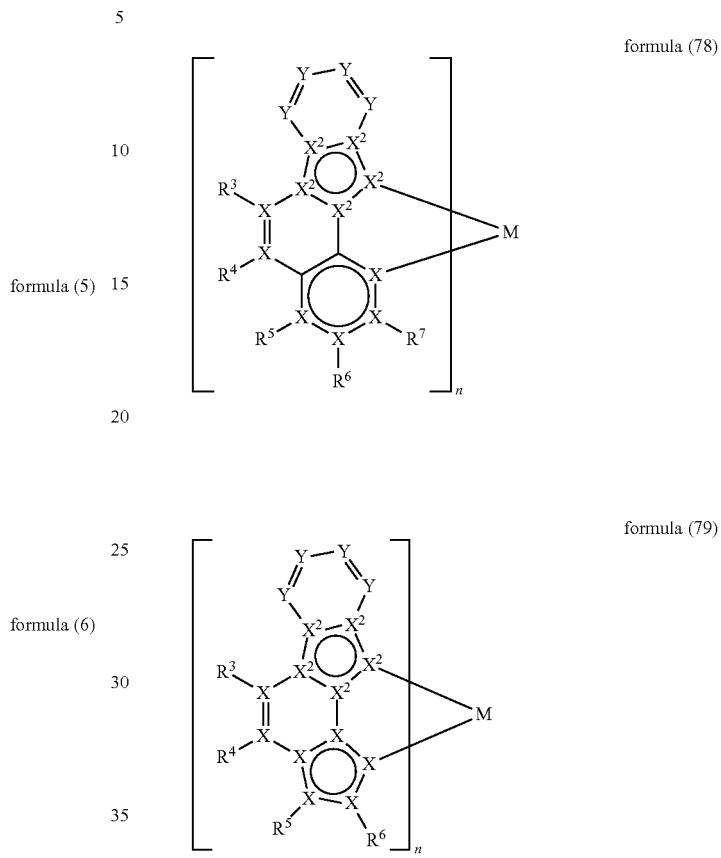

where symbols and indices used have the meanings given in claim 1 and furthermore:

Y is, identically or differently on each occurrence, $CR^8$ or N, with the proviso that a maximum of two symbols Y stand for N; and $X^2$ is, identically or differently on each occurrence, C or N, with the proviso that precisely two symbols $X^2$ stand for N and the other symbols $X^2$ stand for C.

5. The compound according to claim 1, wherein the moieties of the formulae (78) and (79) are selected from the formulae (78a) to (78d) and (79a) to (79d), -continued
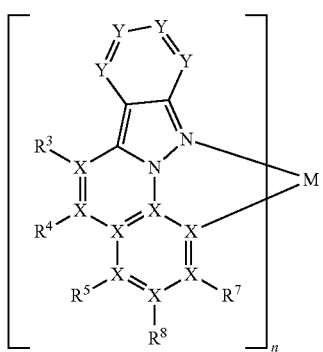
formula (78b)
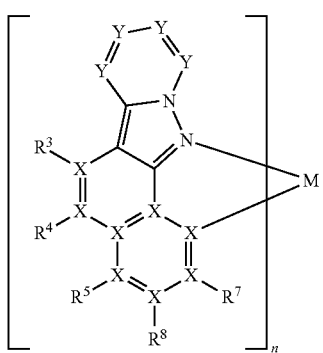
formula (78c)
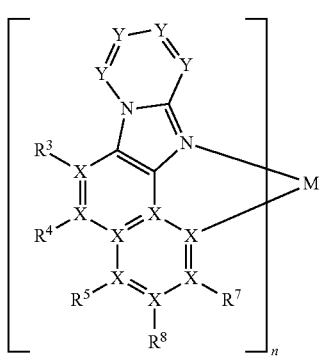
formula (78d)
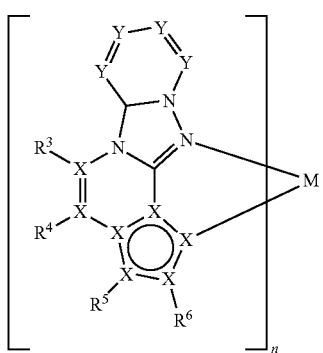
formula (79a)
-continued
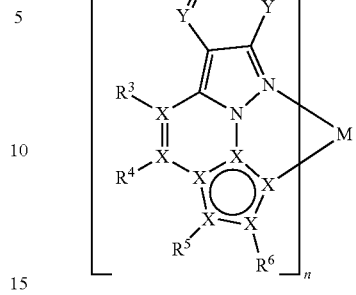
formula (79b)
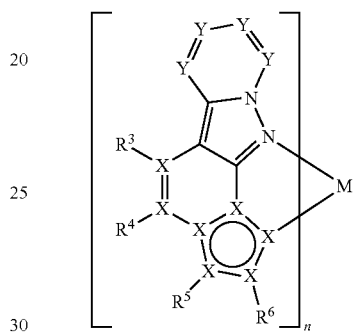
formula (79c)
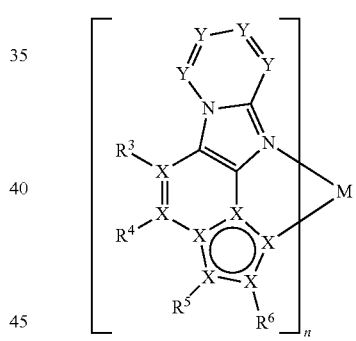
formula (79d)
where the symbols and indices used have the meanings given in claim 1.
6. The compound according to claim 1, selected from the compounds of the formulae (94) to (101),
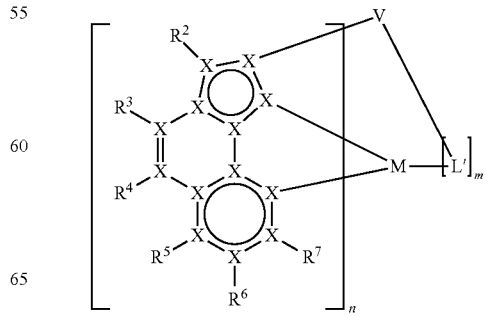
formula (94)

-continued formula (95)
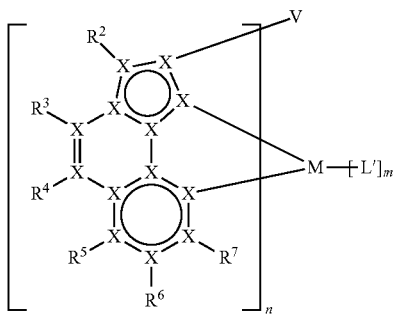

formula (96)
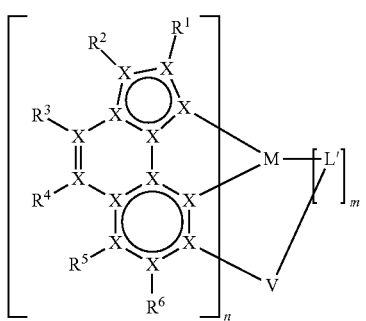

formula (97)
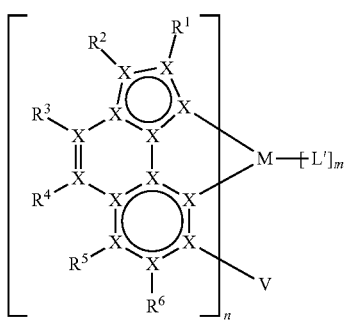

formula (98)
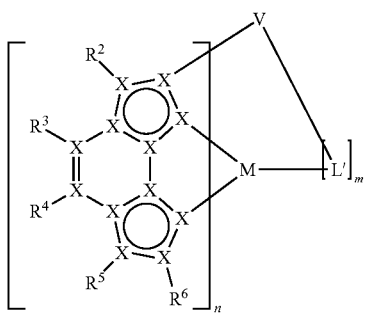

formula (99)
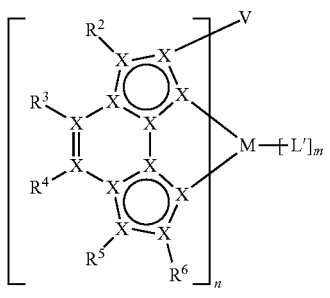

-continued formula (100)
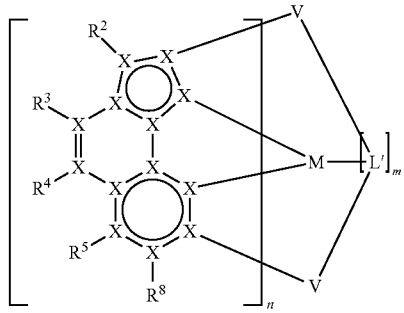

formula (101)
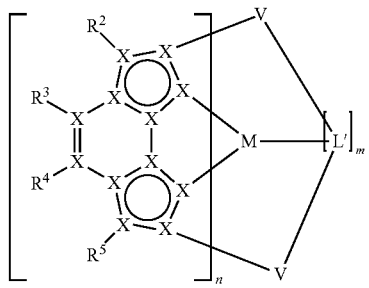

where symbols used have the meanings given in claim 1 and V represents a single bond or a bridging unit containing 1 to 80 atoms from the third, fourth, fifth and/or sixth main group, which is optionally substituted by one or more radicals R1, or a 3- to 6-membered homo- or heterocycle which covalently bonds the part-ligands L to one another or L to L' to one another.

7. The compound according to claim 1, wherein L' is selected from the group consisting of carbon monoxide, nitrogen monoxide, alkyl cyanides, aryl cyanide, alkyl isocyanide, aryl isocyanide, amine, phosphine, arsine, stibine, nitrogen-containing heterocycle, carbene, hydride, deuteride, the halides F—, Cl—, Br— or I—, alkylacetylide, arylacetylide, cyanide, cyanate, isocyanate, thiocyanate, isothiocyanate, aliphatic or aromatic alcoholate, aliphatic or aromatic thioalcoholate, amide, carboxylate, aryl group, O2-, S2-, carbide, nitrene, N3-, diamine, imine, diimine, diphosphine, 1,3-diketonate, 3-ketonates derived from 3-ketoesters, carboxylates derived from aminocarboxylic acids, salicyliminate, dialcoholate, dithiolate, borates of nitrogen-containing heterocycles and ligands which, with the metal, form a cyclometallated five-membered ring or six-membered ring having at least one metal-carbon bond.

8. The compound according to claim 1, wherein the polymerisable group PG is selected from alkenyl or alkynyl groups having 2 to 40 C atoms, where, if one or more of the groups R1 to R7 are selected as polymerisable alkenyl or alkynyl group, they are alkenyl or alkynyl groups having 3 to 40 C atoms which carry a terminal double or triple bond, oxetane, oxirane, groups which undergo a polycycloaddition, carboxylic acid derivatives, amine, alcohol, silane group Si(R8)3, where at least two groups R8 stands for Cl or an alkoxy group having 1 to 20 C atoms.

9. The compound according to claim 1, wherein the compound has one, two or three polymerisable groups PG.

10. A process for the preparation of a polymer utilizing the compound according to claim 1.

11. A polymer obtained by polymerisation of the compound according to claim 1 and optionally further monomers, where the polymerization reaction takes place via the polymerizable group PG.

12. The polymer according to claim 11, wherein further structural units are present, selected from units which have hole-injection and/or hole-transport properties, units which have electron-injection and/or electron-transport properties, units which exhibit electrophosphorescence, units which improve the transfer from the singlet state to the triplet state, units which influence the emission color of the resultant polymers, units which are used as backbone and units which influence the film morphology and/or the rheological properties of the polymer.

13. A formulation comprising one or more compounds according to claim 1.

14. A formulation comprising one or more polymers according to claim 11.

15. An electronic device which comprises the polymer according to claim 11.

16. The electronic device as claimed in claim 15, wherein the device is an organic electroluminescent device, organic integrated circuit, organic field-effect transistor, organic thin-film transistor, organic light-emitting transistor, organic solar cell, organic optical detector, organic photoreceptor, organic field-quench device, light-emitting electrochemical cell or organic laser diode.

17. An organic electroluminescent device which comprises the polymer according to claim 11, wherein the polymer is used in an emitting layer as a pure substance or in a mixture with one or more further polymers or low-molecular-weight compounds.

18. A process for the production of the electronic device which comprises applying the compound according to claim 1, optionally together with further monomers, as a layer and polymerised and/or crosslinked in the layer of the electronic device or in that the compound according to claim 1, optionally together with further monomers, is polymerised, and this polymer is applied as a layer from solution or by means of a printing process.

19. The compound according to claim 1, wherein m is zero, and n is 2 or 3.

20. The compound according to claim 2, wherein m is zero, and n is 2 or 3.

21. The compound according to claim 3, wherein m is zero, and n is 2 or 3.

* * * * *